US011395611B2

(12) United States Patent
Bullington et al.

(10) Patent No.: US 11,395,611 B2
(45) Date of Patent: *Jul. 26, 2022

(54) FLUID DIVERSION MECHANISM FOR BODILY-FLUID SAMPLING

(71) Applicant: Magnolia Medical Technologies, Inc., Seattle, WA (US)

(72) Inventors: Gregory J. Bullington, Seattle, WA (US); Richard G. Patton, Seattle, WA (US); Jay M. Miazga, Langley, WA (US); Shan E. Gaw, Seattle, WA (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/525,682

(22) Filed: Nov. 12, 2021

(65) Prior Publication Data

US 2022/0071533 A1 Mar. 10, 2022

Related U.S. Application Data

(63) Continuation of application No. 16/376,745, filed on Apr. 5, 2019, now abandoned, which is a continuation (Continued)

(51) Int. Cl.
*A61B 5/00* (2006.01)
*A61B 5/15* (2006.01)
(Continued)

(52) U.S. Cl.
CPC ........ *A61B 5/150221* (2013.01); *A61B 5/153* (2013.01); *A61B 5/15003* (2013.01);
(Continued)

(58) Field of Classification Search
CPC .......... A61B 5/150221; A61B 5/15003; A61B 5/150236; A61B 5/150244;
(Continued)

(56) References Cited

U.S. PATENT DOCUMENTS 2,707,953 A   5/1955 Ryan
2,992,974 A   7/1961 Belcove et al.
(Continued)

FOREIGN PATENT DOCUMENTS

CN    86103696 A   1/1987
CN    2115767 U    9/1992
(Continued)

OTHER PUBLICATIONS

Office Action for U.S. Appl. No. 16/299,962, dated Dec. 26, 2019, 14 pages.
(Continued)

*Primary Examiner* — May A Abouelela
(74) *Attorney, Agent, or Firm* — Cooley LLP

(57) ABSTRACT

An apparatus includes a housing, a fluid reservoir, a flow control mechanism, and an actuator. The housing defines an inner volume and has an inlet port that can be fluidically coupled to a patient and an outlet port. The fluid reservoir is disposed in the inner volume to receive and isolate a first volume of a bodily-fluid. The flow control mechanism is rotatable in the housing from a first configuration, in which a first lumen places the inlet port is in fluid communication with the fluid reservoir, and a second configuration, in which a second lumen places the inlet port in fluid communication with the outlet port. The actuator is configured to create a negative pressure in the fluid reservoir and is configured to rotate the flow control mechanism from the first configuration to the second configuration after the first volume of bodily-fluid is received in the fluid reservoir.

30 Claims, 36 Drawing Sheets

Related U.S. Application Data of application No. 14/662,676, filed on Mar. 19, 2015, now Pat. No. 10,292,633, which is a continuation of application No. 14/494,208, filed on Sep. 23, 2014, now Pat. No. 9,022,951, which is a continuation of application No. 14/493,796, filed on Sep. 23, 2014, now Pat. No. 9,022,950, which is a continuation of application No. PCT/US2013/043289, filed on May 30, 2013, which is a continuation-in-part of application No. 13/904,691, filed on May 29, 2013, now Pat. No. 9,060,724.

(60) Provisional application No. 61/652,887, filed on May 30, 2012.

(51) Int. Cl.
*A61B 5/153* (2006.01)
*A61B 10/00* (2006.01)
*A61B 5/155* (2006.01)

(52) U.S. Cl.
CPC ........ *A61B 5/155* (2013.01); *A61B 5/150236* (2013.01); *A61B 5/150244* (2013.01); *A61B 5/150251* (2013.01); *A61B 5/150389* (2013.01); *A61B 5/150503* (2013.01); *A61B 5/150992* (2013.01); *A61B 10/007* (2013.01); *A61B 10/0048* (2013.01); *A61B 10/0051* (2013.01); *A61B 2010/008* (2013.01); *A61B 2010/0061* (2013.01); *A61B 2010/0077* (2013.01)

(58) Field of Classification Search
CPC ........ A61B 5/150251; A61B 5/150389; A61B 5/150503; A61B 5/150992; A61B 5/153; A61B 5/155; A61B 10/0048; A61B 10/0051; A61B 10/007; A61B 2010/0061; A61B 2010/0077; A61B 2010/008
USPC ........................................................ 600/579
See application file for complete search history.

(56) References Cited

U.S. PATENT DOCUMENTS

| | | | |
|---|---|---|---|
| 3,013,557 A | 12/1961 | Pallotta | |
| 3,098,016 A | 7/1963 | Cooper et al. | |
| 3,382,865 A | 5/1968 | Worral, Jr. | |
| 3,405,706 A | 10/1968 | Cinqualbre | |
| 3,467,021 A | 9/1969 | Green | |
| 3,467,095 A | 9/1969 | Ross | |
| 3,494,351 A | 2/1970 | Horn | |
| 3,494,352 A | 2/1970 | Russo et al. | |
| 3,577,980 A | 5/1971 | Cohen | |
| 3,604,410 A | 9/1971 | Whitacre | |
| 3,635,798 A | 1/1972 | Kirkham et al. | |
| 3,648,684 A | 3/1972 | Barnwell et al. | |
| 3,680,558 A | 8/1972 | Kapelowitz | |
| 3,730,168 A | 5/1973 | Mcwhorter | |
| 3,741,197 A * | 6/1973 | Sanz | A61B 5/150267 600/583 |
| 3,777,773 A | 12/1973 | Tolbert | |
| 3,803,810 A | 4/1974 | Rosenberg | |
| 3,817,240 A * | 6/1974 | Ayres | A61B 5/150221 600/584 |
| 3,831,602 A | 8/1974 | Broadwin | |
| 3,834,372 A | 9/1974 | Turney | |
| 3,835,835 A | 9/1974 | Thompson et al. | |
| 3,848,579 A | 11/1974 | Villa-Real | |
| 3,848,581 A | 11/1974 | Cinqualbre et al. | |
| 3,874,367 A * | 4/1975 | Ayres | A61B 5/15003 600/577 |
| 3,886,930 A * | 6/1975 | Ryan | A61B 5/15003 600/584 |
| 3,890,203 A | 6/1975 | Mehl | |
| 3,890,968 A | 6/1975 | Pierce et al. | |
| 3,937,211 A | 2/1976 | Merten | |
| 3,945,380 A | 5/1976 | Dabney et al. | |
| 3,960,139 A | 6/1976 | Bailey | |
| 3,978,846 A | 9/1976 | Bailey | |
| 3,996,923 A | 12/1976 | Guerra | |
| 4,056,101 A | 11/1977 | Geissler et al. | |
| 4,057,050 A * | 11/1977 | Sarstedt | A61B 5/150351 604/125 |
| 4,063,460 A | 12/1977 | Svensson | |
| 4,077,395 A | 3/1978 | Woolner | |
| 4,106,497 A * | 8/1978 | Percarpio | A61B 5/150221 600/579 |
| 4,133,304 A | 1/1979 | Bailey | |
| 4,133,863 A | 1/1979 | Koenig | |
| 4,150,089 A | 4/1979 | Linet | |
| 4,154,229 A * | 5/1979 | Nugent | A61B 5/150351 600/577 |
| 4,166,450 A | 9/1979 | Abramson | |
| 4,190,426 A | 2/1980 | Ruschke | |
| 4,193,400 A | 3/1980 | Loveless et al. | |
| 4,207,870 A * | 6/1980 | Eldridge | A61B 5/150732 604/167.03 |
| 4,210,173 A | 7/1980 | Choksi et al. | |
| 4,212,308 A | 7/1980 | Percarpio | |
| 4,238,207 A | 12/1980 | Ruschke | |
| 4,257,416 A | 3/1981 | Prager | |
| 4,275,730 A | 6/1981 | Hussein | |
| 4,298,358 A | 11/1981 | Ruschke | |
| 4,327,746 A | 5/1982 | Feaster | |
| 4,340,067 A | 7/1982 | Rattenborg | |
| 4,340,068 A | 7/1982 | Kaufman | |
| 4,349,035 A | 9/1982 | Thomas et al. | |
| 4,370,987 A | 2/1983 | Bazell et al. | |
| 4,398,544 A | 8/1983 | Nugent et al. | |
| 4,411,275 A | 10/1983 | Raitto | |
| 4,412,548 A * | 11/1983 | Hoch | A61B 5/150213 600/577 |
| 4,416,290 A | 11/1983 | Lutkowski | |
| 4,425,235 A | 1/1984 | Cornell et al. | |
| 4,436,098 A * | 3/1984 | Kaufman | A61B 5/1545 604/199 |
| 4,444,203 A * | 4/1984 | Engelman | A61B 5/150496 600/576 |
| 4,459,997 A | 7/1984 | Sarstedt | |
| 4,509,534 A | 4/1985 | Tassin, Jr. | |
| 4,608,996 A | 9/1986 | Brown | |
| 4,654,027 A | 3/1987 | Dragan et al. | |
| 4,657,027 A | 4/1987 | Paulsen | |
| 4,657,160 A | 4/1987 | Woods et al. | |
| 4,673,386 A | 6/1987 | Gordon | |
| 4,676,256 A | 6/1987 | Golden | |
| 4,679,571 A | 7/1987 | Frankel et al. | |
| 4,705,497 A | 10/1987 | Shitaokoshi et al. | |
| 4,714,461 A | 12/1987 | Gabel | |
| 4,715,854 A | 12/1987 | Vaillancourt | |
| 4,772,273 A | 9/1988 | Alchas | |
| 4,865,583 A | 9/1989 | Tu | |
| 4,879,098 A | 11/1989 | Oberhardt et al. | |
| 4,886,072 A | 12/1989 | Percarpio et al. | |
| 4,890,627 A | 1/1990 | Haber et al. | |
| 4,904,240 A | 2/1990 | Hoover | |
| 4,980,297 A | 12/1990 | Haynes et al. | |
| 4,988,339 A | 1/1991 | Vadher | |
| 5,027,827 A | 7/1991 | Cody et al. | |
| 5,032,116 A | 7/1991 | Peterson et al. | |
| 5,045,185 A | 9/1991 | Ohnaka et al. | |
| 5,052,403 A | 10/1991 | Haber et al. | |
| 5,066,284 A | 11/1991 | Mersch et al. | |
| 5,084,034 A | 1/1992 | Zanotti | |
| 5,097,842 A | 3/1992 | Bonn | |
| 5,100,394 A | 3/1992 | Dudar et al. | |
| 5,108,927 A | 4/1992 | Dom | |
| 5,116,323 A | 5/1992 | Kreuzer et al. | |
| 5,122,129 A | 6/1992 | Olson et al. | |
| 5,135,489 A | 8/1992 | Jepson et al. | |

(56) References Cited

U.S. PATENT DOCUMENTS

| | | | |
|---|---|---|---|
| 5,222,502 A * | 6/1993 | Kurose | A61B 5/150732 |
| | | | 600/584 |
| 5,269,317 A | 12/1993 | Bennett | |
| 5,330,464 A | 7/1994 | Mathias et al. | |
| 5,354,537 A | 10/1994 | Mathias | |
| 5,360,011 A | 11/1994 | McCallister | |
| 5,395,339 A | 3/1995 | Talonn et al. | |
| 5,417,673 A | 5/1995 | Gordon | |
| 5,429,610 A | 7/1995 | Vaillancourt | |
| 5,431,811 A | 7/1995 | Tusini et al. | |
| 5,439,450 A | 8/1995 | Haedt | |
| 5,450,856 A | 9/1995 | Norris | |
| 5,454,786 A | 10/1995 | Harris | |
| 5,466,228 A | 11/1995 | Evans | |
| 5,472,605 A | 12/1995 | Zuk, Jr. | |
| 5,485,854 A | 1/1996 | Hollister | |
| 5,507,299 A | 4/1996 | Roland | |
| 5,520,193 A * | 5/1996 | Suzuki | A61B 5/1545 |
| | | | 604/126 |
| 5,522,804 A | 6/1996 | Lynn | |
| 5,573,510 A | 11/1996 | Isaacson | |
| 5,575,777 A | 11/1996 | Cover et al. | |
| 5,577,513 A | 11/1996 | Van Vlasselaer | |
| 5,603,700 A | 2/1997 | Daneshvar | |
| 5,632,906 A | 5/1997 | Ishida et al. | |
| 5,649,912 A | 7/1997 | Peterson | |
| 5,691,486 A | 11/1997 | Behringer et al. | |
| 5,749,857 A * | 5/1998 | Cuppy | A61M 25/0606 |
| | | | 604/161 |
| 5,762,633 A | 6/1998 | Whisson | |
| 5,772,608 A | 6/1998 | Dhas | |
| 5,785,682 A | 7/1998 | Grabenkort | |
| 5,811,658 A | 9/1998 | Van Driel et al. | |
| 5,824,001 A | 10/1998 | Erskine | |
| 5,857,983 A | 1/1999 | Douglas et al. | |
| 5,865,812 A | 2/1999 | Correia | |
| 5,871,699 A | 2/1999 | Ruggeri | |
| 5,876,926 A | 3/1999 | Beecham | |
| 5,882,318 A | 3/1999 | Boyde | |
| 5,911,705 A | 6/1999 | Howell | |
| 5,922,551 A | 7/1999 | Durbin et al. | |
| 5,961,472 A | 10/1999 | Swendson et al. | |
| 5,971,956 A | 10/1999 | Epstein | |
| 5,980,830 A | 11/1999 | Savage et al. | |
| 6,001,307 A | 12/1999 | Naka et al. | |
| 6,010,633 A | 1/2000 | Zuk, Jr. et al. | |
| 6,016,712 A | 1/2000 | Warden et al. | |
| 6,050,957 A | 4/2000 | Desch | |
| 6,093,179 A | 7/2000 | O'Hara et al. | |
| 6,106,509 A | 8/2000 | Loubser | |
| 6,126,643 A | 10/2000 | Vaillancouert | |
| 6,159,164 A | 12/2000 | Neese et al. | |
| 6,210,909 B1 | 4/2001 | Guirguis | |
| 6,224,561 B1 | 5/2001 | Swendson et al. | |
| 6,254,581 B1 | 7/2001 | Scott | |
| 6,306,614 B1 | 10/2001 | Romaschin et al. | |
| 6,325,975 B1 | 12/2001 | Naka et al. | |
| 6,328,726 B1 | 12/2001 | Ishida et al. | |
| 6,355,023 B1 | 3/2002 | Roth et al. | |
| 6,364,890 B1 | 4/2002 | Lum et al. | |
| 6,368,306 B1 | 4/2002 | Koska | |
| 6,387,086 B2 | 5/2002 | Mathias et al. | |
| 6,398,743 B1 * | 6/2002 | Halseth | A61B 5/15003 |
| | | | 604/164.12 |
| 6,403,381 B1 | 6/2002 | Mann et al. | |
| 6,478,775 B1 | 11/2002 | Galt et al. | |
| 6,506,182 B2 | 1/2003 | Estabrook et al. | |
| 6,511,439 B1 | 1/2003 | Tabata et al. | |
| 6,520,948 B1 | 2/2003 | Mathias et al. | |
| 6,569,117 B1 * | 5/2003 | Ziv | A61M 39/02 |
| | | | 604/246 |
| 6,592,555 B1 | 7/2003 | Wen-Pi | |
| 6,626,884 B1 | 9/2003 | Dillon et al. | |
| 6,638,252 B2 | 10/2003 | Moulton et al. | |
| 6,648,835 B1 | 11/2003 | Shemesh | |
| 6,692,479 B2 | 2/2004 | Kraus et al. | |
| 6,695,004 B1 | 2/2004 | Raybuck | |
| 6,716,187 B1 | 4/2004 | Jorgensen et al. | |
| 6,733,433 B1 | 5/2004 | Fell | |
| 6,736,783 B2 | 5/2004 | Blake et al. | |
| 6,746,420 B1 | 6/2004 | Prestidge et al. | |
| 6,843,775 B2 | 1/2005 | Hyun | |
| 6,860,871 B2 | 3/2005 | Kuracina et al. | |
| 6,905,483 B2 | 6/2005 | Newby et al. | |
| 6,913,580 B2 | 7/2005 | Stone | |
| 6,945,948 B2 | 9/2005 | Bainbridge et al. | |
| 7,044,941 B2 | 5/2006 | Mathias et al. | |
| 7,052,603 B2 | 5/2006 | Schick | |
| 7,055,401 B2 | 6/2006 | Prybella et al. | |
| 7,087,047 B2 | 8/2006 | Kraus et al. | |
| 7,141,097 B2 | 11/2006 | Leahey | |
| 7,241,281 B2 | 7/2007 | Coelho et al. | |
| 7,306,736 B2 | 12/2007 | Collins et al. | |
| 7,314,452 B2 | 1/2008 | Madonia | |
| 7,316,662 B2 | 1/2008 | Delnevo et al. | |
| 7,335,188 B2 | 2/2008 | Graf | |
| 7,351,228 B2 | 4/2008 | Keane et al. | |
| 7,384,416 B2 | 6/2008 | Goudaliez et al. | |
| 7,461,671 B2 | 12/2008 | Ehwald et al. | |
| 7,479,131 B2 | 1/2009 | Mathias et al. | |
| 7,614,857 B2 | 11/2009 | Fuechslin et al. | |
| 7,615,033 B2 | 11/2009 | Leong | |
| 7,618,407 B2 | 11/2009 | Demay et al. | |
| 7,648,491 B2 | 1/2010 | Rogers | |
| 7,666,166 B1 | 2/2010 | Emmert et al. | |
| 7,744,573 B2 | 6/2010 | Gordon et al. | |
| 7,766,879 B2 | 8/2010 | Tan et al. | |
| 8,070,725 B2 | 12/2011 | Christensen | |
| 8,197,420 B2 * | 6/2012 | Patton | A61B 5/150503 |
| | | | 600/573 |
| 8,231,546 B2 | 7/2012 | Patton | |
| 8,282,605 B2 | 10/2012 | Tan et al. | |
| 8,287,499 B2 | 10/2012 | Miyasaka | |
| 8,337,418 B2 | 12/2012 | Patton | |
| 8,349,254 B2 | 1/2013 | Hoshino et al. | |
| 8,377,040 B2 | 2/2013 | Burkholz et al. | |
| 8,382,712 B2 | 2/2013 | Kim | |
| 8,383,044 B2 | 2/2013 | Davis et al. | |
| 8,412,300 B2 | 4/2013 | Sonderegger | |
| 8,523,826 B2 * | 9/2013 | Layton, Jr. | A61M 39/16 |
| | | | 604/533 |
| 8,535,241 B2 * | 9/2013 | Bullington | A61B 10/0045 |
| | | | 604/249 |
| 8,540,663 B2 * | 9/2013 | Davey | A61M 1/30 |
| | | | 604/93.01 |
| 8,568,371 B2 * | 10/2013 | Siopes | A61M 39/26 |
| | | | 251/903 |
| 8,574,203 B2 | 11/2013 | Stout et al. | |
| 8,603,009 B2 * | 12/2013 | Tan | A61B 5/150213 |
| | | | 600/573 |
| 8,647,286 B2 | 2/2014 | Patton | |
| 8,672,962 B2 | 3/2014 | Brenneman | |
| 8,795,198 B2 | 8/2014 | Tan et al. | |
| 8,827,958 B2 | 9/2014 | Bierman et al. | |
| 8,864,684 B2 * | 10/2014 | Bullington | A61B 10/0048 |
| | | | 600/576 |
| 8,920,454 B2 | 12/2014 | Hyoue | |
| 9,022,950 B2 * | 5/2015 | Bullington | A61B 5/15003 |
| | | | 600/576 |
| 9,022,951 B2 * | 5/2015 | Bullington | A61B 10/007 |
| | | | 600/576 |
| 9,060,724 B2 * | 6/2015 | Bullington | A61B 5/150099 |
| 9,060,725 B2 | 6/2015 | Bullington et al. | |
| 9,134,286 B2 | 9/2015 | Saiki et al. | |
| 9,138,572 B2 * | 9/2015 | Zeytoonian | A61M 39/26 |
| 9,149,576 B2 | 10/2015 | Bullington et al. | |
| 9,155,495 B2 * | 10/2015 | Bullington | A61B 5/150236 |
| 9,204,864 B2 * | 12/2015 | Bullington | A61B 10/0096 |
| 9,295,416 B2 | 3/2016 | Bartfield et al. | |
| 9,314,201 B2 | 4/2016 | Burkholz et al. | |
| 9,597,028 B2 | 3/2017 | Marchiarullo et al. | |
| 9,743,873 B2 | 8/2017 | Gunnerson et al. | |

(56) References Cited

U.S. PATENT DOCUMENTS

| | | |
|---|---|---|
| 9,743,874 B2 | 8/2017 | Kashmirian |
| 9,855,386 B2 | 1/2018 | Close et al. |
| 9,877,675 B2 * | 1/2018 | Baid ................ A61B 5/150389 |
| 9,895,092 B2 | 2/2018 | Burkholz |
| 9,931,466 B2 | 4/2018 | Bullington et al. |
| 9,950,084 B2 | 4/2018 | Bullington et al. |
| 9,999,383 B2 | 6/2018 | Bullington et al. |
| 10,022,530 B2 | 7/2018 | Tekeste |
| 10,206,613 B2 | 2/2019 | Bullington et al. |
| 10,220,139 B2 | 3/2019 | Bullington et al. |
| 10,238,326 B2 | 3/2019 | Gil et al. |
| 10,251,590 B2 | 4/2019 | Bullington et al. |
| 10,292,633 B2 | 5/2019 | Bullington et al. |
| 10,433,779 B2 | 10/2019 | Bullington et al. |
| 10,596,315 B2 | 3/2020 | Bullington et al. |
| 10,736,554 B2 | 8/2020 | Bullington et al. |
| 10,772,548 B2 | 9/2020 | Bullington et al. |
| 11,311,218 B2 | 4/2022 | Bullington et al. |
| 2001/0039058 A1 | 11/2001 | Iheme et al. |
| 2002/0002349 A1 | 1/2002 | Flaherty et al. |
| 2002/0004647 A1 * | 1/2002 | Leong .................. A61B 5/1545 |
| | | 604/168.01 |
| 2002/0107469 A1 | 8/2002 | Bolan et al. |
| 2002/0183651 A1 | 12/2002 | Hyun |
| 2002/0193751 A1 | 12/2002 | Theeuwes et al. |
| 2003/0013991 A1 | 1/2003 | Stone |
| 2003/0055381 A1 | 3/2003 | Wilkinson |
| 2003/0069543 A1 | 4/2003 | Carpenter et al. |
| 2003/0105414 A1 * | 6/2003 | Leong ................. A61B 5/15003 |
| | | 600/576 |
| 2003/0208151 A1 | 11/2003 | Kraus et al. |
| 2004/0009542 A1 | 1/2004 | Dumont et al. |
| 2004/0010228 A1 | 1/2004 | Swenson et al. |
| 2004/0054283 A1 | 3/2004 | Corey et al. |
| 2004/0054333 A1 * | 3/2004 | Theeuwes ......... A61M 5/14276 |
| | | 604/248 |
| 2004/0073171 A1 * | 4/2004 | Rogers .................. A61M 39/26 |
| | | 604/164.13 |
| 2004/0127816 A1 | 7/2004 | Galvao |
| 2004/0147855 A1 * | 7/2004 | Marsden .......... A61B 5/150496 |
| | | 600/576 |
| 2005/0004524 A1 * | 1/2005 | Newby ............ A61B 5/150648 |
| | | 604/164.08 |
| 2005/0148993 A1 | 7/2005 | Mathias et al. |
| 2005/0154368 A1 | 7/2005 | Lim et al. |
| 2005/0161112 A1 | 7/2005 | Ehwald et al. |
| 2005/0199077 A1 | 9/2005 | Prybella et al. |
| 2005/0240161 A1 * | 10/2005 | Crawford ......... A61B 5/150572 |
| | | 604/264 |
| 2005/0245885 A1 | 11/2005 | Brown |
| 2005/0273019 A1 | 12/2005 | Conway et al. |
| 2005/0281713 A1 | 12/2005 | Hampsch et al. |
| 2006/0155212 A1 | 7/2006 | Madonia |
| 2006/0251622 A1 | 11/2006 | Suzuki et al. |
| 2006/0287639 A1 | 12/2006 | Sharp |
| 2007/0083162 A1 * | 4/2007 | O'Reagan ............. A61M 39/26 |
| | | 604/167.03 |
| 2007/0088279 A1 * | 4/2007 | Shue .................. A61M 25/0693 |
| | | 604/168.01 |
| 2007/0100250 A1 | 5/2007 | Kline |
| 2007/0119508 A1 | 5/2007 | West et al. |
| 2007/0287948 A1 | 12/2007 | Sakiewicz |
| 2008/0086085 A1 * | 4/2008 | Brown ............. A61B 5/150389 |
| | | 604/122 |
| 2008/0108954 A1 | 5/2008 | Mathias et al. |
| 2008/0145933 A1 * | 6/2008 | Patton ................... A61B 5/154 |
| | | 435/379 |
| 2008/0167577 A1 * | 7/2008 | Weilbacher .......... A61B 5/1545 |
| | | 600/576 |
| 2008/0185056 A1 | 8/2008 | Diodati et al. |
| 2008/0200837 A1 | 8/2008 | Frazier et al. |
| 2008/0254471 A1 | 10/2008 | Bordano |
| 2008/0255523 A1 | 10/2008 | Grinberg |
| 2008/0319346 A1 * | 12/2008 | Crawford ......... A61B 5/150732 |
| | | 600/576 |
| 2009/0050213 A1 | 2/2009 | Biddell et al. |
| 2009/0192447 A1 | 7/2009 | Andersen et al. |
| 2009/0227896 A1 | 9/2009 | Tan et al. |
| 2009/0301317 A1 | 12/2009 | Andrews |
| 2009/0306601 A1 | 12/2009 | Shaw et al. |
| 2010/0010372 A1 * | 1/2010 | Brown ............... A61B 5/15003 |
| | | 600/573 |
| 2010/0042048 A1 | 2/2010 | Christensen |
| 2010/0057004 A1 * | 3/2010 | Christensen ...... A61M 25/0606 |
| | | 604/122 |
| 2010/0094171 A1 | 4/2010 | Conway et al. |
| 2010/0152681 A1 | 6/2010 | Mathias |
| 2010/0234768 A1 | 9/2010 | Uchiyama et al. |
| 2010/0268118 A1 | 10/2010 | Schweiger |
| 2010/0286513 A1 | 11/2010 | Pollard et al. |
| 2011/0306899 A1 | 12/2011 | Brown et al. |
| 2012/0004619 A1 | 1/2012 | Stephens et al. |
| 2012/0016266 A1 * | 1/2012 | Burkholz .......... A61B 5/150992 |
| | | 600/581 |
| 2012/0035540 A1 | 2/2012 | Ferren et al. |
| 2012/0265099 A1 | 10/2012 | Goodnow, II et al. |
| 2012/0265128 A1 | 10/2012 | Kolln |
| 2013/0158506 A1 | 6/2013 | Harris et al. |
| 2013/0317391 A1 * | 11/2013 | Bullington ......... A61B 5/15003 |
| | | 600/578 |
| 2014/0066880 A1 | 3/2014 | Prince et al. |
| 2014/0221873 A1 | 8/2014 | Hayakawa et al. |
| 2015/0011847 A1 | 1/2015 | Hayden |
| 2015/0018715 A1 | 1/2015 | Walterspiel |
| 2015/0351679 A1 | 12/2015 | Bullington et al. |
| 2016/0008579 A1 * | 1/2016 | Burkholz ........... A61B 5/15003 |
| | | 604/164.08 |
| 2016/0174888 A1 * | 6/2016 | Berthier .......... A61B 5/150503 |
| | | 600/573 |
| 2016/0213294 A1 | 7/2016 | Patton |
| 2017/0071519 A1 | 3/2017 | Gelfand et al. |
| 2018/0160958 A1 | 6/2018 | Baid |
| 2019/0000367 A1 | 1/2019 | Lundquist et al. |
| 2019/0049442 A1 | 2/2019 | Guirguis |
| 2020/0060595 A1 | 2/2020 | Bullington et al. |
| 2021/0353194 A1 | 11/2021 | Bullington et al. |
| 2021/0361206 A1 | 11/2021 | Bullington et al. |
| 2022/0079482 A1 | 3/2022 | Bullington et al. |

FOREIGN PATENT DOCUMENTS

| | | |
|---|---|---|
| CN | 1713928 A | 12/2005 |
| CN | 1901955 A | 1/2007 |
| CN | 2907683 Y | 6/2007 |
| CN | 101060871 A | 10/2007 |
| CN | 101309641 A | 11/2008 |
| CN | 101352357 A | 1/2009 |
| CN | 101437450 A | 5/2009 |
| CN | 101676001 A | 3/2010 |
| CN | 101801445 A | 8/2010 |
| CN | 102548524 A | 7/2012 |
| CN | 102971040 A | 3/2013 |
| CN | 103027727 A | 4/2013 |
| CN | 103477201 A | 12/2013 |
| CN | 105090005 A | 11/2015 |
| CN | 105612346 A | 5/2016 |
| DE | 7 203 008 U | 5/1972 |
| DE | 2 203 858 B2 | 5/1973 |
| DE | 2 541 494 A1 | 3/1977 |
| DE | 299 13 417 U1 | 12/2000 |
| DE | 100 38 026 A1 | 2/2001 |
| DE | 101 34 913 A1 | 2/2003 |
| DE | 101 34 913 C2 | 2/2003 |
| DE | 102 43 129 A1 | 4/2004 |
| EP | 0 207 304 A1 | 1/1987 |
| EP | 0 448 795 | 10/1991 |
| EP | 1 980 204 | 10/2008 |
| FR | 2 110 516 A5 | 6/1972 |
| JP | S53-097289 A | 8/1978 |
| JP | S64-58241 A | 3/1989 |
| JP | H07-16219 A | 1/1995 |

(56) References Cited

FOREIGN PATENT DOCUMENTS

| | | |
|---|---|---|
| JP | 2002-116201 A | 4/2002 |
| JP | 2002-528159 A | 9/2002 |
| JP | 2005-237617 A | 9/2005 |
| JP | 2008-149076 A | 7/2008 |
| JP | 62-42386 B2 | 12/2017 |
| JP | 2018-34009 A | 3/2018 |
| WO | WO 1986/005568 | 9/1986 |
| WO | WO 1990/004351 | 5/1990 |
| WO | WO 1991/018632 | 12/1991 |
| WO | WO 1992/016144 | 10/1992 |
| WO | WO 1995/016395 | 6/1995 |
| WO | WO 1997/018845 | 5/1997 |
| WO | WO 1998/046136 | 10/1998 |
| WO | WO 1999/013925 | 3/1999 |
| WO | WO 1999/048425 | 9/1999 |
| WO | WO 1999/055232 | 11/1999 |
| WO | WO 2000/040291 | 7/2000 |
| WO | WO 2000/041624 | 7/2000 |
| WO | WO 2001/008546 | 2/2001 |
| WO | WO 2002/051520 | 7/2002 |
| WO | WO 2003/008012 | 1/2003 |
| WO | WO 2003/047660 | 6/2003 |
| WO | WO 2003/078964 | 9/2003 |
| WO | WO 2005/068011 | 7/2005 |
| WO | WO 2006/031500 | 3/2006 |
| WO | WO 2007/033319 | 3/2007 |
| WO | WO 2008/101025 | 8/2008 |
| WO | WO 2011/069145 | 6/2011 |
| WO | WO 2012/012127 | 1/2012 |
| WO | WO 2013/181352 | 12/2013 |

OTHER PUBLICATIONS

Office Action for U.S. Appl. No. 15/854,273, dated Mar. 15, 2019, 19 pages.
Office Action for U.S. Appl. No. 16/299,962, dated Dec. 9, 2020, 15 pages.
Office Action for U.S. Appl. No. 16/299,962, dated Jun. 15, 2021, 17 pages.
Office Action for U.S. Appl. No. 16/255,055, dated Mar. 18, 2019, 16 pages.
Notice of Reasons for Rejection for Japanese Application No. 2020-075727, dated Jul. 21, 2021, with English translation, 37 pages.
Extended European Search Report for European Application No. 21167625.9, dated Oct. 8, 2021, 7 pages.
Extended European Search Report dated Aug. 30, 2021 for European Application No. 20207898.6, 8 pages.
Office Action for U.S. Appl. No. 11/955,635, dated Jul. 22, 2010, 11 pages.
Office Action for U.S. Appl. No. 11/955,635, dated Dec. 3, 2010, 11 pages.
Office Action for U.S. Appl. No. 13/335,241, dated Apr. 20, 2012, 12 pages.
Office Action for U.S. Appl. No. 13/458,508, dated Jul. 24, 2012, 13 pages.
Office Action for U.S. Appl. No. 13/675,295, dated May 23, 2013, 15 pages.
Office Action for U.S. Appl. No. 14/089,267, dated Jun. 19, 2014, 13 pages.
Office Action for U.S. Appl. No. 14/498,102, dated Oct. 17, 2017, 20 pages.
Office Action for U.S. Appl. No. 14/498,102, dated Sep. 24, 2018, 18 pages.
Office Action for U.S. Appl. No. 15/088,842, dated Nov. 23, 2016, 20 pages.
Office Action for U.S. Appl. No. 15/432,310, dated Apr. 12, 2017, 14 pages.
Office Action for U.S. Appl. No. 15/435,684, dated Jun. 12, 2017, 19 pages.
Office Action for U.S. Appl. No. 15/448,891, dated Jun. 16, 2017, 25 pages.
Office Action for U.S. Appl. No. 15/457,082, dated Jun. 15, 2017, 22 pages.
Office Action for U.S. Appl. No. 15/829,015, dated Feb. 6, 2018, 24 pages.
Office Action for U.S. Appl. No. 15/829,018, dated Feb. 16, 2018, 13 pages.
Office Action for U.S. Appl. No. 15/829,023, dated Feb. 7, 2018, 25 pages.
Office Action for U.S. Appl. No. 15/832,055, dated Feb. 8, 2018, 21 pages.
Office Action for U.S. Appl. No. 15/832,087, dated Feb. 7, 2018, 24 pages.
Office Action for U.S. Appl. No. 13/954,528, dated Mar. 17, 2014, 10 pages.
Office Action for U.S. Appl. No. 15/832,091, dated Feb. 22, 2018, 16 pages.
Office Action for U.S. Appl. No. 16/299,962, dated May 2, 2019, 14 pages.
Office Action for U.S. Appl. No. 14/493,796, dated Jan. 27, 2015, 7 pages.
Office Action for U.S. Appl. No. 14/494,208, dated Jan. 27, 2015, 7 pages.
Office Action for U.S. Appl. No. 14/662,676, dated Sep. 5, 2018, 25 pages.
Office Action for U.S. Appl. No. 14/712,437 dated Oct. 25, 2018, 20 pages.
Office Action for U.S. Appl. No. 15/854,273, dated Sep. 7, 2018, 15 pages.
Office Action for U.S. Appl. No. 15/854,273, dated Jan. 13, 2020, 13 pages.
Office Action for U.S. Appl. No. 16/376,745, dated May 14, 2021, 13 pages.
Office Action for U.S. Appl. No. 14/096,826, dated Jul. 26, 2017, 12 pages.
Office Action for U.S. Appl. No. 14/096,826, dated Mar. 8, 2018, 14 pages.
Office Action for U.S. Appl. No. 14/728,318, dated May 19, 2017, 26 pages.
Office Action for U.S. Appl. No. 14/728,318, dated Jan. 8, 2018, 36 pages.
Office Action for U.S. Appl. No. 14/728,318, dated Dec. 20, 2018, 26 pages.
Office Action for U.S. Appl. No. 14/049,326, dated Apr. 24, 2015, 10 pages.
Office Action for U.S. Appl. No. 13/952,964, dated Mar. 20, 2015, 11 pages.
Office Action for U.S. Appl. No. 14/926,784, dated May 25, 2018, 15 pages.
Office Action for U.S. Appl. No. 14/926,784, dated Jan. 15, 2019, 15 pages.
Office Action for U.S. Appl. No. 14/926,784, dated Jan. 21, 2020, 17 pages.
Office Action for U.S. Appl. No. 14/264,481, dated Jul. 1, 2015, 13 pages.
International Search Report and Written Opinion for International Application No. PCT/US2007/087951, dated May 16, 2008, 8 pages.
Examination Report for United Kingdom Application No. GB1805101.1, dated May 25, 2018, 8 pages.
International Search Report and Written Opinion for International Application No. PCT/US2013/071491, dated Aug. 5, 2014, 9 pages.
Notification of the First Office Action for Chinese Application No. 201380040468.7, dated Jun. 30, 2016, 9 pages.
Supplementary European Search Report for EP Application No. 13797732.8, dated Dec. 7, 2015, 5 pages.
International Search Report and Written Opinion for International Application No. PCT/US2013/043289, dated Oct. 24, 2013, 15 pages.
Notification of the First Office Action for Chinese Application No. 201380072185.0, dated Sep. 28, 2016, 17 pages.

(56) References Cited

OTHER PUBLICATIONS

Supplementary European Search Report for EP Application No. 13860741.1, dated Jun. 7, 2016, 5 pages.
Extended European Search Report for EP Application No. 17204012.3, dated Feb. 14, 2018, 7 pages.
International Search Report and Written Opinion for International Application No. PCT/US2013/073080, dated Feb. 18, 2014, 14 pages.
Notice of Reasons for Rejection for Japanese Application No. 2015-545813, dated Jul. 4, 2017, 14 pages.
Notice of Reasons for Rejection for Japanese Application No. 2018-086721, dated Mar. 15, 2019, 6 pages.
International Search Report and Written Opinion for International Application No. PCT/US2013/063975, dated Mar. 20, 2014, 16 pages.
International Search Report and Written Opinion for International Application No. PCT/US2013/052493, dated Nov. 27, 2013, 7 pages.
Extended European Search Report for EP Application No. 18188136.8, dated May 16, 2019, 9 pages.
Notice of Reasons for Rejection for Japanese Application No. 2018-081980, dated Feb. 21, 2019, 9 pages.
International Search Report and Written Opinion for International Application No. PCT/US2013/072563, dated Feb. 7, 2014, 11 pages.
Arkin, C. F. et al., "Procedures for the Collection of Diagnostic Blood Specimens by Venipuncture; Approved Standard," Fifth Edition, Clinical and Laboratory Standards Institute, vol. 23, No. 32 (2003), 52 pages.
Barnard, D. R. & Arthur, M. M., "Fibronectin (cold insoluble globulin) in the neonate," Clinical and Laboratory Observations, 102(3): 453-455 (1983).
Baxter, "IV Tubing and Access Devices" authored by and published by Baxter, dated Nov. 6, 2006, 105 pages.
BD Saf-T-Intima Closed IV Catheter System, Becton, Dickinson and Company, 2015 Brochure. Retrieved from the Internet (Sep. 11, 2019) <https://www.bd.com/en-us/offerings/capabilities/infusion-therapy/iv-catheters/bd-saf-tintima-closed-iv-catheter-system>, 2 pages.
BD Vacutainer Passive Shielding Blood Collection Needle Brochure; Becton Dickinson and Company (2005), 2 pages.
Brecher, M. E. et al., "Bacterial Contamination of Blood Components," Clinical Microbiology Reviews, 18(1):195-204 (2005).
Calam, R. R., "Recommended 'Order of Draw' for Collecting Blood Specimens Into Additive-Containing Tubes," Letter to the Editor, Clinical Chemistry, 28(6):1399 (1982), 1 page.
Cartridge and Test Information, Abbott, Art: 714258-01O Rev. Date: Aug. 15, 2016, 6 pages.
Challiner, A. et al., Queen Alexandra Hospital, Portsmouth P06 3LY, "Venous/arterial blood management protection system," Correspondence, p. 169.
De Korte, D. et al., "Diversion of first blood volume results in a reduction of bacterial contamination for whole-blood collections," Vox Sanguinis, 83:13-16 (2002).
De Korte, D. et al., "Effects of skin disinfection method, deviation bag, and bacterial screening on clinical safety of platelet transfusions in the Netherlands," Transfusion, 46: 476-485 (2006).
Edwards Lifesciences, "Conservation. Safety. Simplicity. Edwards Vamp and Vamp Jr. Systems," 2002 Brochure. Retrieved from the Internet (Sep. 11, 2019) <https://www.medline.com/media/catalog/Docs/MKT/VAMPSYSTEMBROCHURE.PDF>, 4 pages.
Ernst, D. J. et al., "NCCLS simplifies the order of draw: a brief history," MLO, 26-27 (2004).
Gottlieb, T., "Hazards of Bacterial Contamination of Blood Products," Anaesth Intens Care, 21: 20-23 (1993).
Hall, K. K. et al., "Updated Review of Blood Culture Contamination," Clinical Microbiology Reviews, 19(4):788-802 (2006).
Hillyer, C. D. et al., "Bacterial Contamination of Blood Components Risks, Strategies, and Regulation," Hematology, 575-589 (2003).
Kim, J. Y. et al., "The Sum of the Parts is Greater Than the Whole: Reducing Blood Culture Contamination," Annals of Internal Medicine, 154:202-203 (2011).
Levin, P. D. et al., "Use of the Nonwire Central Line Hub to Reduce Blood Culture Contamination," Chest, 143(3):640-645 (2013).
Pall Corp., "Leukotrap Filtration Systems for Whole Blood Derived Platelets: Leukotrap RC PL and Leukotrap PL Systems," 2005 Brochure, 2 pages.
Li, Y. et al., "Direct labeling and visualization of blood vessels with lipophilic carbocyanine dye DiI," Nature Protocols, 3(11): 1703-1708 (2008).
Liumbruno, G. M. et al., "Reduction of the risk of bacterial contamination of blood components through diversion of the first part of the donation of blood and blood components," Blood Transfus, 7: 86-93 (2009).
Mayer, G. A., "A Method for the Reliable Determination of Clotting Time in Whole Blood," Can Med Assoc J., 72(12): 927-929 (1955).
McDonald, C. P., "Interventions Implemented to Reduce the Risk of Transmission of Bacteria by Transfusion in the English National Blood Service," Transfus Med Hemother, 38:255-258 (2011).
Meissner, G. F. et al., "A Method Based on the Use of Whole Venous Blood in Capillary Tubes," American Journal of Clinical Pathology, 33(2): 29-31 (1963).
Murphy, M., "Better Blood Transfusion," Journal of the Intensive Core Society, 4(3): 78-80 (2003).
Napolitano, M. et al., "Quality control of bacterial contamination of blood components: the feasibility of diversion system testing," Blood Transfus, 2: 231-232 (2004).
Norberg, A. et al., "Contamination Rates of Blood Cultures Obtained by Dedicated Phlebotomy vs Intravenous Catheter," JAMA, 289(6): 726-729 (2003).
Order of Draw for Multiple Tube Collections, LabNotes, a newsletter from BD Diagnostics,—Preanalytical Systems, 17(1):3 (2007).
Page, C. et al., "Blood conservation devices in critical care: a narrative review," Annals of Intensive Care, 3:14 (2013), 6 pages.
Palavecino, E. L. et al., "Detecting Bacterial Contamination in Platelet Products," Clin. Lab., 52:443-456 (2006).
Patton, R. G. et al., "Innovation for Reducing Blood Culture Contamination: Initial Specimen Diversion Technique," Journal of Clinical Microbiology, 48(12):4501-4503 (2010).
Perez, P. et al., "Multivariate analysis of determinants of bacterial contamination of whole-blood donations," Vox Sanguinis, 82:55-60 (2002).
Proehl, J. A. et al., "Clinical Practice Guideline: Prevention of Blood Culture Contamination, Full Version," 2012 ENA Emergency Nurses Resources Development Committee, Emergency Nurses Association (Dec. 2012), 14 pages.
Quilici, N. et al., "Differential Quantitative Blood Cultures in the Diagnosis of Catheter-Related Sepsis in Intensive Care Units," Clinical Infectious Diseases 25:1066-1070 (1997).
Schuur, J., "Blood Cultures: When Do they Help and When Do They Harm?" Brigham & Women's Hospital, Department of Emergency Medicine, (Jun. 21-23, 2012), 42 pages.
Sheppard, C. A. et al., "Bacterial Contamination of Platelets for Transfusion: Recent Advances and Issues," LabMedicine, 36(12):767-770 (2005).
Shulman, G., "Quality of Processed Blood for Autotransfusion," The Journal of Extra-Corporeal Technology, 32(1): 11-19 (2000).
Sibley, C. D. et al., "Molecular Methods for Pathogen and Microbial Community Detection and Characterization: Current and Potential Application in Diagnostic Microbiology," Infection, Genetics and Evolution 12:505-521 (2012).
Stohl, S. et al., "Blood Cultures at Central Line Insertion in the Intensive Care Unit: Comparison with Peripheral Venipuncture," Journal of Clinical Microbiology, 49(7):2398-2403 (2011).
Tang, M. et al., "Closed Blood Conservation Device for Reducing Catheter-Related Infections in Children After Cardiac Surgery," Critical Care Nurse, 34(5): 53-61 (2014).
Wagner et al., "Diversion of Initial Blood Flow to Prevent Whole-Blood Contamination by Skin Surface Bacteria: an in vitro model," Transfusion, 40:335-338 (2000).
Wang, P. et al., "Strategies on Reducing Blood Culture Contamination," Reviews in Medical Microbiology, 23:63-66 (2012).

(56) References Cited

OTHER PUBLICATIONS

Weinbaum, F. I. et al., "Doing It Right the First Time: Quality Improvement and the Contaminant Blood Culture," Journal of Clinical Microbiology, 35(3): 563-565 (1997).
Weinstein, M. P., "Current Blood Culture Methods and Systems: Clinical Concepts, Technology, and Interpretation of Results," Clinical Infectious Diseases, 23: 40-46 (1996).
Weinstein, M. P., "Minireview: Blood Culture Contamination: Persisting Problems and Partial Progress," Journal of Clinical Microbiology, 41(6): 2275-2278 (2003).
Weinstein, M. P. et al., "The Clinical Significance of Positive Blood Cultures in the 1990s: A Prospective Comprehensive Evaluation of the Microbiology, Epidemiology, and Outcome of Bacteremia and Fungemia in Adults," Clinical Infectious Diseases, 24:584-602 (1997).
Ziegler, et al., "Controlled Clinical Laboratory Comparison of Two Supplemented Aerobic and Anaerobic Media Used in Automated Blood Culture Systems to Detect Bloodstream Infections," J. Clinical Microbiology, 36(3):657-661 (1998).
Zimmon, D. S. et al., "Effect of Portal Venous Blood Flow Diversion on Portal Pressure," J Clin Invest, 65(6):1388-1397 (1980).
Zundert, A. V., "New Closed IV Catheter System," Acta Anaesth. Belg., 56: 283-285 (2005).
Exhibit 01—Defendant's Invalidity Contentions, Invalidity Claim Chart—U.S. Pat. No. 9,855,001 vs *Barnard NPL*, Aug. 30, 2019, 8 pages.
Exhibit 02—Defendant's Invalidity Contentions, Invalidity Claim Chart—U.S. Pat. No. 9,855,001 vs *BD Needle NPL*, Aug. 30, 2019, 7 pages.
Exhibit 03—Defendant's Invalidity Contentions, Invalidity Claim Chart—U.S. Pat. No. 9,855,001 vs U.S. Pat. No. 6,626,884, Aug. 30, 2019, 11 pages.
Exhibit 04—Defendant's Invalidity Contentions, Invalidity Claim Chart—U.S. Pat. No. 9,855,001 vs U.S. Pat. Pub. No. 2005/161112, Aug. 30, 2019, 22 pages.
Exhibit 05—Defendant's Invalidity Contentions, Invalidity Claim Chart—U.S. Pat. No. 9,855,001 vs U.S. Pat. No. 4,673,386, Aug. 30, 2019, 21 pages.
Exhibit 06—Defendant's Invalidity Contentions, Invalidity Claim Chart—U.S. Pat. No. 9,855,001 vs U.S. Pat. No. 4,904,240, Aug. 30, 2019, 15 pages.
Exhibit 07—Defendant's Invalidity Contentions, Invalidity Claim Chart—U.S. Pat. No. 9,855,001 vs *Leukotrap NPL*, Aug. 30, 2019, 38 pages.
Exhibit 09—Defendant's Invalidity Contentions, Invalidity Claim Chart—U.S. Pat. No. 9,855,001 vs U.S. Pat. No. 4,106,497, Aug. 30, 2019, 22 pages.
Exhibit 10—Defendant's Invalidity Contentions, Invalidity Claim Chart—U.S. Pat. No. 9,855,001 vs *Stopcock-Syringe NPL*, Aug. 30, 2019, 85 pages.
Exhibit 11—Defendant's Invalidity Contentions, Invalidity Claim Chart—U.S. Pat. No. 9,855,001 vs *Ziegler NPL*, Aug. 30, 2019, 8 pages.
Exhibit 12—Defendant's Invalidity Contentions, Invalidity Claim Chart—U.S. Pat. No. 10,028,689 vs *Barnard NPL*, Aug. 30, 2019, 12 pages.
Exhibit 13—Defendant's Invalidity Contentions, Invalidity Claim Chart—U.S. Pat. No. 10,028,689 vs U.S. Pat. No. 6,626,884, Aug. 30, 2019, 29 pages.
Exhibit 14—Defendant's Invalidity Contentions, Invalidity Claim Chart—U.S. Pat. No. 10,028,689 vs U.S. Pat. Pub. No. 2005/161112, Aug. 30, 2019, 48 pages.
Exhibit 15—Defendant's Invalidity Contentions, Invalidity Claim Chart—U.S. Pat. No. 10,028,689 vs U.S. Pat. No. 4,673,386, Aug. 30, 2019, 44 pages.
Exhibit 16—Defendant's Invalidity Contentions, Invalidity Claim Chart—U.S. Pat. No. 10,028,689 vs U.S. Pat. No. 4,904,240, Aug. 30, 2019, 31 pages.
Exhibit 17—Defendant's Invalidity Contentions, Invalidity Claim Chart—U.S. Pat. No. 10,028,689 vs *Leukotrap NPL*, Aug. 30, 2019, 113 pages.
Exhibit 19—Defendant's Invalidity Contentions, Invalidity Claim Chart—U.S. Pat. No. 10,028,689 vs U.S. Pat. No. 4,106,497, Aug. 30, 2019, 38 pages.
Exhibit 20—Defendant's Invalidity Contentions, Invalidity Claim Chart—U.S. Pat. No. 10,028,689 vs *Stopcock-Syringe NPL*, Aug. 30, 2019, 268 pages.
Exhibit 21—Defendant's Invalidity Contentions, Invalidity Claim Chart—U.S. Pat. No. 10,220,139 vs U.S. Pat. No. 6,626,884, Aug. 30, 2019, 35 pages.
Exhibit 22—Defendant's Invalidity Contentions, Invalidity Claim Chart—U.S. Pat. No. 10,220,139 vs U.S. Pat. Pub. No. 2005/161112, Aug. 30, 2019, 46 pages.
Exhibit 23—Defendant's Invalidity Contentions, Invalidity Claim Chart—U.S. Pat. No. 10,220,139 vs U.S. Pat. No. 4,207,870, Aug. 30, 2019, 20 pages.
Exhibit 24—Defendant's Invalidity Contentions, Invalidity Claim Chart—U.S. Pat. No. 10,220,139 vs U.S. Pat. No. 6,506,182, Aug. 30, 2019, 15 pages.
Exhibit 25—Defendant's Invalidity Contentions, Invalidity Claim Chart—U.S. Pat. No. 10,220,139 vs U.S. Pat. No. 4,673,386, Aug. 30, 2019, 53 pages.
Exhibit 26—Defendant's Invalidity Contentions, Invalidity Claim Chart—U.S. Pat. No. 10,220,139 vs U.S. Pat. No. 4,904,240, Aug. 30, 2019, 39 pages.
Exhibit 27—Defendant's Invalidity Contentions, Invalidity Claim Chart—U.S. Pat. No. 10,220,139 vs *Leukotrap NPL*, Aug. 30, 2019, 115 pages.
Exhibit 29—Defendant's Invalidity Contentions, Invalidity Claim Chart—U.S. Pat. No. 10,220,139 vs U.S. Pat. No. 4,106,497, Aug. 30, 2019, 45 pages.
Exhibit 30—Defendant's Invalidity Contentions, Invalidity Claim Chart—U.S. Pat. No. 10,220,139 vs *Stopcock-Syringe NPL*, Aug. 30, 2019, 246 pages.
Exhibit 31—Defendant's Invalidity Contentions, Invalidity Claim Chart—U.S. Pat. No. 10,220,139 vs U.S. Pat. No. 4,349,035, Aug. 30, 2019, 26 pages.
Exhibit 32—Defendant's Invalidity Contentions, Invalidity Claim Chart—U.S. Pat. No. 10,220,139 vs U.S. Pat. Pub. No. 2008/0145933A1, Aug. 30, 2019, 39 pages.
Exhibit 33—Defendant's Invalidity Contentions, Invalidity Claim Chart—U.S. Pat. No. 10,039,483 vs *Barnard NPL*, Aug. 30, 2019, 14 pages.
Exhibit 34—Defendant's Invalidity Contentions, Invalidity Claim Chart—U.S. Pat. No. 10,039,483 vs U.S. Pat. No. 6,626,884, Aug. 30, 2019, 22 pages.
Exhibit 35—Defendant's Invalidity Contentions, Invalidity Claim Chart—U.S. Pat. No. 10,039,483 vs U.S. Pat. Pub. No. 2005/161112, Aug. 30, 2019, 45 pages.
Exhibit 36—Defendant's Invalidity Contentions, Invalidity Claim Chart—U.S. Pat. No. 10,039,483 vs U.S. Pat. No. 4,673,386, Aug. 30, 2019, 47 pages.
Exhibit 37—Defendant's Invalidity Contentions, Invalidity Claim Chart—U.S. Pat. No. 10,039,483 vs U.S. Pat. No. 4,904,240, Aug. 30, 2019, 30 pages.
Exhibit 38—Defendant's Invalidity Contentions, Invalidity Claim Chart—U.S. Pat. No. 10,039,483 vs *Leukotrap NPL*, Aug. 30, 2019, 115 pages.
Exhibit 40—Defendant's Invalidity Contentions, Invalidity Claim Chart—U.S. Pat. No. 10,039,483 vs U.S. Pat. No. 4,106,497, Aug. 30, 2019, 45 pages.
Exhibit 41—Defendant's Invalidity Contentions, Invalidity Claim Chart—U.S. Pat. No. 10,039,483 vs *Stopcock-Syringe NPL*, Aug. 30, 2019, 214 pages.
Exhibit 42—Defendant's Invalidity Contentions, Invalidity Claim Chart—U.S. Pat. No. 10,039,483 vs U.S. Pat. Pub. No. 2008/0145933A1, Aug. 30, 2019, 38 pages.
Office Action for U.S. Appl. No. 16/379,128, dated Apr. 26, 2022, 14 pages.
Office Action for U.S. Appl. No. 17/532,382, dated Feb. 7, 2022, 10 pages.

(56) References Cited

OTHER PUBLICATIONS

Office Action for U.S. Appl. No. 16/255,058, dated Mar. 30, 2021, 16 pages.
Office Action for U.S. Appl. No. 17/388,971, dated Nov. 23, 2021, 19 pages.
Office Action for U.S. Appl. No. 17/388,979, dated Dec. 8, 2021, 21 pages.
Extended European Search Report for European Application No. 21167069.0, dated Nov. 10, 2021, 9 pages.
Office Action for Chinese Application No. 201811146373.4, dated Nov. 4, 2020, with English language translation, 17 pages.
Office Action for Chinese Application No. 201811146373.4, dated Aug. 25, 2021, with English language translation, 10 pages.
Office Action for Chinese Application No. 201811146373.4, dated Jan. 29, 2022, with English language translation, 21 pages.
Decision of Rejection for Japanese Application No. 2018-081980, dated Jan. 30, 2020, 11 pages.
Notice of Reasons for Rejection for Japanese Application No. 2020-094488, dated Aug. 2, 2021, 4 pages.
Notice of Reasons for Rejection for Japanese Application No. 2020-094488, dated Mar. 31, 2022, 6 pages.

\* cited by examiner

FLUID DIVERSION MECHANISM FOR BODILY-FLUID SAMPLING

CROSS-REFERENCE TO RELATED APPLICATIONS

This application is a continuation of U.S. patent application Ser. No. 16/376,745, filed Apr. 5, 2019, entitled "Fluid Diversion Mechanism For Bodily-Fluid Sampling," which is a continuation of U.S. patent application Ser. No. 14/662,676, filed Mar. 19, 2015 (now U.S. Pat. No. 10,292,633), entitled "Fluid Diversion Mechanism For Bodily-Fluid Sampling," which is a continuation of U.S. patent application Ser. No. 14/494,208, filed Sep. 23, 2014 (now U.S. Pat. No. 9,022,951), entitled "Fluid Diversion Mechanism For Bodily-Fluid Sampling," which is a continuation of U.S. patent application Ser. No. 14/493,796, filed Sep. 23, 2014 (now U.S. Pat. No. 9,022,950), entitled "Fluid Diversion Mechanism For Bodily-Fluid Sampling," which is a continuation of International Patent Application No. PCT/US2013/043289, filed May 30, 2013, entitled "Fluid Diversion Mechanism For Bodily-Fluid Sampling," which is a continuation-in-part of and claims priority to U.S. patent application Ser. No. 13/904,691, filed May 29, 2013 (now U.S. Pat. No. 9,060,724), entitled "Fluid Diversion Mechanism For Bodily-Fluid Sampling," which claims priority to and the benefit of U.S. Provisional Application No. 61/652,887, filed May 30, 2012, entitled "Fluid Diversion Mechanism for Bodily-Fluid Sampling," the disclosures of which are hereby incorporated by reference in their entireties.

BACKGROUND

The invention relates generally to the parenteral procurement of bodily-fluid samples, and more particularly to devices and methods for parenterally-procuring bodily-fluid samples with reduced contamination from microbes or other contaminants exterior to the bodily-fluid source, such as dermally-residing microbes.

Health care practitioners routinely perform various types of microbial tests on patients using parenterally-obtained bodily-fluids. Patient samples (e.g., bodily-fluids) are sometimes tested for the presence of one or more potentially undesirable microbes, such as bacteria, fungi, or yeast (e.g., *Candida*). Microbial testing may include incubating patient samples in one or more sterile vessels containing culture media that is conducive to microbial growth. Generally, when microbes tested for are present in the patient sample, the microbes flourish over time in the culture medium. After a pre-determined amount of time (e.g., a few hours to several days), the culture medium can be tested for the presence of the microbes. The presence of microbes in the culture medium suggests the presence of the same microbes in the patient sample which, in turn, suggests the presence of the same microbes in the bodily-fluid of the patient from which the sample was obtained. Accordingly, when microbes are determined to be present in the culture medium, the patient may be prescribed one or more antibiotics or other treatments specifically designed to treat or otherwise remove the undesired microbes from the patient.

Patient samples, however, can sometimes become contaminated during procurement. One way in which contamination of a patient sample may occur is by the transfer of microbes from a bodily surface (e.g., dermally-residing microbes) dislodged during needle insertion into a patient and subsequently transferred to a culture medium with the patient sample. The bodily surface microbes may be dislodged either directly or via dislodged tissue fragments, hair follicles, sweat glands and other adnexal structures. The transferred microbes may thrive in the culture medium and eventually yield a positive microbial test result, thereby falsely indicating the presence of such microbes in vivo. Such inaccurate results are a concern when attempting to diagnose or treat a suspected illness or condition. For example, false positive results from microbial tests may result in the patient being unnecessarily subjected to one or more anti-microbial therapies, which may cause serious side effects to the patient including, for example, death, as well as produce an unnecessary burden and expense to the health care system.

As such, a need exists for improved bodily-fluid transfer devices and methods that reduce microbial contamination in bodily-fluid test samples.

SUMMARY

Devices for parenterally-procuring bodily-fluid samples with reduced contamination from microbes exterior to the bodily-fluid source, such as dermally-residing microbes, are described herein. In some embodiments, a device for procuring bodily-fluid samples from a patient includes a housing, a fluid reservoir, a flow control mechanism, and an actuator. The housing includes a proximal end portion and a distal end portion and defines an inner volume therebetween. The housing has an inlet port that is configured to be fluidically coupled to a patient and an outlet port that is configured to be fluidically coupled to a sample reservoir. The fluid reservoir is disposed within the inner volume of the housing and is configured to receive and isolate a first volume of a bodily-fluid withdrawn from the patient. The flow control mechanism defines a first lumen and a second lumen and is disposed in the housing for rotational movement from a first configuration, in which the inlet port is placed in fluid communication with the fluid reservoir such that the bodily-fluid can flow from the inlet port, through the first lumen, and to the fluid reservoir, to a second configuration, in which the inlet port is placed in fluid communication with the outlet port such that the bodily-fluid can flow from the inlet, through the second lumen and to the outlet port. The actuator is configured to create a negative pressure in the fluid reservoir when actuated by a user. The actuator is operably coupled to the flow control mechanism and is configured to rotate the flow control mechanism from the first configuration to the second configuration after the first volume of bodily-fluid is received in the fluid reservoir from the patient.

DETAILED DESCRIPTION

Figure 1:
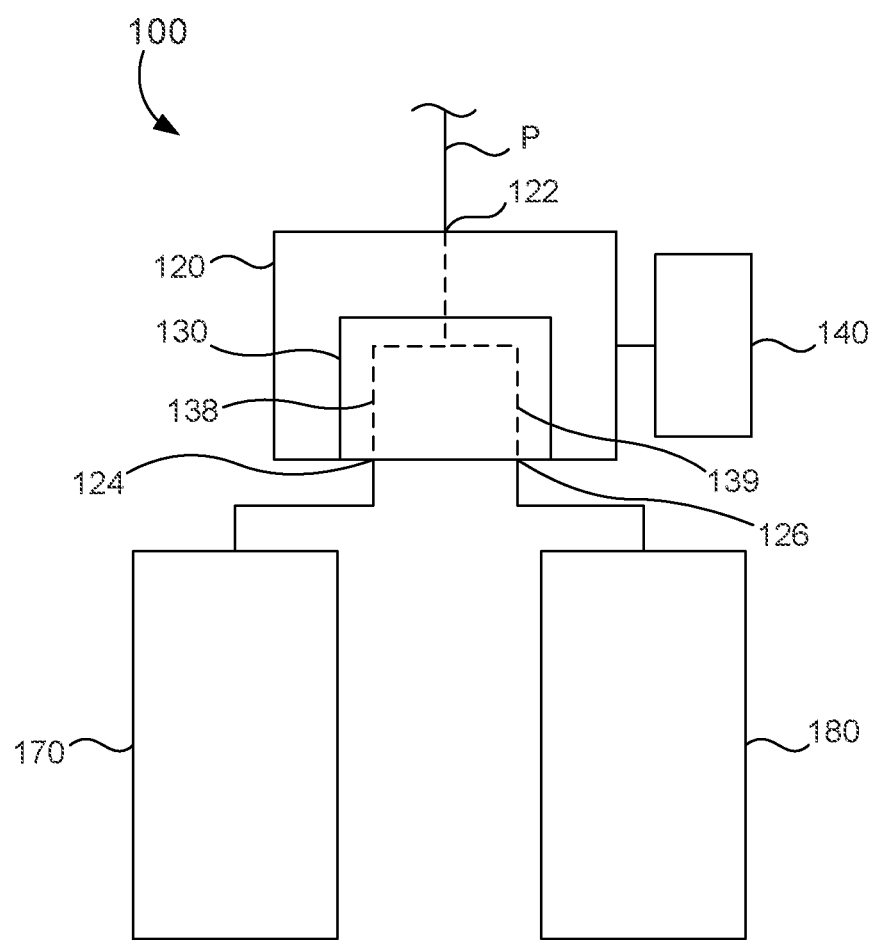
FIG. 1 is a schematic illustration of a bodily-fluid transfer device according to an embodiment.

Devices for parenterally procuring bodily-fluid samples with reduced contamination from microbes exterior to the bodily-fluid source, such as dermally-residing microbes, are described herein. In some embodiments, a device for procuring bodily-fluid samples from a patient includes a housing, a fluid reservoir, a flow control mechanism, and an actuator. The housing includes a proximal end portion and a distal end portion and defines an inner volume therebetween. The housing has an inlet port that is configured to be fluidically coupled to a patient and an outlet port that is configured to be fluidically coupled to a sample reservoir. The fluid reservoir is disposed within the inner volume of the housing and is configured to receive and isolate a first volume of a bodily-fluid withdrawn from the patient. The flow control mechanism defines a first lumen and a second lumen and is disposed in the housing for rotational movement from a first configuration, in which the inlet port is placed in fluid communication with the fluid reservoir such that the bodily-fluid can flow from the inlet port, through the first lumen, and to the fluid reservoir, to a second configuration, in which the inlet port is placed in fluid communication with the outlet port such that the bodily-fluid can flow from the inlet, through the second lumen and to the outlet port. The actuator is configured to create a negative pressure in the fluid reservoir when actuated by a user. The actuator is operably coupled to the flow control mechanism and is configured to rotate the flow control mechanism from the first configuration to the second configuration after the first volume of bodily-fluid is received in the fluid reservoir from the patient.

In some embodiments, a device for procuring bodily-fluid samples from a patient includes a housing, an actuator, a diverter, and a flow control mechanism. The housing has a proximal end portion and a distal end portion and defines an inner volume therebetween. The actuator is movably disposed in the housing. The actuator includes a sealing member and a fluid reservoir defined, at least in part, by the sealing member. The actuator is configured to create a negative pressure in the fluid reservoir when actuated by a user. The diverter is disposed in the housing and has an inlet port that is configured to be fluidically coupled to the patient, a first outlet port that is configured to be fluidically coupled to the fluid reservoir, and a second outlet port that is configured to be fluidically coupled to a sample reservoir.

The flow control mechanism defines a first lumen and a second lumen. The flow control mechanism is disposed in the diverter and is rotatable from a first configuration, in which the inlet port is placed in fluid communication with the first outlet port such that bodily-fluid can flow from the inlet port, through the first lumen and to the first outlet port, to a second configuration, in which the inlet port is placed in fluid communication with the second outlet port such that the bodily-fluid can flow from the inlet, through the second lumen and to the second outlet port.

In some embodiments, a device for procuring bodily-fluid samples from a patient includes a housing, a flow control mechanism, and an actuator. The housing has a proximal end portion and a distal end portion and defines an inner volume therebetween. The housing has an inlet port configured to be fluidically coupled to the patient and an outlet port configured to be fluidically coupled to a sample reservoir. The flow control mechanism defines a first lumen and a second lumen. The flow control mechanism is disposed in the housing and is rotatable between a first configuration, in which the inlet port is placed in fluid communication with a fluid reservoir defined, at least in part, by the housing such that bodily-fluid can flow from the inlet port, through the first lumen and to the fluid reservoir, to a second configuration, in which the inlet port is placed in fluid communication with the outlet port such that the bodily-fluid can flow from the inlet, through the second lumen and to the outlet port. The actuator is movably disposed in the housing and is operably coupled to the flow control mechanism. The actuator is configured to create a negative pressure in the fluid reservoir when actuated by the user. The actuator is further configured to rotate the flow control mechanism from the first configuration to the second configuration after a first volume of bodily-fluid is received in the fluid reservoir from the patient.

In some embodiments, a device for procuring bodily-fluid samples from a patient includes a housing, a seal member, a fluid reservoir, a flow control mechanism, and an actuator. The housing has a proximal end portion and a distal end portion and defines an inner volume therebetween. The housing has an inlet port configured to be fluidically coupled to the patient. The seal member is movably disposed in the inner volume and is configured to define, at least partially, the fluid reservoir disposed in the inner volume. The fluid reservoir is configured to receive and isolate a first volume of bodily-fluid withdrawn from the patient. The flow control mechanism is movably disposed in the housing and is configured to move between a first configuration, in which the bodily-fluid can flow from the inlet port, through the flow control mechanism and to the fluid reservoir, to a second configuration, in which the fluid reservoir is fluidically isolated from the inlet port. The actuator is operably coupled to the seal member and the flow control mechanism. The actuator includes a spring configured to move the seal member from a first position to a second position to create a negative pressure in the fluid reservoir. The actuator is configured to move the flow control mechanism from the first configuration to the second configuration after a first volume of bodily-fluid is received in the fluid reservoir from the patient.

In some embodiments, a device for procuring bodily-fluid samples from a patient includes a housing, a flow control mechanism, and an actuator. The housing has a proximal end portion and a distal end portion and defines an inner volume therebetween. The housing has an inlet port configured to be fluidically coupled to the patient and an outlet port configured to be fluidically coupled to a sample reservoir. The flow control mechanism is disposed in the housing and includes a first control member and a second control member. The second control member defines a first lumen and a second lumen and is rotatably movable between a first configuration, in which the inlet port is placed in fluid communication with a fluid reservoir defined, at least in part, by the housing such that bodily-fluid can flow from the inlet port, through the first lumen and to the fluid reservoir, to a second configuration, in which the inlet port is placed in fluid communication with the outlet port such that the bodily-fluid can flow from the inlet, through the second lumen and to the outlet port. The actuator is movably disposed in the housing and is operably coupled to the flow control mechanism. The actuator is configured to create a negative pressure in the fluid reservoir when actuated by the user. The actuator is further configured to rotate the second control member from the first configuration to the second configuration after a first volume of bodily-fluid is received in the fluid reservoir from the patient.

In some embodiments, a device for procuring bodily-fluid samples from a patient includes a diverter, a flow control mechanism, and an actuator mechanism. The diverter defines an inlet port, a first outlet port, and a second outlet port. The first outlet port is fluidically coupled to a first fluid reservoir and the second outlet port is fluidically coupled to a second reservoir, fluidically isolated from the first fluid reservoir. The flow control mechanism is configured to be disposed, at least partially within the diverter. The actuator mechanism is configured to engage the flow control mechanism to move the flow control mechanism between a first configuration, in which a flow of bodily-fluid can enter the first fluid reservoir, and a second configuration, in which a flow of bodily-fluid can enter the second fluid reservoir.

In some embodiments, a bodily-fluid transfer device can be configured to selectively divert a first, predetermined amount of a flow of a bodily-fluid to a first reservoir before permitting the flow of a second amount of the bodily-fluid into a second reservoir. In this manner, the second amount of bodily-fluid can be used for diagnostic or other testing, while the first amount of bodily-fluid, which may contain microbes from a bodily surface, is isolated from the bodily-fluid to be tested. The first amount of bodily-fluid can be subsequently used for different types of testing (e.g., CBC, other blood chemistry tests) or can be simply sequestered.

In some embodiments, a bodily-fluid transfer device is configured to automatically move from a first configuration to a second configuration, for example, without requiring an input or other action by a health care practitioner. In some embodiments, the bodily-fluid transfer device prevents bodily-fluid from flowing or otherwise being introduced into a second reservoir before at least a first amount of bodily-fluid (e.g., a predetermined amount) is first introduced into a first reservoir.

In some embodiments, a method for procuring a bodily-fluid sample using a parenteral sampling device that has a needle with a lumen and a fluid reservoir fluidically coupled to the needle includes inserting the needle of the device into a patient. The method includes establishing fluid communication between the needle and the fluid reservoir. An actuator is moved a first distance to create a negative pressure in the fluid reservoir to withdraw a predetermined volume of the bodily-fluid. The actuator is moved a second distance to engage a flow control mechanism and rotate the flow control mechanism from a first configuration to a second configuration. The first configuration is operable in allowing bodily-fluid to flow through a first flow path from the needle to the fluid reservoir and the second configuration is operable in allowing bodily-fluid to flow through a second flow path from the needle to a sample reservoir.

As used in this specification, "bodily-fluid" can include any fluid obtained from a body of a patient, including, but not limited to, blood, cerebrospinal fluid, urine, bile, lymph, saliva, synovial fluid, serous fluid, pleural fluid, amniotic fluid, and the like, or any combination thereof.

As used herein, the term "set" can refer to multiple features or a singular feature with multiple parts. For example, when referring to set of walls, the set of walls can be considered as one wall with distinct portions, or the set of walls can be considered as multiple walls. Similarly stated, a monolithically constructed item can include a set of walls. Such a set of walls can include, for example, multiple portions that are in discontinuous from each other. A set of walls can also be fabricated from multiple items that are produced separately and are later joined together (e.g., via a weld, an adhesive or any suitable method).

As used herein, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the singular forms "a," "an" and "the" include plural referents unless the context clearly dictates otherwise. Thus, for example, the term "an engagement surface" is intended to mean a single surface or multiple surfaces unless explicitly expressed otherwise.

FIG. 1 is a schematic illustration of a portion of a bodily-fluid transfer device 100, according to an embodiment. Generally, the bodily-fluid transfer device 100 (also referred to herein as "fluid transfer device" or "transfer device") is configured to permit the withdrawal of bodily-fluid from a patient such that a first portion or amount of the withdrawn fluid is diverted away from a second portion or amount of the withdrawn fluid that is to be used as a biological sample, such as for testing for the purpose of medical diagnosis and/or treatment. In other words, the transfer device 100 is configured to transfer a first, predetermined amount of a bodily-fluid to a first collection reservoir and a second amount of bodily-fluid to one or more bodily-fluid collection reservoirs fluidically isolated from the first collection reservoir, as described in more detail herein.

The transfer device 100 includes a diverter 120, a first reservoir 170, and a second reservoir 180, different from the first reservoir 170. The diverter 120 includes an inlet port 122 and two or more outlet ports, such as a first outlet port 124 and a second outlet port 126 shown in FIG. 1. The inlet port 122 is configured to be fluidically coupled to a medical device defining a pathway P for withdrawing and/or conveying the bodily-fluid from the patient to the transfer device 100. For example, the inlet port 122 can be fluidically coupled to a needle or other lumen-containing device (e.g., flexible sterile tubing). In this manner, the diverter 120 can receive the bodily-fluid from the patient via the needle or other lumen-containing device.

The first outlet port 124 of the diverter 120 is configured to be fluidically coupled to the first reservoir 170. In some embodiments, the first reservoir 170 is monolithically formed with the first outlet port 124 and/or a portion of the diverter 120. In other embodiments, the first reservoir 170 can be mechanically and fluidically coupled to the diverter 120 via an adhesive, a resistance fit, a mechanical fastener, any number of mating recesses, a threaded coupling, and/or any other suitable coupling or combination thereof. Similarly stated, the first reservoir 170 can be physically (e.g., mechanically) coupled to the diverter 120 such that an interior volume defined by the first reservoir 170 is in fluid communication with the first outlet port 120 of the diverter 120. In still other embodiments, the first reservoir 170 can be operably coupled to the first outlet port 124 of the diverter 120 via an intervening structure (not shown in FIG. 1), such as a flexible sterile tubing. More particularly, the intervening structure can define a lumen configured to place the first reservoir 170 in fluid communication with the first outlet port 124.

The first reservoir 170 is configured to receive and contain the first, predetermined amount of the bodily-fluid. In some embodiments, the first reservoir 170 is configured to contain the first amount of the bodily-fluid such that the first amount is fluidically isolated from a second amount of the bodily-fluid (different from the first amount of bodily-fluid) that is subsequently withdrawn from the patient. The first reservoir 170 can be any suitable reservoir for containing a bodily-fluid, such as a pre-sample reservoir described in detail in U.S. Pat. No. 8,197,420 ("the '420 patent"), the disclosure of which is incorporated herein by reference in its entirety. As used in this specification, the terms "first, predetermined amount" and "first amount" describe an amount of bodily-fluid configured to be received or contained by the first reservoir 170. Furthermore, while the term "first amount" does not explicitly describe a predetermined amount, it should be understood that the first amount is the first, predetermined amount unless explicitly described differently.

The second outlet port 126 of the diverter 120 is configured to be fluidically coupled to the second reservoir 180. In some embodiments, the second reservoir 180 is monolithically formed with the second outlet port 126 and/or a portion of the diverter 120. In other embodiments, the second reservoir 180 can be mechanically coupled to the second outlet port 126 of the diverter 120 or operably coupled to the second outlet port 126 via an intervening structure (not shown in FIG. 1), such as described above with reference to the first reservoir 170. The second reservoir 180 is configured to receive and contain the second amount of the bodily-fluid. For example, the second amount of bodily-fluid can be an amount withdrawn from the patient subsequent to withdrawal of the first amount. In some embodiments, the second reservoir 180 is configured to contain the second amount of the bodily-fluid such that the second amount is fluidically isolated from the first amount of the bodily-fluid.

The second reservoir 170 can be any suitable reservoir for containing a bodily-fluid, including, for example, a sample reservoir as described in the '420 patent incorporated by reference above. As used in this specification, the term "second amount" describes an amount of bodily-fluid configured to be received or contained by the second reservoir 180. In some embodiments, the second amount can be any suitable amount of bodily-fluid and need not be predetermined. In other embodiments, the second amount received and contained by the second reservoir 180 is a second predetermined amount.

In some embodiments, the first reservoir 170 and the second reservoir 180 can be coupled to (or formed with) the diverter 120 in a similar manner. In other embodiments, the first reservoir 170 and the second reservoir need not be similarly coupled to the diverter 120. For example, in some embodiments, the first reservoir 170 can be monolithically formed with the diverter 120 (e.g., the first outlet port 124)

and the second reservoir 180 can be operably coupled to the diverter 120 (e.g., the second outlet port 126) via an intervening structure, such as a flexible sterile tubing.

As shown in FIG. 1, the transfer device 100 further includes an actuator 140 and a flow control mechanism 130 defining a first channel 138 and a second channel 139. In some embodiments, the actuator 140 can be included in or otherwise operably coupled to the diverter 120. In this manner, the actuator 140 can be configured to control a movement of the flow control mechanism 130 (e.g., between a first configuration and a second configuration). For example, the actuator 140 can be movable between a first position corresponding to the first configuration of the flow control mechanism 130, and a second position, different from the first position, corresponding to the second configuration of the flow control mechanism 130. In some embodiments, the actuator 140 is configured for uni-directional movement. For example, the actuator 140 can be moved from its first position to its second position, but cannot be moved from its second position to its first position. In this manner, the flow control mechanism 130 is prevented from being moved to its second configuration before its first configuration, thus requiring that the first amount of the bodily-fluid be directed to the first reservoir 170 and not the second reservoir 180.

The flow control mechanism 130 is configured such that when in the first configuration, the first channel 138 fluidically couples the inlet port 122 to the first outlet port 124 and when in the second configuration, the second channel 139 fluidically couples the inlet portion 122 to the second outlet port 126. In some embodiments, the actuator 140 is coupled to the flow control mechanism 130 and is configured to move the flow control mechanism 130 in a translational motion between the first configuration and the second configuration. For example, in some embodiments, the flow control mechanism 130 can be in the first configuration when the flow control mechanism 130 is in a distal position relative to the transfer device 100. In such embodiments, the actuator 140 can be actuated to move the flow control device 130 in the proximal direction to a proximal position relative to the transfer device 100, thereby placing the flow control mechanism 130 in the second configuration. In other embodiments, the actuator 140 can be actuated to move the flow control mechanism 130 in a rotational motion between the first configuration and the second configuration.

Accordingly, when the flow control mechanism 130 is in the first configuration, the second outlet port 126 is fluidically isolated from the inlet port 122. Similarly, when the flow control mechanism 130 is in the second configuration, the first outlet port 124 is fluidically isolated from the inlet port 122. In this manner, the flow control mechanism 130 can direct, or divert the first amount of the bodily-fluid to the first reservoir 170 via the first outlet port 124 when the flow control mechanism 130 is in the first configuration and can direct, or divert the second amount of the bodily-fluid to the second reservoir 180 via the second outlet port 126 when the flow control mechanism 130 is in the second configuration.

In some embodiments, at least a portion of the actuator 140 can be operably coupled to the first reservoir 170. In this manner, the actuator 140 (or at least the portion of the actuator 140) can be configured to cause a vacuum within the first reservoir 170, thereby initiating flow of the bodily-fluid through the transfer device 100 and into the first reservoir 170 when the diverter 120 is in its first configuration. The actuator 140 can include any suitable mechanism for actuating the transfer device 100 (e.g., at least the flow control mechanism 130), such as, for example, a rotating disc, a plunger, a slide, a dial, a button, and/or any other suitable mechanism or combination thereof. Examples of suitable actuators are described in more detail herein with reference to specific embodiments.

In some embodiments, the diverter 120 is configured such that the first amount of bodily-fluid need be conveyed to the first reservoir 170 before the diverter 120 will permit the flow of the second amount of bodily-fluid to be conveyed through the diverter 120 to the second reservoir 180. In this manner, the diverter 120 can be characterized as requiring compliance by a health care practitioner regarding the collection of the first, predetermined amount (e.g., a pre-sample) prior to a collection of the second amount (e.g., a sample) of bodily-fluid. Similarly stated, the diverter 120 can be configured to prevent a health care practitioner from collecting the second amount, or the sample, of bodily-fluid into the second reservoir 180 without first diverting the first amount, or pre-sample, of bodily-fluid to the first reservoir 170. In this manner, the health care practitioner is prevented from including (whether intentionally or unintentionally) the first amount of bodily-fluid, which is more likely to contain bodily surface microbes and/or other undesirable external contaminants that are not representative of the in vivo conditions of a patient's bodily-fluid system, in the bodily-fluid sample to be used for analysis. The forced-compliance aspect of the diverter 120 is described in more detail herein with reference to specific embodiments.

In some embodiments, the diverter 120 is configured to automatically (i.e., without requiring an input or other action by a health care practitioner or other operator of the transfer device 100) fluidically isolate the inlet port 122 from the first outlet port 124. For example, the diverter 120 can be configured such that the flow control mechanism 130 will automatically fluidically isolate the first outlet port 124 from the inlet port 122 when the first reservoir 170 has received the first, predetermined amount of bodily-fluid. As such, additional flow of bodily-fluid in excess of the first amount into the first reservoir 170 is prevented. In some embodiments, the diverter 120 is configured such that the flow control mechanism 130 automatically moves from its first configuration to its second configuration after the first amount of bodily-fluid is conveyed to the first reservoir 170.

In some embodiments, the actuator 140 can have a third position, different from the first and second positions, which corresponds to a third configuration of the flow control mechanism 130. When in the third configuration, the flow control mechanism 130 can fluidically isolate the inlet port 122 from both the first outlet port 124 and the second outlet port 126 simultaneously. Therefore, when the flow control mechanism 130 is in its third configuration, flow of bodily-fluid from the inlet port 122 to either the first reservoir 170 or the second reservoir 180 is prevented. In use, for example, the actuator 140 can be actuated to place the flow control mechanism 130 in the first configuration such that a bodily-fluid can flow from the inlet port 122 to the first reservoir 170, then moved to the second configuration such that the bodily-fluid can flow from the inlet port 122 to the second reservoir 180, then moved to the third configuration to stop the flow of bodily-fluid into and/or through the diverter 120. In some embodiments, the flow control mechanism 130 can be moved to the third configuration between the first configuration and the second configuration. In some embodiments, the flow control mechanism 130 can be in the third configuration before being moved to either of the first configuration or the second configuration.

In some embodiments, one or more portions of the transfer device 100 are disposed within a housing (not shown in FIG. 1). For example, in some embodiments, at least a portion of one or more of the diverter 120, the first reservoir 170, and the actuator 140 can be disposed within the housing. In such an embodiment, at least a portion of the actuator 140 is accessible through the housing. Examples of suitable housings are described in more detail herein with reference to specific embodiments.

Referring now to FIGS. 2-12, a transfer device 200 includes a housing 201, a diverter 220, a flow control mechanism 230, and an actuator 240. The transfer device 200 can be any suitable shape, size, or configuration. For example, while shown in FIGS. 2 and 3 as being substantially cylindrical, the transfer device 200 can be square, rectangular, polygonal, and/or any other non-cylindrical shape.

Figure 4:
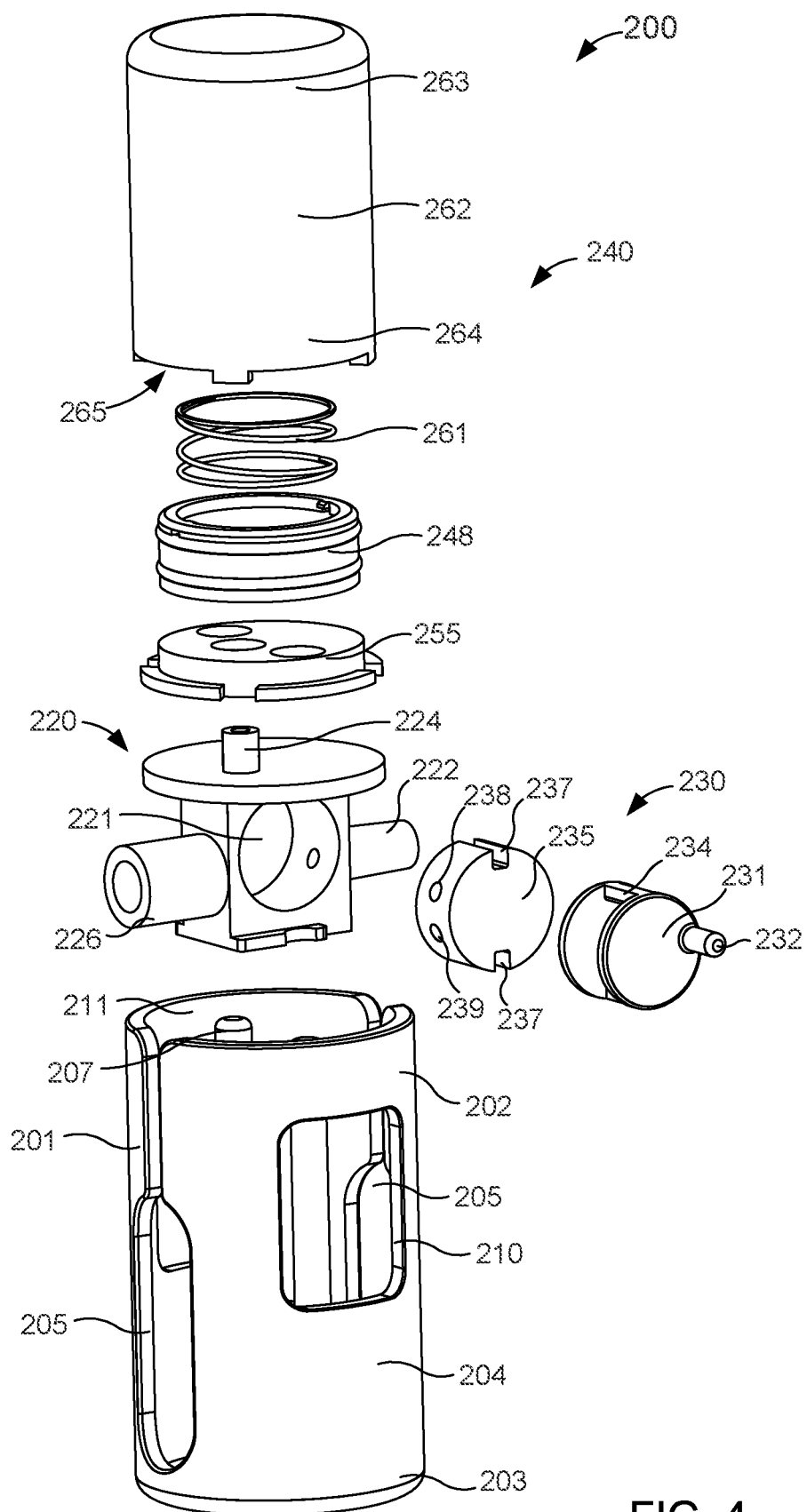
FIG. 4 is an exploded view of the bodily-fluid transfer device of FIG. 2.

The housing 201 includes a proximal end portion 202 and a distal end portion 203. The distal end portion 203 includes a base 206 from which a set of walls 204 extend. More specifically, the walls 204 of the housing 201 define a substantially annular shape and define an inner volume 211 therebetween. The proximal end portion 202 of the housing 201 is configured to be open such that the inner volume 211 can receive at least a portion of the diverter 220, a portion of the flow control mechanism 230, and a portion of the actuator 240 (FIG. 4). Similarly stated, the housing 201 is configured to house at least the portion of the diverter 220, the portion of the flow control mechanism 230, and the portion of the actuator 240

The walls 204 of the housing 201 define a set of status windows 210 and a set of channels 205. The status windows 210 can be any suitable shape or size and are configured to allow a user to visually inspect at least a portion of the transfer device 200. While shown in FIG. 5 as including two status windows 210, in other embodiments, the housing 201 can define any number of status windows 210, such as, for example, one, three, four, or more. The channels 205 defined by the housing 201 are configured to extend from the distal end portion 203 and through the proximal end portion 202. Similarly stated, the channels 205 extend through a proximal surface of the housing 201. Said yet another way, the channels 205 are open ended at the proximal end portion 202 of the housing 201.

Figure 5:
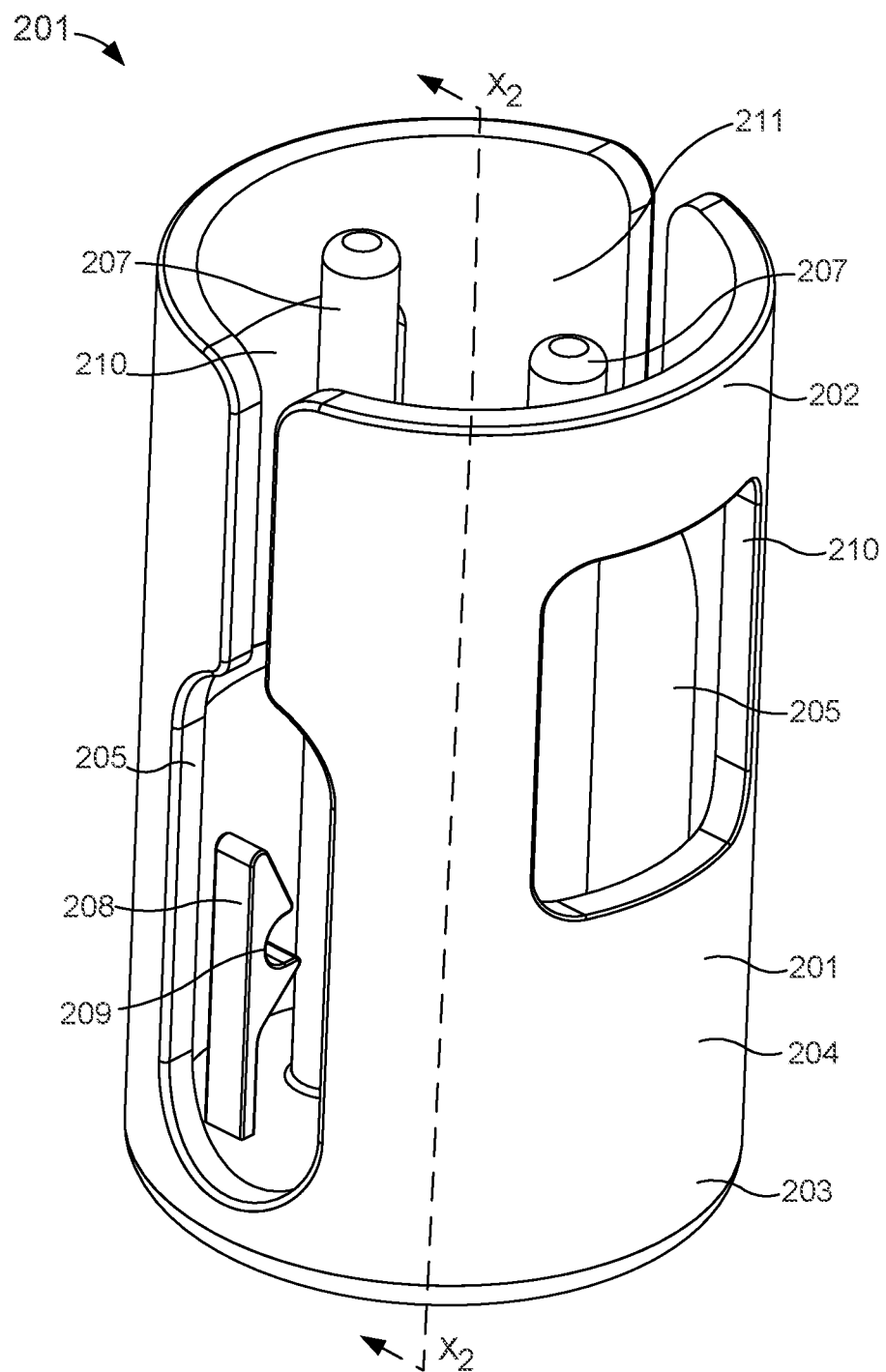
FIG. 5 is a perspective view of a housing included in the bodily-fluid transfer device illustrated in FIG. 2.
Figure 6:
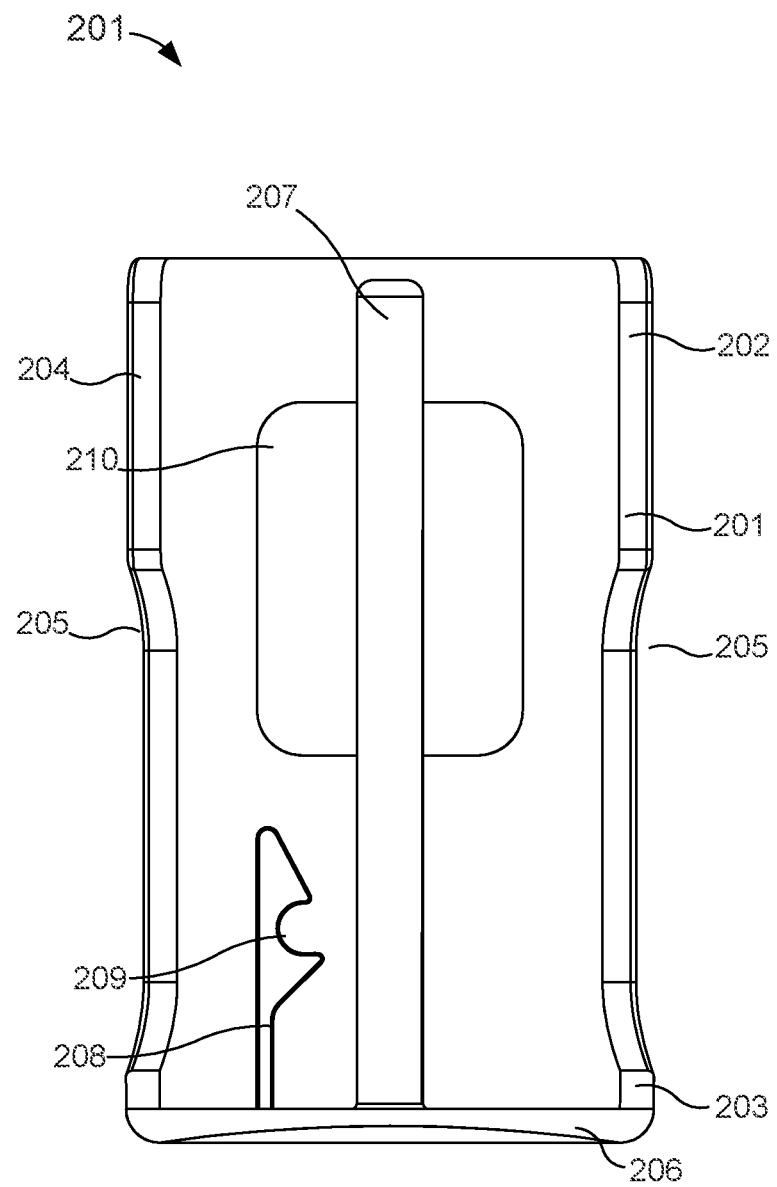
FIG. 6 is a cross-sectional view of the housing illustrated in FIG. 5 taken along the line $X_2$-$X_2$.

The housing 201 further includes a set of guide posts 207 and a set of flow control protrusions 208. While shown in FIGS. 5 and 6 as cylindrical protrusions, the guide posts 207 can be any suitable shape or size and are configured to extend from the base 206 in the proximal direction. In this manner, the guide posts 207 are configured to engage a portion of the diverter 220 and a portion of the actuator 240, as further described herein. The flow control protrusions 208 extend from the base 206 in the proximal direction and define notches 209. In this manner, the flow control protrusions 208 are configured to selectively engage the flow control mechanism 230 to move the flow control mechanism 230 between a first configuration and a second configuration, as described in further detail herein. While only one flow control protrusion 208 is shown in FIGS. 5 and 6, the housing 201 is configured to include two flow control protrusions 208. In other embodiments, the housing 201 can include any number flow control protrusions 208 such as for example, one, three, four, or more.

Figure 2:
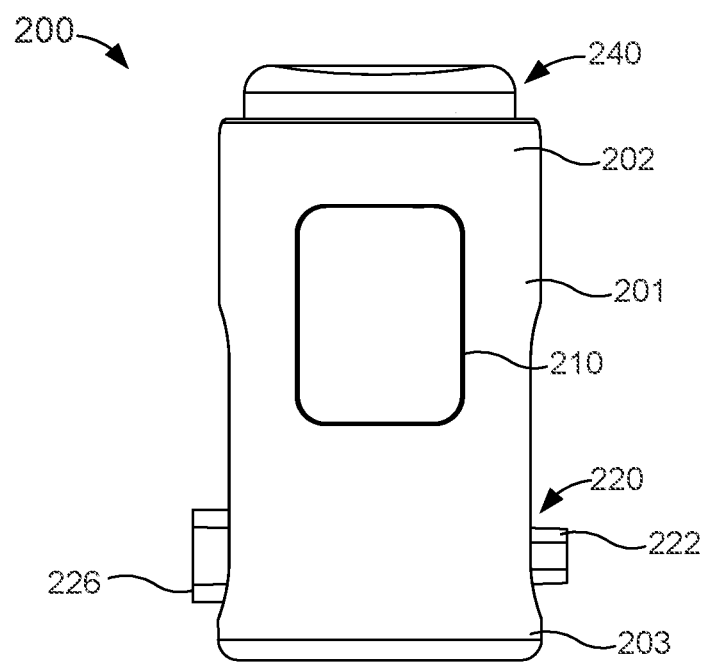
FIG. 2 is a front view of a bodily-fluid transfer device according to an embodiment.
Figure 3:
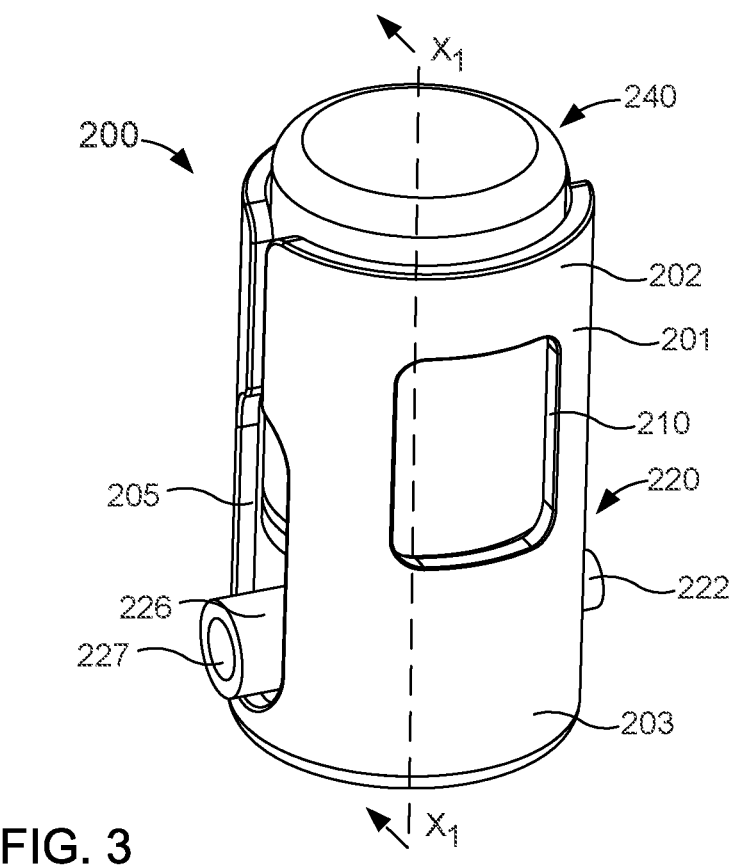
FIG. 3 is a perspective view of the bodily-fluid transfer device of FIG. 2.
Figure 7:
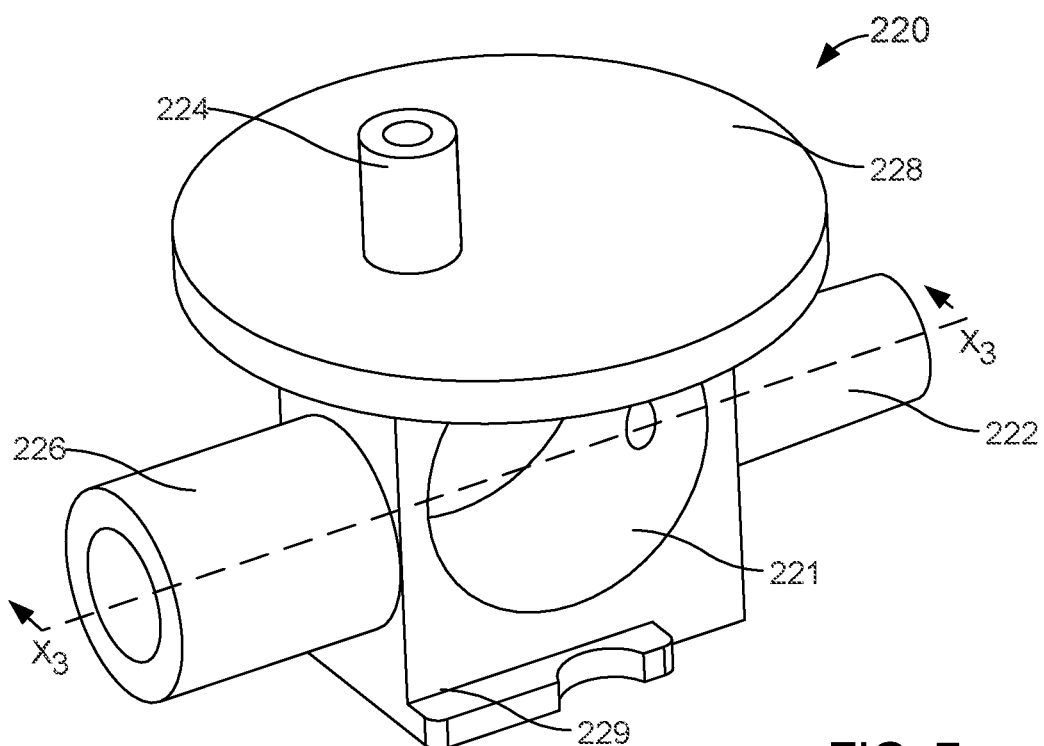
FIG. 7 is a perspective view of a diverter included in the bodily-fluid transfer device of FIG. 2.
Figure 8:
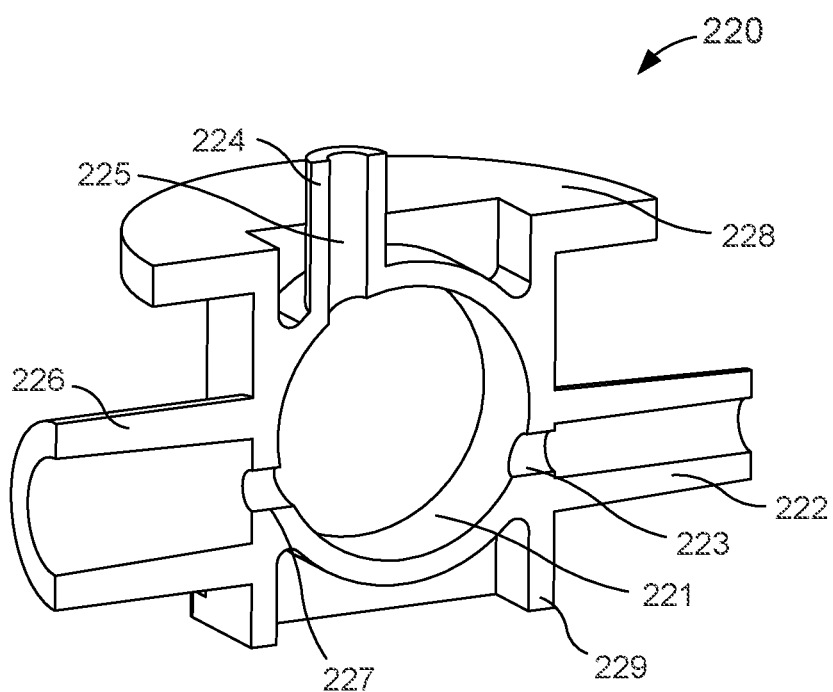
FIG. 8 is a cross-sectional view of the diverter illustrated in FIG. 8 taken along the line $X_3$-$X_3$.

As shown in FIGS. 7 and 8, the diverter 220 includes a proximal end portion 228 and a distal end portion 229 and defines an inner volume 221. The inner volume 221 is configured to receive at least a portion of the flow control mechanism 230, as further described herein. The proximal end portion 228 of the diverter 220 includes a first outlet port 224 and can engage a portion of the actuator 240. The distal end portion 229 includes an inlet port 222 and a second outlet port 226. As shown in FIGS. 1 and 2, the diverter 220 is disposed within the inner volume 211 of the housing 201 such that a portion of the inlet port 222 extends through a first channel 205 defined by the walls 204 of the housing 201 and a portion of the second outlet port 226 extends through a second channel 205 opposite the first channel. While not explicitly shown in FIGS. 2-12, the distal end portion 229 of the diverter 220 is configured to engage the guide posts 207 such that lateral movement of the diverter 220 is limited. Similarly stated, the distal end portion 229 of the diverter 220 can engage the guide posts 207 of the housing 201 such that the diverter 220 is substantially limited to movement in the proximal or distal direction, relative to the housing 201, as further described herein.

The inlet port 222 included in the distal end portion 229 of the diverter 220 defines an inlet lumen 223. As shown in FIG. 8, the inlet lumen 223 is configured to be in fluid communication with the inner volume 221. Similarly stated, the inlet lumen 223 of the inlet port 222 extends through a wall defining the inner volume 221 of the diverter 220. The inlet port 222 is further configured to be fluidically coupled to a medical device (not shown) defining a fluid flow pathway for withdrawing and/or conveying the bodily-fluid from a patient to the transfer device 200. For example, the inlet port 222 can be fluidically coupled to a needle or other lumen-containing device (e.g., flexible sterile tubing). Similarly stated, the inlet lumen 223 defined by the inlet port 222 is placed in fluid communication with a lumen defined by a lumen-containing device, when the lumen-containing device is coupled to the inlet port 222. Expanding further, when the lumen-containing device is disposed within a portion of a body of the patient (e.g., within a vein of the patient), the inner volume 221 of the diverter 220 is placed in fluid communication with the portion of the body of the patient.

The first outlet port 224 included in the proximal end portion 228 of the diverter 220 defines a first outlet lumen 225. As shown in FIG. 8, the first outlet lumen 225 is configured to be in fluid communication with the inner volume 221 of the diverter 220 (e.g., the first outlet lumen 225 extends through the wall defining the inner volume 221). Similarly, the second outlet port 226 included in the distal end portion 229 of the diverter 220 defines a second outlet lumen 227 in fluid communication with the inner volume 221.

Figure 9:
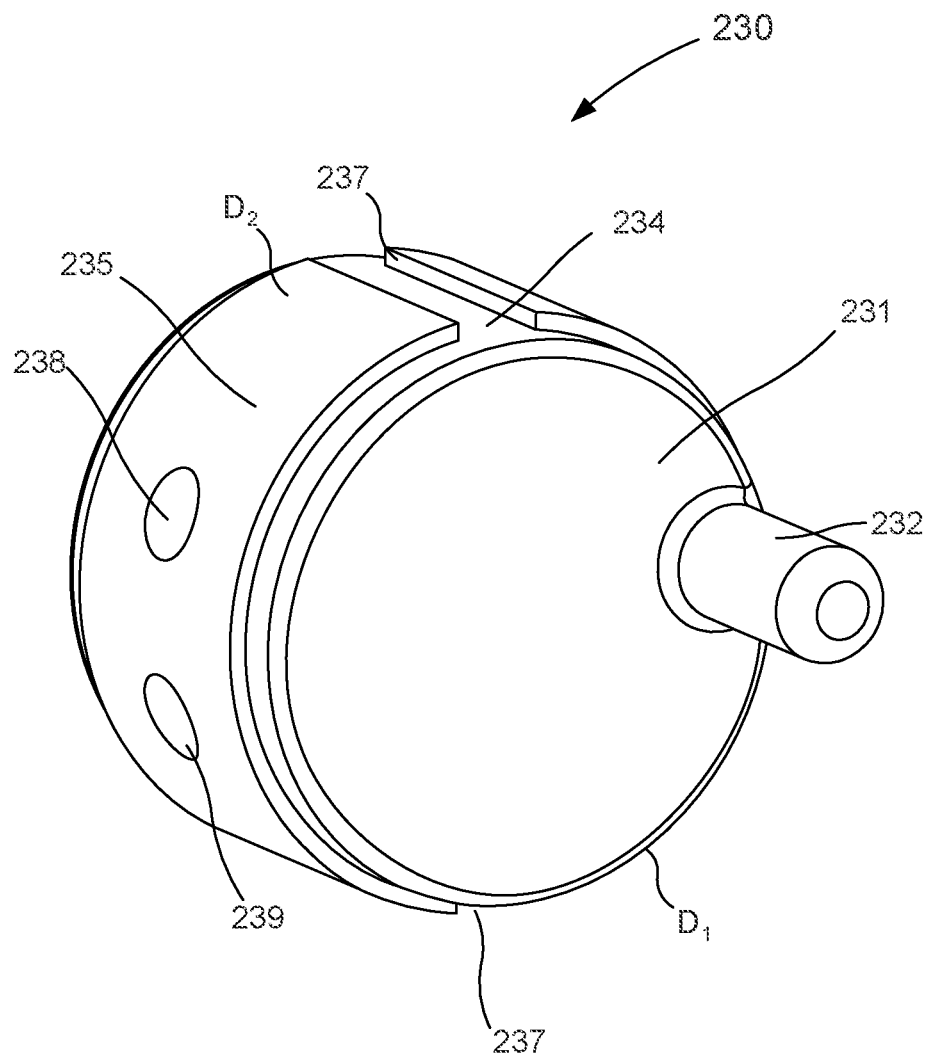
FIG. 9 is a perspective view of a flow control mechanism included in the bodily-fluid transfer device of FIG. 2.

As shown in FIG. 9, the flow control mechanism 230 includes a first control member 231 and a second control member 235. At least a portion of the flow control mechanism 230 is configured to be disposed within the inner volume 221 defined by the diverter 220. In this manner, the flow control mechanism 230 defines a circular cross-sectional shape such that when the flow control mechanism 230 is disposed within the inner volume 221, a portion of the flow control mechanism 230 forms a friction fit with the walls of the diverter 220 defining the inner volume 221, as described in further detail herein.

The first control member 231 includes a set of activation protrusions 232 and a set of cross members 234 (only one of each is shown in FIG. 9). The activation protrusions 232 are configured to engage the flow control protrusion 208 of the housing 201. More specifically, the activation protrusions 232 can be disposed within the notch 209 defined by the flow control protrusion 208. Therefore, in use, the flow control protrusions 208 can engage the activation protrusions 232 to move the flow control mechanism 230 between a first configuration and a second configuration.

The second control member 235 defines a first lumen 238, a second lumen 239, and a set of channels 237 and is configured to be disposed, at least partially, within the first control member 231. More particularly, the first control member 231 has a first diameter $D_1$ and the second control member 235 has a second diameter $D_2$ larger than the first diameter $D_1$. Therefore, when the second control member 235 is disposed within the first control member 231 a portion of the second control member 235 extends beyond a surface of the first control member 231 that defines the first diameter $D_1$.

The channels 237 defined by the second control member 235 receive the cross members 234 of the first control member 231. The arrangement of the cross members 234 disposed within the channels 237 is such that the second control member 235 is maintained in a desired position relative to the first control member 231. In this manner, the second control member 235 is configured to move concurrently with the first control member 231 when the flow control protrusions 208 engage the activation protrusions 232 of the first control member 231. Similarly stated, the flow control mechanism 230 is moved between the first configuration and the second configuration when the first control member 231 and the second control member 235 are moved between the first configuration and the second configuration, respectively. Furthermore, when the flow control mechanism 230 is in the first configuration, the first lumen 238 is placed in fluid communication with the inlet lumen 223 defined by the inlet port 222 and the first outlet lumen 225 defined by the first outlet port 224. When the flow control mechanism 230 is in the second configuration, the second lumen 239 is placed in fluid communication with the inlet lumen 223 defined by the inlet port 222 and the second outlet lumen 227 defined by the second outlet port 226, as described in further detail herein.

Figure 10:
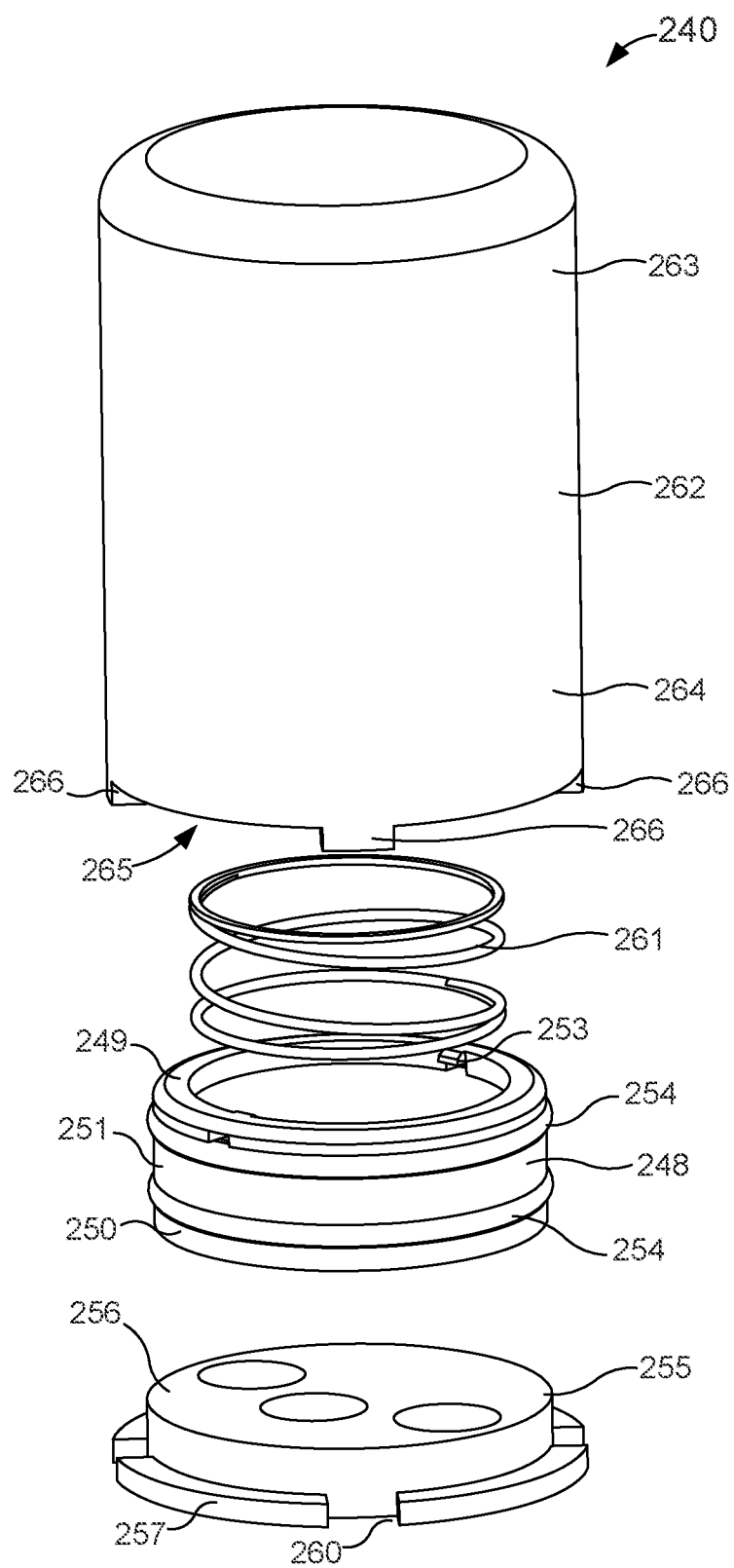
FIG. 10 is an exploded view of an actuator mechanism included in the bodily-fluid transfer device of FIG. 2.

As shown in FIG. 10, the actuator mechanism 240 includes an actuator housing 262, a plunger 248, a cap 255, and a spring 261. The actuator mechanism 240 is configured to move between a first configuration and a second configuration, thereby moving the transfer device 200 between a first configuration and a second configuration, as described in further detail herein. The actuator housing 262 includes a proximal end portion 263 and a distal end portion 264 and defines an inner volume 265. The actuator housing 262 can be any suitable shape, size or configuration. For example, the actuator housing 262 can be substantially cylindrical and be configured to be disposed, at least partially, within the housing 201. The inner volume 265 is configured to receive the plunger 248, the spring 261, and at least a portion of the cap 255. The plunger 248 includes a proximal end portion 249 and a distal end portion 249 and a side wall 251. The distal end portion 250 is configured to receive the guide posts 207 of the housing 201, as described in further detail herein. The proximal end portion 249 includes a set of retention tabs 253 and can receive a portion of the spring 261. More particularly, the retention tabs 253 included in the proximal end portion 249 of the plunger 248 are configured to engage the spring 261 to removably couple the spring 261 to the plunger 248.

The side wall 251 of the plunger 248 define a set of notches 252 configured to receive a set of seal members 254. The seal members 254 can be any suitable seal members 254 such as for example, o-rings formed from any suitable elastomeric material. In this manner, the plunger 248 is disposed within the inner volume 265 of the actuator housing 262 such that the seal members 254 define a friction fit with the inner walls (not shown in FIG. 10) that define the inner volume 265 of the actuator housing 262. Similarly stated, the seal members 254 define a fluidic seal with the inner walls of the actuator housing 262. Furthermore, the plunger 248 is disposed within the inner volume 265 such that the plunger 248 divides the inner volume 265 into a first portion 267 that is fluidically isolated from a second portion 270 (see e.g., FIGS. 11 and 12). The first portion 267 of the inner volume 265 is defined between a surface of the proximal end portion 263 of the actuator housing 262 and the proximal end portion 249 of the plunger 248. As such, the first portion 267 of the inner volume 265 is configured contain the spring 261 such that the spring 261 is in contact with the surface of the proximal end portion 263 of the actuator housing 262 and the proximal end portion 249 of the plunger 248.

The cap 255 can be any suitable shape or size and is configured to be disposed, at least partially, within the inner volume 265 of the actuator housing 262. Furthermore, the cap 255 can be formed from any suitable material. For example, in some embodiments, the cap 255 is formed from an elastomeric material such as silicone. In other embodiments, the cap 255 can be formed from any polymeric material such as, for example, rubber, vinyl, neoprene, or the like.

The cap 255 includes a proximal end portion 256 and a distal end portion 257. The proximal end portion 256 is disposed within the inner volume 265 of the actuator housing 262 such that the distal end portion 250 of the plunger 248 and the proximal end portion 256 of the cap defines the second portion 270 of the inner volume (referred to henceforth as "first reservoir") of the inner volume 265. Expanding further, the proximal end portion 256 of the cap 255 is configured to define a friction fit with the inner walls (not shown in FIG. 10) that define the inner volume 265. Similarly stated, the proximal end portion 254 defines a fluidic seal with the inner walls of the actuator housing 262. Therefore, the fluidic seal defined by the actuator housing 262 and the plunger 248 and the fluidic seal defined by the actuator housing 262 and the proximal end portion 256 of the cap 255 fluidically isolate the fluid reservoir 270 from a portion outside of the fluid reservoir 270 (i.e., the second portion of the inner volume 265).

The distal end portion 257 of the cap 255 includes a set of notches 260 configured to receive a set of protrusions 266 of the actuator housing 262 when the proximal end portion 256 is disposed within the inner volume 265. The arrangement of the notches 260 defined by the cap 255 and the protrusions 266 of the actuator housing 262 is such that the protrusions 266 form a friction fit with the walls defining the notches 260. In this manner, the protrusions 266 engage the walls defining the notches 260 to maintain the cap 255 in a desired position relative to the actuator housing 262 when the proximal end portion 256 is disposed within the inner volume 265. Moreover, the actuator mechanism 240 and the diverter 220 are disposed within the housing 201 such that the distal end portion 257 of the cap 255 is in contact with the proximal end portion 228 of the diverter 220, as described in further detail herein.

The cap 255 further defines an inlet port 258 and a set of guide post ports 259. The inlet port 258 is configured to receive a portion of the first outlet port 224 included in the diverter 220. More specifically, the inlet port 258 receives the first outlet port 224 such that the inlet port 258 form a fluidic seal with an outer surface of the first outlet port 224. Similarly, the guide post ports 259 receive a portion of the guide posts 207 of the housing 201 such that the guide post ports 259 form a fluidic seal with an outer surface of the guide posts 207. In this manner, a portion of the guide posts 207 and a portion of the first outlet port 224 are disposed within the fluid reservoir 270 defined by the actuator housing 262. Furthermore, with the portion of the first outlet port 224 disposed within the fluid reservoir 270, the fluid reservoir 270 (i.e., the second portion of the inner volume 265) is in fluid communication with the first outlet lumen 225, as described in further detail herein.

In some embodiments, the transfer device 200 can be stored in a storage configuration in which the second control member 235 of the flow control mechanism 230 fluidically isolates the inlet port 222, the first outlet port 224, and the second outlet port 226 from the inner volume 221 defined by the diverter 220. In such embodiments, first lumen 238 and the second lumen 239 are fluidically isolated from the inlet lumen 223, the first outlet lumen 225, and the second outlet lumen 227. Furthermore, the friction fit defined by the second control member 235 and the walls of the diverter 220 defining the inner volume 221 maintain the flow control mechanism 230 in the storage configuration until the flow control mechanism 230 is moved from the storage configuration.

In use, a user can engage the transfer device 200 to couple the inlet port 222 to a proximal end portion of a lumen-defining device (not shown) such as, for example, a butterfly needle or, as an additional example, surgical tubing coupleable with a Luer-Lok-type connection that allows for mating to an indwelling catheter or hub or other general vascular access device(s)/product(s). With the inlet port 222 coupled to the lumen-defining device the inlet lumen 223 is placed in fluid communication with the lumen defined by the lumen-defining device. Furthermore, the distal end portion of the lumen-defining device can be disposed within a portion of the body of a patient (e.g., a vein), thus, the inlet lumen 223 is in fluid communication with the portion of the body of the patient. In a similar manner, the second outlet port 226 can be coupled to an external fluid reservoir (not shown). The external fluid reservoir can be any suitable reservoir. For example, in some embodiments, the external fluid reservoir can be a BacT/ALERT® SN or a BacT/ALERT® FA, manufactured by BIOMERIEUX, INC.

Figure 11:
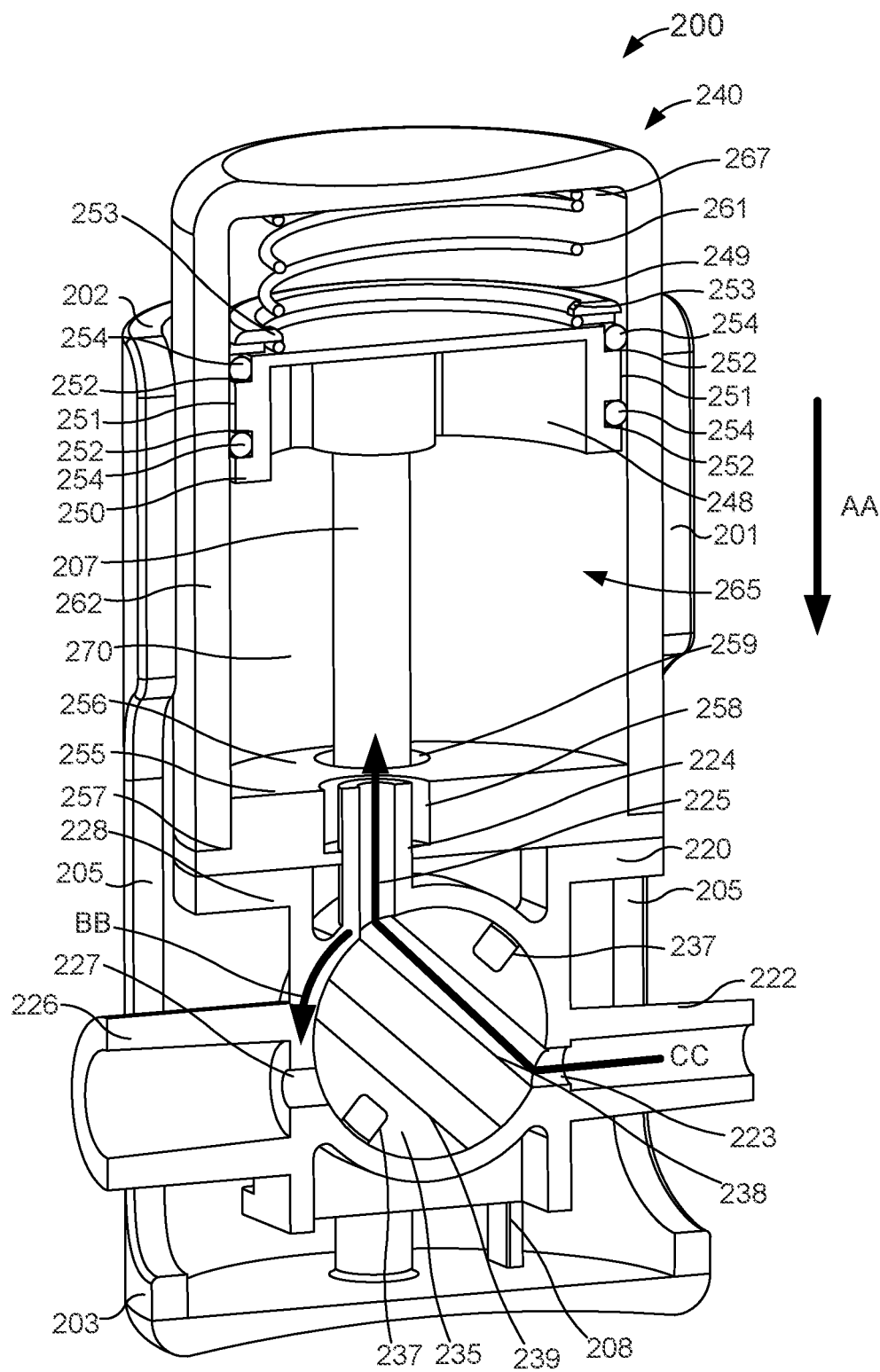
FIG. 11 is a cross-sectional view of the bodily-fluid transfer device of FIG. 2 taken along the line $X_1$-$X_1$, in a first configuration.

With the inlet port 222 coupled to the lumen-defining device and the second outlet port 226 coupled to the external fluid reservoir, a user can place the transfer device 200 in the first configuration by applying an activation force to the actuator mechanism 240, thereby moving at least a portion of the actuator mechanism 240, the diverter 220, and the flow control mechanism 230 in the distal direction towards the first configuration, as shown by the arrow AA in FIG. 11. More specifically and as described above, the distal end portion 250 of the plunger 248 engages the guide posts 207 of the housing 201. The arrangement of the plunger 248 and the guide posts 207 is such that as the user applies the activation force to the actuator mechanism 240, the position of the plunger 248, relative to the housing 201, is maintained. Therefore, the activation force applied by the user moves the actuator housing 262, the cap 255, the diverter 220, and the flow control mechanism 230 in the direction of the arrow AA, but not the plunger 248. Thus, the distal movement of the actuator housing 262 is such that a portion of the activation force is configured to compress the spring 261, and as such, the height of the second portion 267 of the inner volume is reduced. The compression of the spring 261 is such that the spring 261 exerts a reaction force (e.g., a force of expansion) in response to the portion of the activation force compressing the spring 261. Similarly stated, the spring 261 is configured return to an expanded configuration when the activation force is removed.

The distal movement of the actuator housing 262 relative to the plunger 248 is such that the height of the fluid reservoir 270 is increased. With the fluid reservoir 270 being fluidically isolated (as described above) the increase in the height (i.e., the increase in volume) produces a negative pressure within the fluid reservoir 270. Furthermore, as the actuator mechanism 240 is moved from the storage configuration toward the first configuration, the flow control protrusions 208 engage the activation protrusions 232 (not shown in FIG. 11) included in the first control member 231 to move the flow control mechanism 230 toward the first configuration, as indicated by the arrow BB. Thus, when the flow control mechanism 230 is moved to the first configuration, the first lumen 238 defined by the second control member 235 is placed in fluid communication with the inlet lumen 223 defined by the inlet port 222 and the first outlet lumen 225 defined by the first outlet port 224.

As shown by the arrow CC, the inlet lumen 223 of the inlet port 222, the first lumen 238 of the second control member 235, and the first outlet lumen 225 of the first outlet port 224 define a fluid flow path such that the fluid reservoir 270 defined by the actuator housing 262 is in fluid communication with the inlet port 222. Furthermore, with the inlet port 222 coupled to the lumen-defining device the fluid reservoir 270 of the actuator housing 262 is placed in fluid communication with the portion of the patient (e.g., the vein). The negative pressure within the fluid reservoir 270 is such that the negative pressure differential introduces a suction force within the portion of the patient. In this manner, a bodily-fluid is drawn into the fluid reservoir 270 of the actuator housing 262. In some embodiments, the bodily-fluid can contain undesirable microbes such as, for example, dermally-residing microbes.

In some embodiments, the magnitude of the suction force can be modulated by increasing or decreasing the amount of activation force applied to the actuator mechanism 240. Excess suction force can, in some cases, collapse a patient's vein thereby cutting off sample flow. Once a vein is collapsed, one or more additional venipunctures may be required to access a non-collapsed vein. Excess suction force may also cause hemolysis at the needle tip within the vein due to excessive negative pressure. Thus, in some embodiments, it can be desirable to limit the amount of suction force (i.e., modulate the negative pressure during a blood draw) introduced to a vein to reduce, minimize, or even eliminate vein collapse and/or one potential source of hemolysis. In such embodiments, the user can reduce the amount of force applied to the actuator mechanism 240. In this manner, the reaction force exerted by the expansion of the spring 261 (e.g., as described above) is sufficient to overcome a portion of the activation force applied by the user. Thus, the spring 261 can expand to move the plunger 248 and the housing 201 in the distal direction, relative to the actuator housing 262, the cap 255, the diverter 220, and the flow control mechanism 230. The distal movement of the plunger 248 and housing 201 is such that the flow control protrusions 208 engage the activation protrusions 232 of the flow control mechanism 230 to move the flow control mechanism 230 towards the storage configuration. The rotation of the flow control mechanism 230 (e.g., in a direction opposite the arrow BB) reduces the size of the fluid pathway (e.g., an inner diameter) between the inlet lumen 223 and the first lumen 238 and the first outlet port 225 and the first lumen 238, thereby reducing the suction force introduced into the vein of the patient.

With the desired amount of bodily-fluid transferred to the fluid reservoir 270 defined by the actuator housing 262, a user can engage the transfer device 200 to move the transfer device 200 from the first configuration to the second configuration, wherein a flow of bodily-fluid is transferred to the external reservoir (e.g., such as those described above). In some embodiments, the desired amount of bodily-fluid transferred to the actuator housing 262 is a predetermined amount of fluid. For example, in some embodiments, the transfer device 200 can be configured to transfer bodily-fluid until the pressure within the fluid reservoir 270 defined by the actuator housing 262 is in equilibrium with the pressure of the portion of the body in which the lumen-defining device is disposed (e.g., the vein). In such embodiments, the equalizing of the pressure between the second portion 176 of the inner volume 265 and the portion of the body stops the flow of the bodily-fluid into the actuator housing 262. In some embodiments, the predetermined amount of bodily-fluid (e.g., volume) is at least equal to the combined volume of the inlet lumen 223, the first lumen 238, the first outlet lumen 225, and the lumen-defining device.

Figure 12:
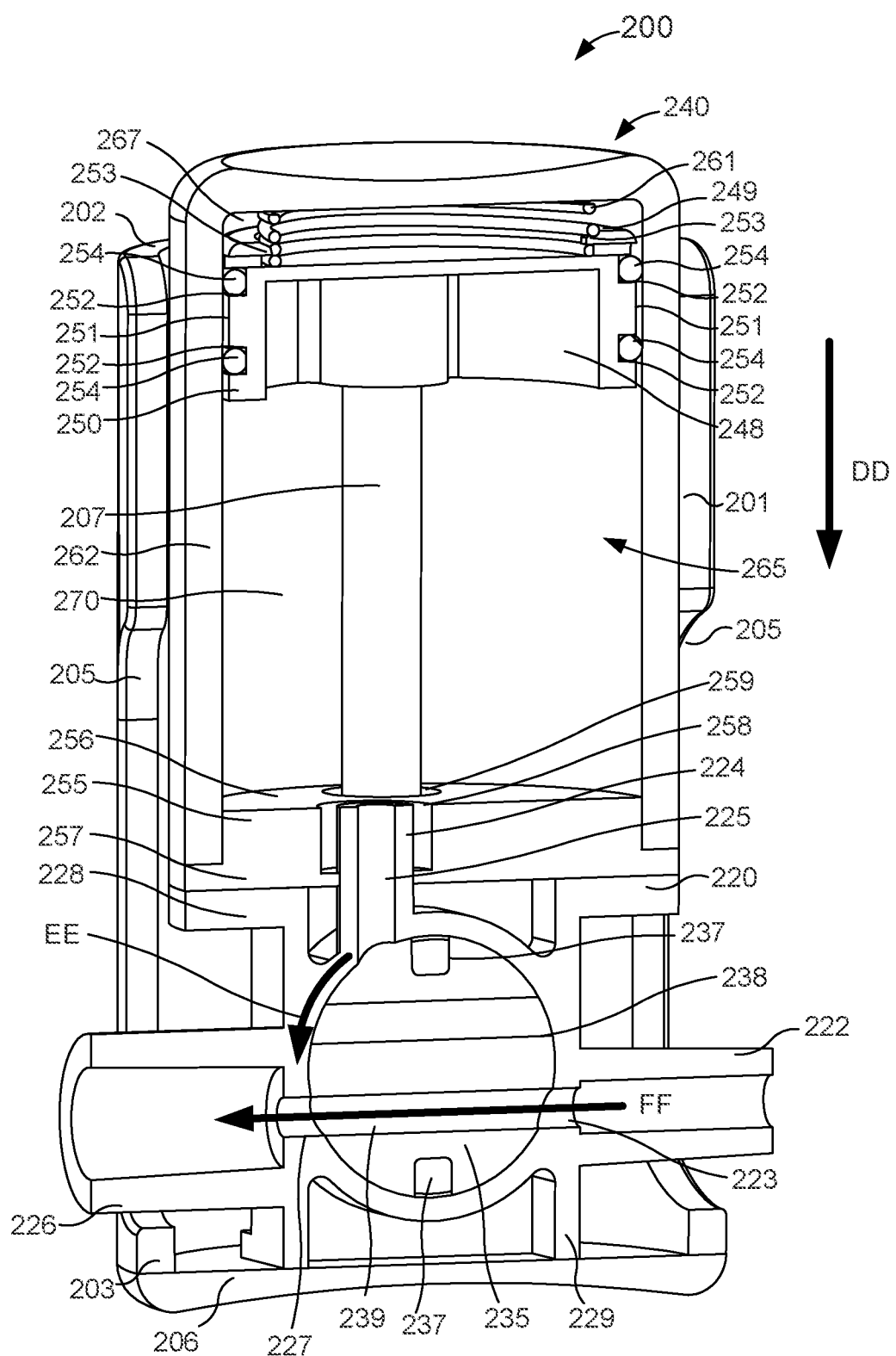
FIG. 12 is a cross-sectional view of the bodily-fluid transfer device of FIG. 2 taken along the line $X_1$-$X_1$, in a second configuration.

As shown in FIG. 12, the transfer device 200 can be moved from the first configuration to the second configuration by further moving the actuator mechanism 240 in the distal direction, as indicated by the arrow DD. Expanding further, the user can apply an activation force to the actuator mechanism 240 such that the actuator housing 262, the cap 255, the diverter 220, and the flow control mechanism 230 move in the distal direction. With the desired amount of the bodily-fluid disposed within the fluid reservoir 270 the volume of the fluid reservoir 270 is configured to remain constant as the actuator housing 262 and the cap 255 move relative to the plunger 248. Similarly stated, the pressure of the fluid reservoir 270 is configured to remain substantially unchanged as the transfer device 200 is moved from the first configuration to the second configuration.

As the actuator mechanism 240 is moved from the first configuration toward the second configuration, the flow control protrusions 208 engage the activation protrusions 232 (not shown in FIG. 12) included in the first control member 231 to move the flow control mechanism 230 toward the second configuration, as indicated by the arrow EE. Thus, when the flow control mechanism 230 is moved to the second configuration, the second lumen 239 defined by the second control member 235 is placed in fluid communication with the inlet lumen 223 defined by the inlet port 222 and the second outlet lumen 227 defined by the second outlet port 226.

As shown by the arrow FF, the inlet lumen 223 of the inlet port 222, the second lumen 239 of the second control member 235, and the second outlet lumen 227 of the second outlet port 226 define a fluid flow path such that the external reservoir (not shown in FIG. 12) is in fluid communication with the inlet port 222 and, therefore, the portion of the patient (e.g., the vein). Furthermore, the external reservoir is configured to define a negative pressure (e.g., the known external reservoirs referred to herein are vessels defining a negative pressure). The negative pressure within the external reservoir is such that the negative pressure differential between the external reservoir and the portion of the body of the patient introduces a suction force within the portion of the patient. Therefore, a desired amount of bodily-fluid is drawn into the external reservoir and is fluidically isolated from the first, predetermined amount of bodily-fluid contained within the fluid reservoir 270 defined by the actuator housing 262. In this manner, the bodily-fluid contained in the external reservoir is substantially free from microbes generally found outside of the portion of the patient (e.g., dermally residing microbes, microbes within a lumen defined by the transfer device 200, microbes within the lumen defined by the lumen defining device, and/or any other undesirable microbe(s)). With the desired amount of bodily-fluid contained in the external fluid reservoir, the user can remove the activation force from the actuator mechanism 240 (e.g., remove the portion of the hand engaging the actuator mechanism 240). With the removal of the activation force, the spring 261 exerts the force of expansion (described above) to move the transfer device 200 from the second configuration to the storage configuration. With the transfer device 200 in the storage configuration, the first outlet port 224 is fluidically isolated from the first lumen 238 and/or the second lumen 239 of the flow control mechanism 230. Thus, the bodily-fluid contained within the actuator housing 262 is fluidically isolated from a volume outside the actuator housing 262 and the external reservoir can be decoupled from the transfer device 200. In addition, the bodily-fluid contained within the actuator housing 262 is isolated from the patient and the healthcare worker, and can be safely disposed of (e.g., in a biohazard materials container) in a "closed" device.

Figure 13:
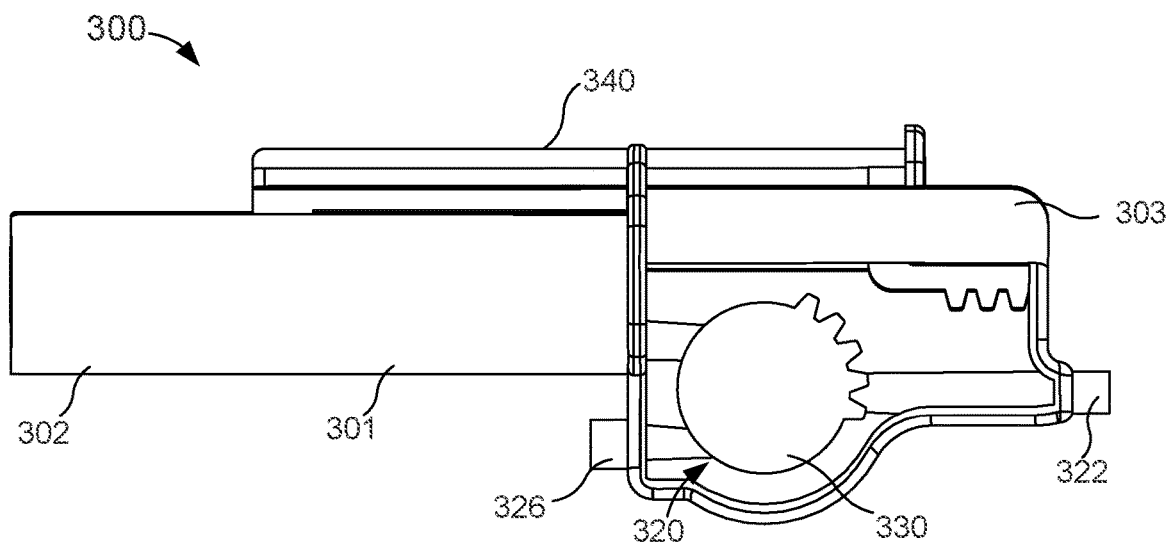
FIG. 13 is a front view of a bodily-fluid transfer device according to an embodiment.
Figure 14:
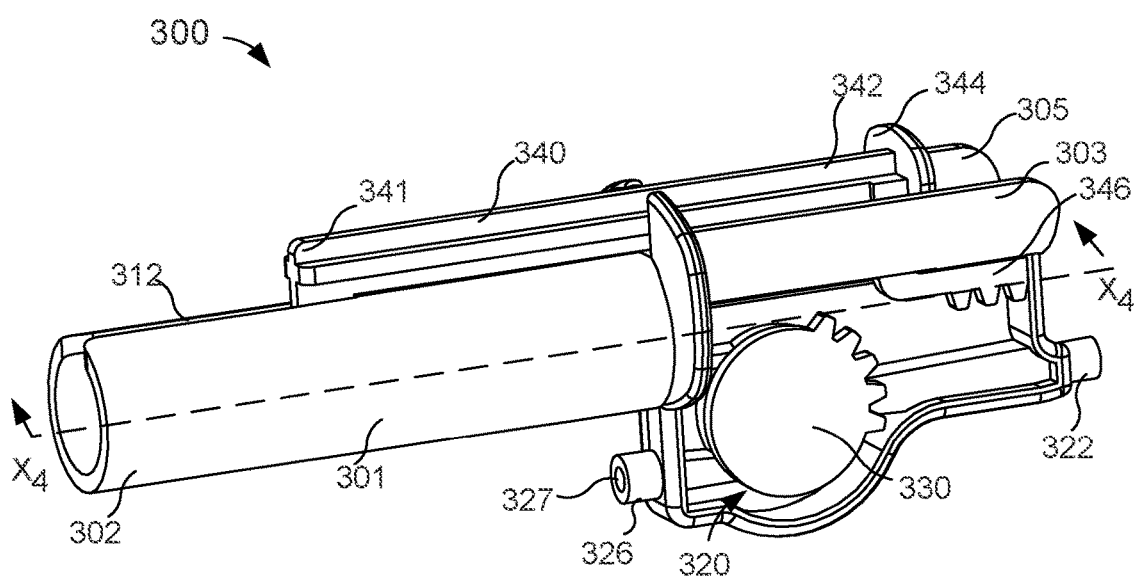
FIG. 14 is a perspective view of the bodily-fluid transfer device of FIG. 13.

While the transfer device 200 is shown and described in FIGS. 2-12 as disposing the diverter 220 within the housing 201, in some embodiments, a transfer device can include a diverter and housing that are monolithically formed. For example, FIGS. 13-19 illustrate a transfer device 300 according to an embodiment. FIGS. 13 and 14 illustrate the transfer device 300 in a first configuration. The transfer device 300 includes a housing 301, having a diverter 320 and defining a fluid reservoir 370, a flow control mechanism 330, and an actuator 340.

Figure 15:
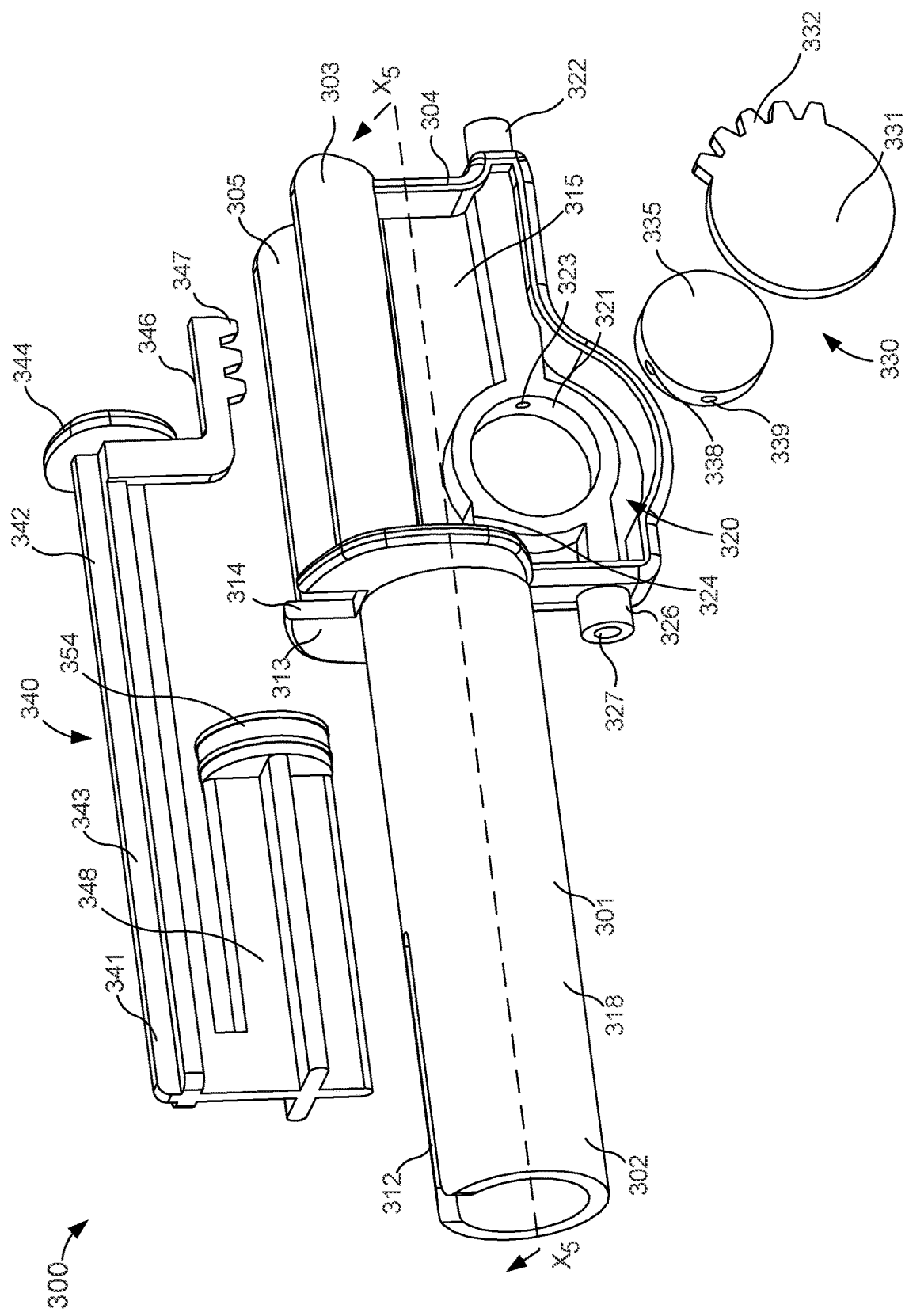
FIG. 15 is an exploded view of the bodily-fluid transfer device of FIG. 13.
Figure 16:
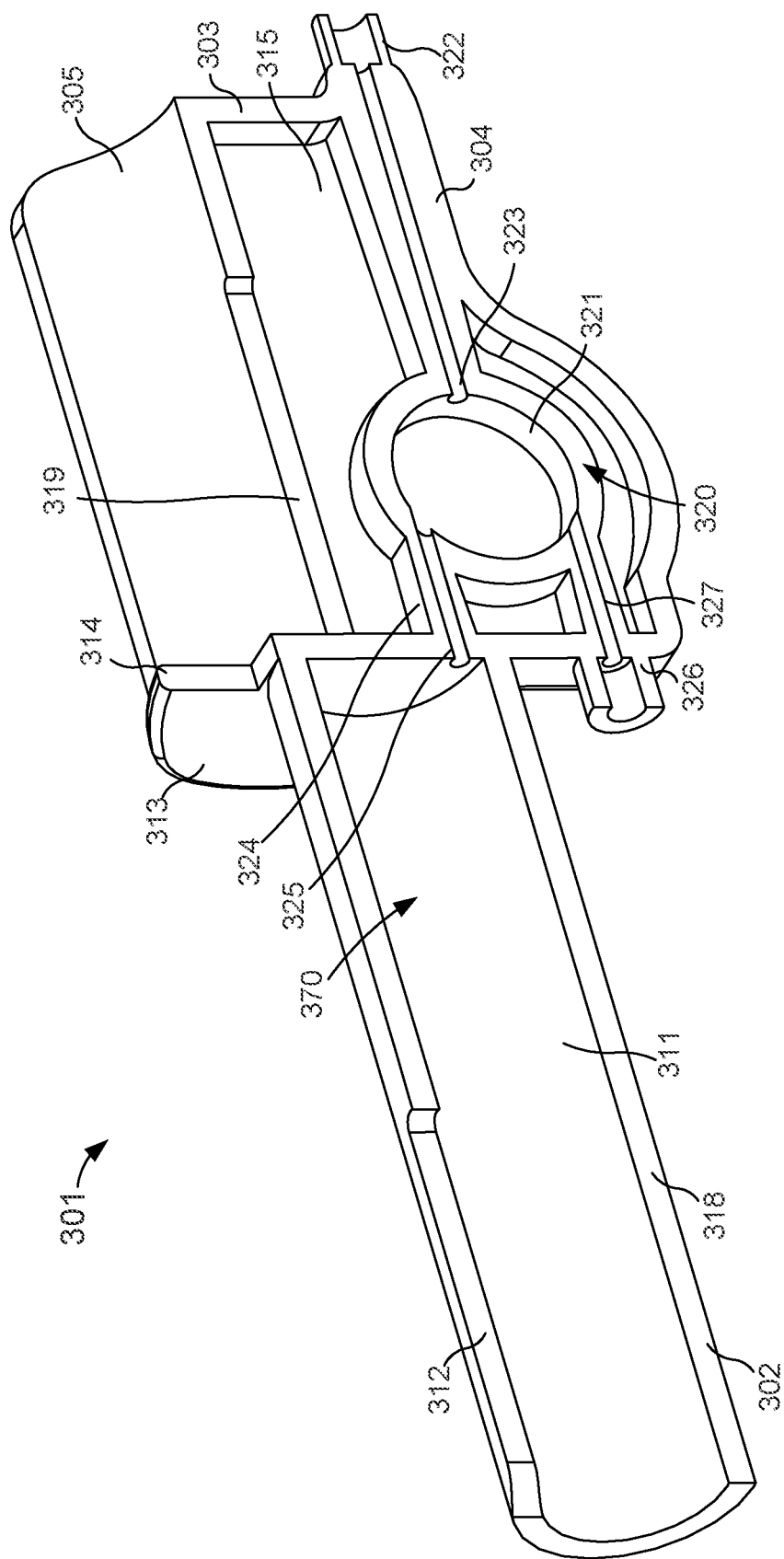
FIG. 16 is a cross-sectional view of a housing included in the bodily-fluid transfer device of FIG. 13 taken along the line $X_5$-$X_5$ in FIG. 14.

The housing 301 includes a proximal end portion 302 and a distal end portion 303. The distal end portion 303 of the housing 301 includes a set of walls 304 that define a channel 305 configured to receive a distal portion 342 of the actuator 340. The walls 304 can be configured to define the channel 305 with any suitable shape, size, or configuration. For example as shown in FIG. 16, the walls 304 can be configured to further define a slot 319 in the channel 305 configured to receive an activation extension 346 included in the actuator 340 (FIG. 15). Similarly stated, the slot 319 can be configured to receive the activation extension 346 included in the distal portion 342 of the actuator 340, disposed within the channel 305, such that the activation extension 346 can pass through the walls 304 and be disposed substantially outside the channel 305, as described in further detail herein.

The walls 304 of the distal end portion 303 of the housing 301 also include a recessed surface 315 and a stop 313 (FIGS. 15 and 16). The stop 313 defines a proximal boundary of the channel 305 that can limit the movement of the actuator 340 within the channel 305. Furthermore, the stop 313 defines a passageway 314 configured to receive a portion of the actuator 340 such that the portion of the actuator 340 can extend in the proximal direction beyond the stop 313, as further described herein. The recessed surface 315 is configured to be a flat surface from which the diverter 320 can extend. Similarly stated, the diverter 320 is a set of walls configured to extend perpendicularly from the recessed surface 315. In this manner, the diverter 320 receives at least a portion of the flow control mechanism 340, as described in further detail herein. While shown and described as extending perpendicularly from the recessed surface 315, in other embodiments, the diverter 320 can extend from the recessed surface 315 at any suitable angular orientation.

As shown in FIG. 15, the proximal end portion 302 of the housing 301 includes a set of walls 318 that extend from the stop 313 in the proximal direction. In this manner, the walls 318 define a tubular shape substantially enclosed at the distal end by the stop 313 and open at the proximal end. The walls 318 define a slot 312 and an inner volume 311 configured to receive a proximal end portion 341 of the actuator 340. As further described herein, the proximal end portion 302 of the housing 301, the stop 313, and the proximal end portion 341 of the actuator 340 define a fluid reservoir 370 configured to receive and/or contain a bodily fluid.

As shown in FIG. 16, the diverter 320 includes an inlet port 322, a first outlet port 324, and a second outlet port 326, and defines an inner volume 321. The inner volume 321 is configured to receive at least a portion of the flow control mechanism 330, as further described herein. The inlet port 322 of the diverter 320 defines an inlet lumen 323. The inlet lumen 323 is configured to be in fluid communication with the inner volume 321. Similarly stated, the inlet lumen 323 of the inlet port 322 extends through a wall defining the inner volume 321 of the diverter 320.

The inlet port 322 is further configured to be fluidically coupled to a medical device (not shown) defining a fluid flow pathway for withdrawing and/or conveying the bodily-fluid from a patient to the transfer device 300. For example, the inlet port 322 can be fluidically coupled to a needle or other lumen-containing device (e.g., flexible sterile tubing). Similarly stated, the inlet lumen 323 defined by the inlet port 322 is placed in fluid communication with a lumen defined by a lumen-containing device, when the lumen-containing device is coupled to the inlet port 322. Expanding further, when the lumen-containing device is disposed within a portion of a body of the patient (e.g., within a vein of the patient), the inner volume 321 of the diverter 320 is placed in fluid communication with the portion of the body of the patient.

The first outlet port 324 of the diverter 320 defines a first outlet lumen 325. The first outlet lumen 325 is configured to be in fluid communication with the inner volume 321 of the diverter 320 and the fluid reservoir 370 (described above). Similarly stated, the first outlet lumen 325 is configured to extend through the wall defining the inner volume 321 and through a portion of the stop 313 defining the fluid reservoir 370, thereby placing the fluid reservoir 370 in fluid communication with the inner volume 321. The second outlet port 326 of the diverter 320 defines a second outlet lumen 327 and can be coupled to an external fluid reservoir. In this manner, the second outlet lumen 327 can extend through the wall defining the inner volume 321 to be in fluid communication with the inner volume 321 and can be fluidically coupled to the external reservoir to place the external fluid reservoir in fluid communication with the inner volume 321.

As shown in FIG. 15, the flow control mechanism 330 includes a first control member 331 and a second control member 335. At least a portion of the flow control mechanism 330 is configured to be disposed within the inner volume 321 defined by the diverter 320. In this manner, the flow control mechanism 330 defines a circular cross-sectional shape such that when the flow control mechanism 330 is disposed within the inner volume 321, a portion of the flow control mechanism 330 forms a friction fit with the walls of the diverter 320 defining the inner volume 321, as described in further detail herein.

The first control member 331 includes a set of activation protrusions 332 configured to engage a set of protrusion 347 included in the activation extension 346 of the actuator 340. Therefore, in use, the actuator 340 can engage the activation protrusions 332 to move the flow control mechanism 330 between a first configuration and a second configuration. The second control member 335 defines a first lumen 338 and a second lumen 339 and can be formed from any suitable material. For example, in some embodiments, the second control member 335 is formed from silicone. In other embodiments, the second control member 335 can be any suitable elastomer configured to deform when disposed within the inner volume 321 of the diverter. Expanding further, the second control member 335 has a diameter larger than the diameter of the inner volume 321. In the manner, the diameter of the second control member 335 is reduced when the second control member 335 is disposed within the inner volume 321. Thus, the outer surface of the second control member 335 forms a friction fit with the inner surface of the walls defining the inner volume 321.

The second control member 335 is configured to be coupled to the first control member 331. For example, in some embodiments, the first control member 331 can be coupled to the second control member 335 via a mechanical fastener and/or adhesive. In other embodiments, the first control member 331 and the second control member 335 can be coupled in any suitable manner. In this manner, the second control member 335 is configured to move concurrently with the first control member 331 when the activation extension 347 of the actuator 340 engages the activation protrusions 332 of the first control member 331. Similarly stated, the flow control mechanism 330 is moved between the first configuration and the second configuration when the first control member 331 and the second control member 335 are moved between the first configuration and the second configuration, respectively. Furthermore, when the flow control mechanism 330 is in the first configuration, the first lumen 338 is placed in fluid communication with the inlet lumen 323 defined by the inlet port 322 and the first outlet lumen 325 defined by the first outlet port 324. When the flow control mechanism 330 is in the second configuration, the second lumen 339 is placed in fluid communication with the inlet lumen 323 defined by the inlet port 322 and the second outlet lumen 327 defined by the second outlet port 326, as described in further detail herein.

As described above, the actuator mechanism 340 includes the proximal end portion 341, the distal end portion 342, and an actuator arm 343 therebetween. The actuator mechanism 340 is configured to move between a first configuration and a second configuration, thereby moving the transfer device 300 between a first configuration and a second configuration, as described in further detail herein. The proximal end portion 341 includes a plunger 348 configured to be disposed within the inner volume 311 of the housing 301. More particularly, the plunger 348 includes a seal member 354 configured to define a friction fit with the inner surface of the walls 318 defining the inner volume 311. Similarly stated, the seal member 354 defines a fluidic seal with the inner surface of the walls 318 defining the inner volume 311 such that a portion of the inner volume 311 proximal of the seal member 354 is fluidically isolated from a portion of the inner volume 311 distal of the seal member 354.

The actuator arm 343 is configured to extend from the proximal end portion 341 of the actuator 340 through the passageway 314 defined by the stop 313. Therefore, as described above, the distal end portion 342 of the actuator 340 is disposed on a distal side of the stop 313. More specifically, the distal end portion 342 includes an engagement portion 344 and the activation portion 346. The engagement portion 344 and at least a portion (e.g., a distal portion) of the actuator arm 343 are configured to be disposed within the channel 305 such that the activation portion 346 can extend through the slot 319, as described above. In this manner, a user can engage the engagement portion 344 to move the actuator 340 in a distal direction between a first configuration and a second configuration, as further described herein.

In some embodiments, the transfer device 300 can be stored in the first configuration in which the first lumen 338 of the second control member 335 is in fluid communication with the inlet port 322 and the first outlet port 324. In such embodiments, the friction fit defined by the second control member 335 and the walls of the diverter 320 defining the inner volume 321 maintain the flow control mechanism 330 in the first configuration until the actuator 340 moves the flow control mechanism 330 to the second configuration.

In use, a user can engage the transfer device 300 to couple the inlet port 322 to a proximal end portion of a lumen-defining device (not shown) such as, for example, a butterfly needle. With the inlet port 322 coupled to the lumen-defining device the inlet lumen 323 is placed in fluid communication with the lumen defined by the lumen-defining device. Furthermore, the distal end portion of the lumen-defining device can be disposed within a portion of the body of a patient (e.g., a vein), thus, the inlet lumen 323 is in fluid communication with the portion of the body of the patient. In a similar manner, the second outlet port 326 can be coupled to an external fluid reservoir (not shown). The external fluid reservoir can be any suitable reservoir. For example, in some embodiments, the external fluid reservoir can be a BacT/ALERT® SN or a BacT/ALERT® FA blood culture collection bottle with media specifically designed to facilitate the growth of certain types of microbes (e.g., aerobic media/broth and/or aerobic media/broth), manufactured by BIOMERIEUX, INC.

Figure 17:
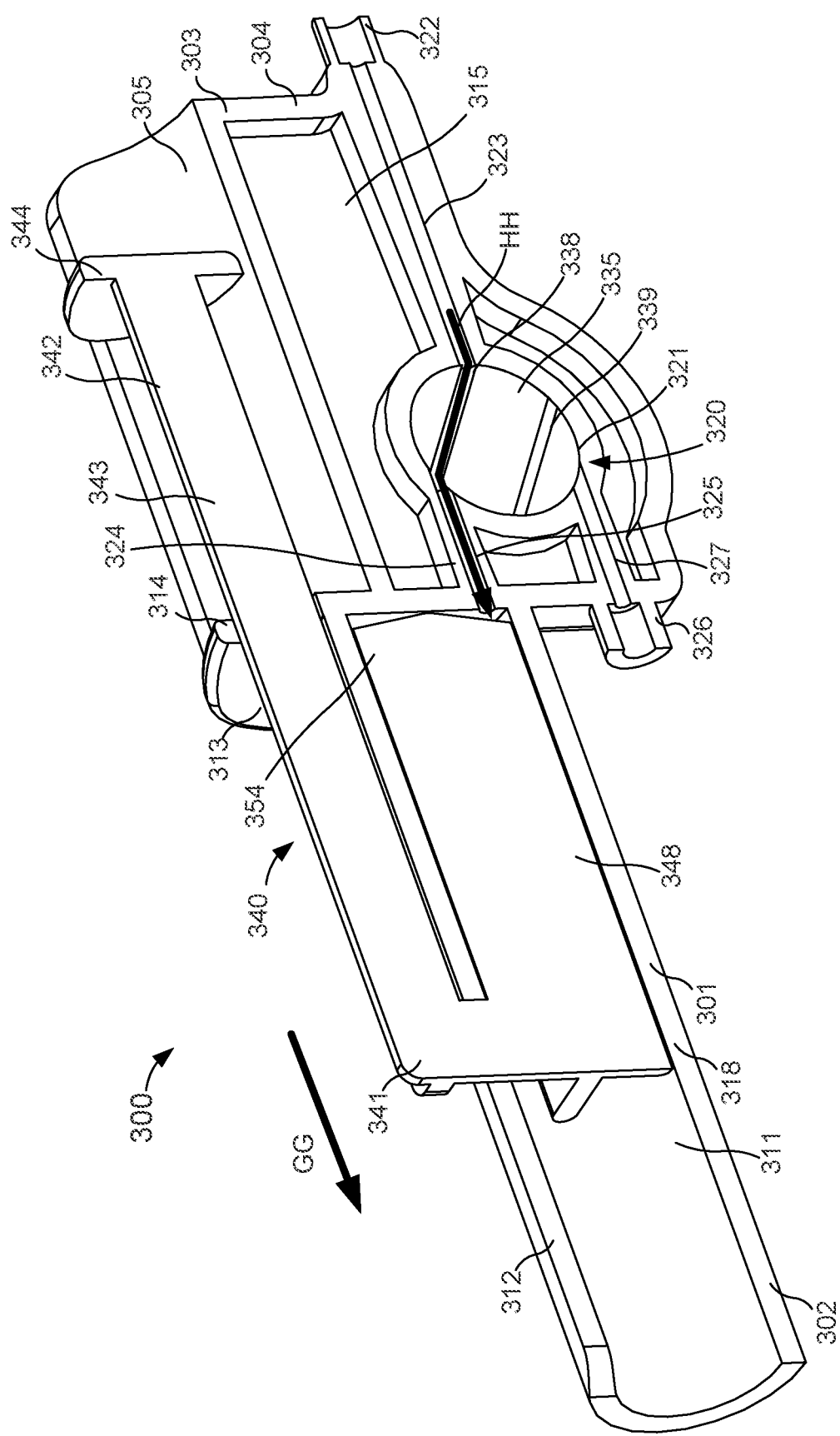
FIG. 17 is a cross-sectional view of the bodily-fluid transfer device taken along the line $X_4$-$X_4$ in FIG. 14 in a first configuration.

With the inlet port 322 coupled to the lumen-defining device and the second outlet port 326 coupled to the external fluid reservoir, a user can begin the transfer of a bodily-fluid by applying an activation force to the engagement portion 344 of the actuator 340, thereby moving the actuator 340 the distal direction, as shown by the arrow GG in FIG. 17. More specifically and as described above, the plunger 348 engages the inner surface of the walls 318 defining the inner volume 311 such that the volume of the fluid reservoir 370 is increased (e.g., as defined by the plunger 348, the walls 318 of the housing 301 and the stop 313). With the fluid reservoir 370 being fluidically isolated (as described above) from a volume on the proximal side of the seal member 354, the increase in the volume of the fluid reservoir 370 produces a negative pressure within the fluid reservoir 370. Moreover, with the flow control mechanism 330 in the first configuration, negative pressure differential introduces a suction force within the first lumen 338, the inlet lumen 323, and the first outlet lumen 325.

As shown by the arrow HH, the inlet lumen 323 of the inlet port 322, the first lumen 338 of the second control member 335, and the first outlet lumen 325 of the first outlet port 324 define a fluid flow path such that the second portion 376 of the inner volume 373 defined by the fluid reservoir 370 is in fluid communication with the inlet port 322. Furthermore, with the inlet port 322 coupled to the lumen-defining device the fluid reservoir 370 is in fluid communication with the portion of the patient (e.g., the vein) and at least a portion of the suction force is introduced to the portion of the patient. In this manner, a bodily-fluid is drawn into the fluid reservoir 370. In some embodiments, the bodily-fluid can contain undesirable microbes such as, for example, dermally-residing microbes dislodged during the insertion of the lumen-defining device.

In some embodiments, the magnitude of the suction force can be modulated by moving the actuator 340 in the proximal or distal direction. For example, in some embodiments, it can be desirable to limit the amount of suction force introduced to a vein. In such embodiments, the user can move the actuator 340 in the proximal direction (e.g., the direction of the arrow II in FIG. 18) such the activation extension 346 can engage the protrusions 332 of the first control member 331. In this manner, the protrusions 347 included in the activation extension 346 can mesh with the protrusions 332 of the first control member 331 to rotate the first control member 331 in the direction of the arrow JJ. The rotation of the flow control mechanism 330 (e.g., in a direction opposite the arrow JJ) reduces the size of the fluid pathway (e.g., an inner diameter) between the inlet lumen 323 and the first lumen 338 and the first outlet port 325 and the first lumen 338, thereby reducing the suction force introduced into the vein of the patient.

With the desired amount of bodily-fluid transferred to the fluid reservoir 370, a user can engage the transfer device 300 to move the transfer device 300 from the first configuration to the second configuration, wherein a flow of bodily-fluid is transferred to the external reservoir (e.g., such as those described above). In some embodiments, the desired amount of bodily-fluid transferred to the fluid reservoir 370 is a predetermined amount of fluid. For example, in some embodiments, the transfer device 300 can be configured to transfer bodily-fluid until the pressure within the fluid reservoir 370 is equilibrium with the pressure of the portion of the body in which the lumen-defining device is disposed (e.g., the vein). In such embodiments, the equalizing of the pressure between the fluid reservoir 370 and the portion of the body stops the flow of the bodily-fluid into the fluid reservoir 370. In some embodiments, the predetermined amount of bodily-fluid (e.g., volume) is at least equal to the combined volume of the inlet lumen 323, the first lumen 338, the first outlet lumen 325, and the lumen-defining device.

Figure 18:
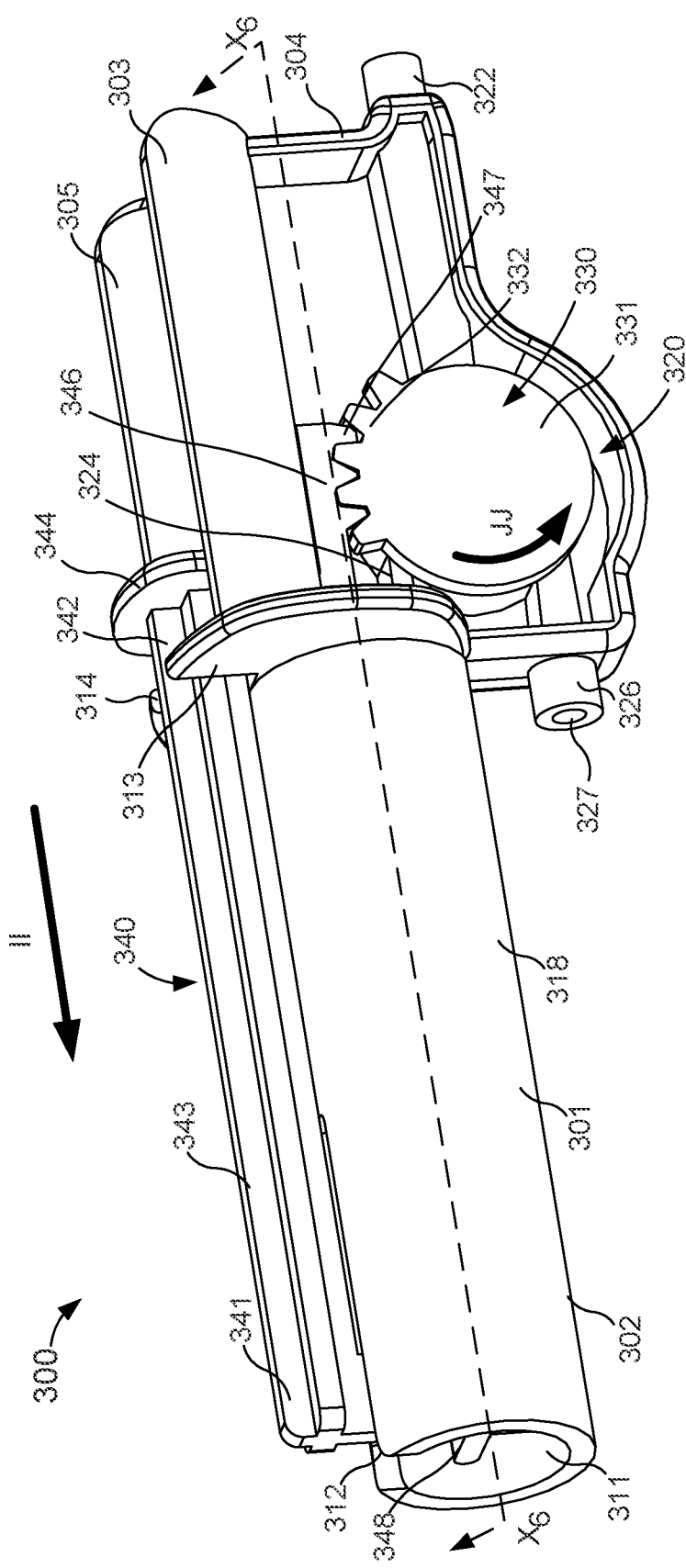
FIG. 18 is a perspective view of the bodily-fluid transfer device of FIG. 13, in a second configuration.
Figure 19:
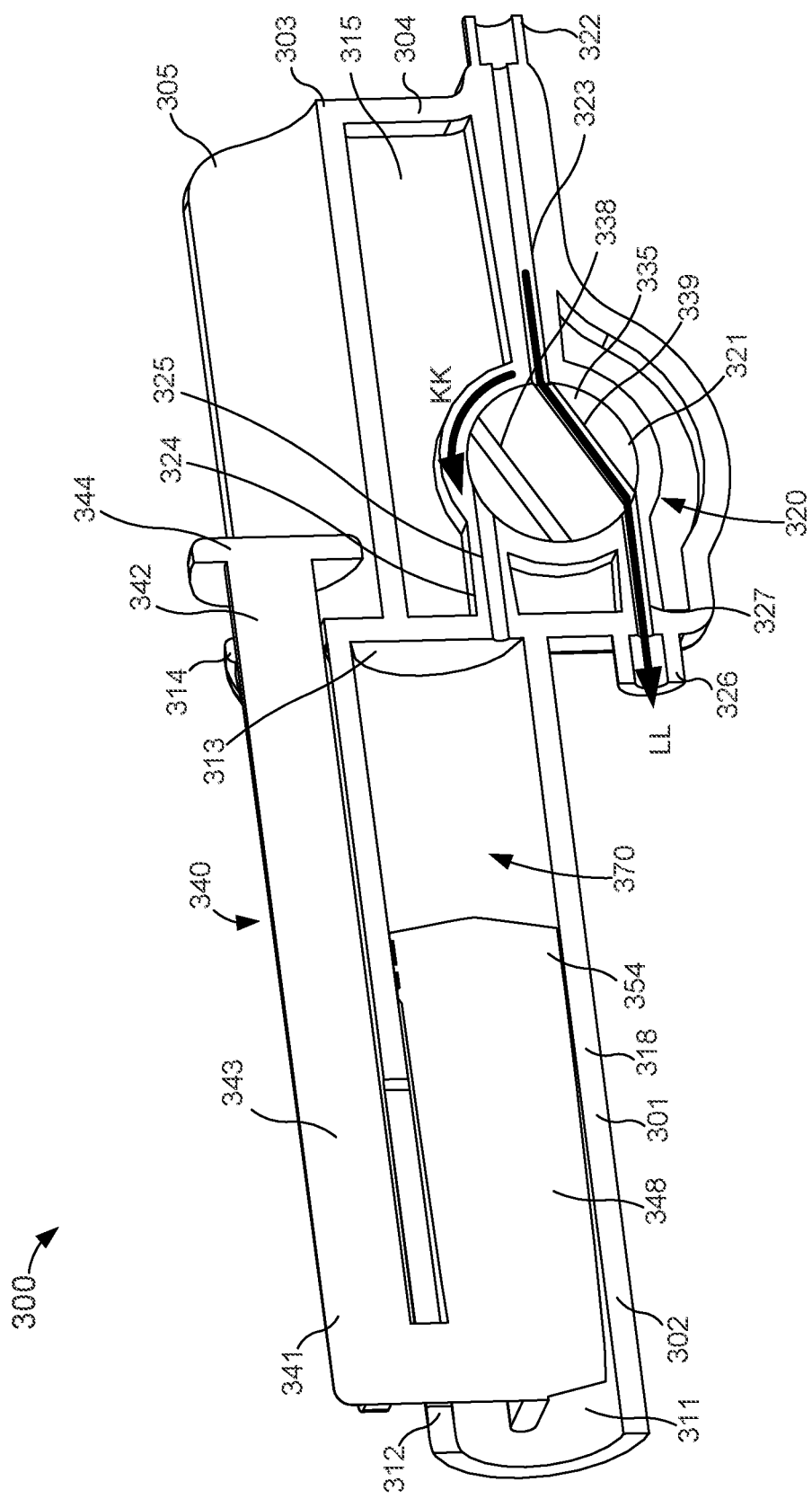
FIG. 19 is a cross-sectional view of the bodily-fluid transfer device of FIG. 18 taken along the line $X_6$-$X_6$.

As shown in FIG. 18, the transfer device 300 can be moved from the first configuration to the second configuration by further moving the actuator mechanism 340 in the distal direction, as indicated by the arrow II. As the actuator mechanism 340 is moved from the first configuration toward the second configuration, the protrusions 347 of the activation extension 346 further engage the activation protrusions 332 included in the first control member 331 to move the flow control mechanism 330 to the second configuration, as indicated by the arrow KK in FIG. 19. In this manner, the flow control mechanism 330 is moved to the second configuration, and the first lumen 238 is fluidically isolated from the inlet lumen 223 and the first outlet lumen 225. In addition, the second lumen 339 defined by the second control member 335 is placed in fluid communication with the inlet lumen 323 defined by the inlet port 322 and the second outlet lumen 327 defined by the second outlet port 326.

As shown by the arrow LL, the inlet lumen 323 of the inlet port 322, the second lumen 339 of the second control member 335, and the second outlet lumen 327 of the second outlet port 326 define a fluid flow path such that the external reservoir (not shown in FIG. 19) is in fluid communication with the inlet port 322 and, therefore, the portion of the patient (e.g., the vein). Furthermore, the external reservoir is configured to define a negative pressure (e.g., the known external reservoirs referred to herein are vessels defining a negative pressure). The negative pressure within the external reservoir is such that the negative pressure differential between the external reservoir and the portion of the body of the patient introduces a suction force within the portion of the patient. Therefore, a desired amount of bodily-fluid is drawn into the external reservoir and is fluidically isolated from the first, predetermined amount of bodily-fluid contained within the fluid reservoir 370.

The bodily-fluid contained in the external reservoir is substantially free from microbes generally found outside of the portion of the patient (e.g., dermally residing microbes, microbes within a lumen defined by the transfer device 300, microbes within the lumen defined by the lumen defining device, and/or any other undesirable microbe). In some embodiments, with the desired amount of bodily-fluid contained in the external fluid reservoir, the user can further move the actuator 340 in the proximal direction to place the transfer device 300 in a third configuration. In such embodiments, the actuator 340 can be moved in the proximal direction such that the engagement portion 344 and/or the activation extension 346 contact the stop 313, thereby limiting further proximal movement of the actuator 340. In this configuration, the actuator 340 can place the flow control mechanism 330 in a third configuration configured to fluidically isolate the first lumen 338 and the second lumen 339 from the inlet lumen 323, the first outlet lumen 325, and the second outlet lumen 327. Thus, the bodily-fluid contained within the fluid reservoir 370 is fluidically isolated from a volume outside the fluid reservoir 370 and the external reservoir can be decoupled from the transfer device 300.

Figure 20:
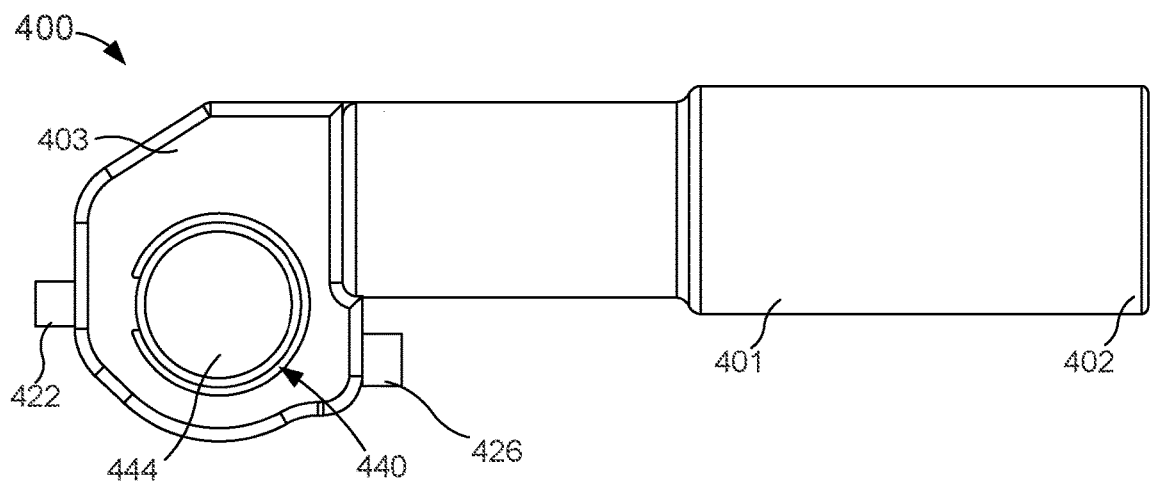
FIG. 20 is a front view of a bodily-fluid transfer device according to an embodiment.
Figure 21:
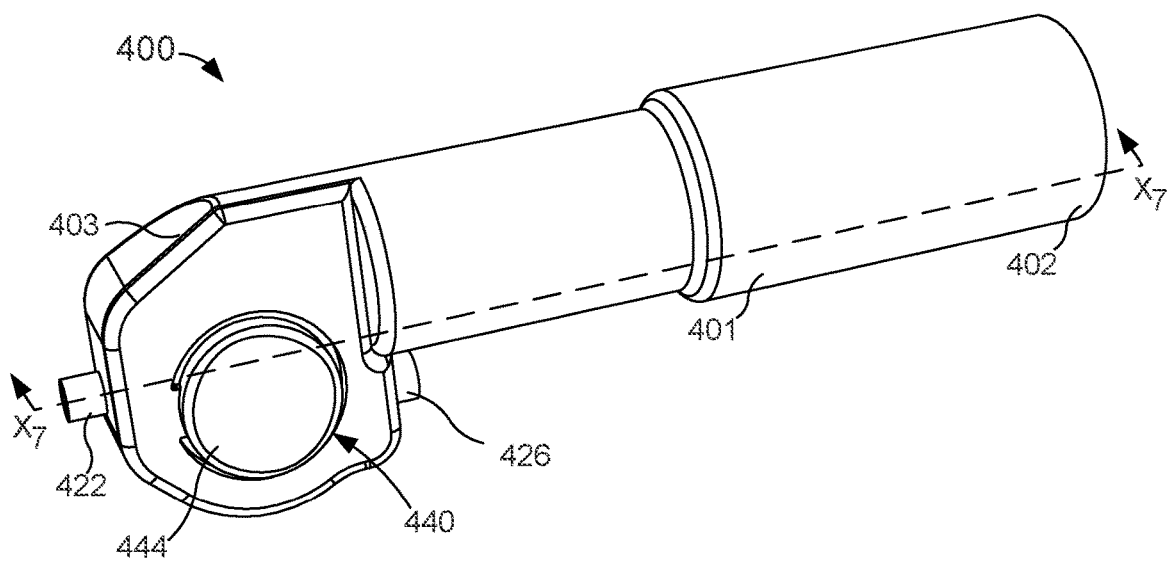
FIG. 21 is a perspective view of the bodily-fluid transfer device of FIG. 20.

While the transfer device 300 is shown and described in FIGS. 13-19 as being configured to actuated by continual user influence (e.g., the user manually moves the actuator 340 in the proximal direction), in some embodiments, a transfer device need not require continual user influence. For example, FIGS. 20-26 illustrate a transfer device 400 according to an embodiment. FIGS. 20 and 21 illustrate the transfer device 400 in a first configuration. The transfer device 400 includes a housing 401, having a diverter 420 and defining a fluid reservoir 470, a flow control mechanism 430, and an actuator mechanism 440.

Figure 22:
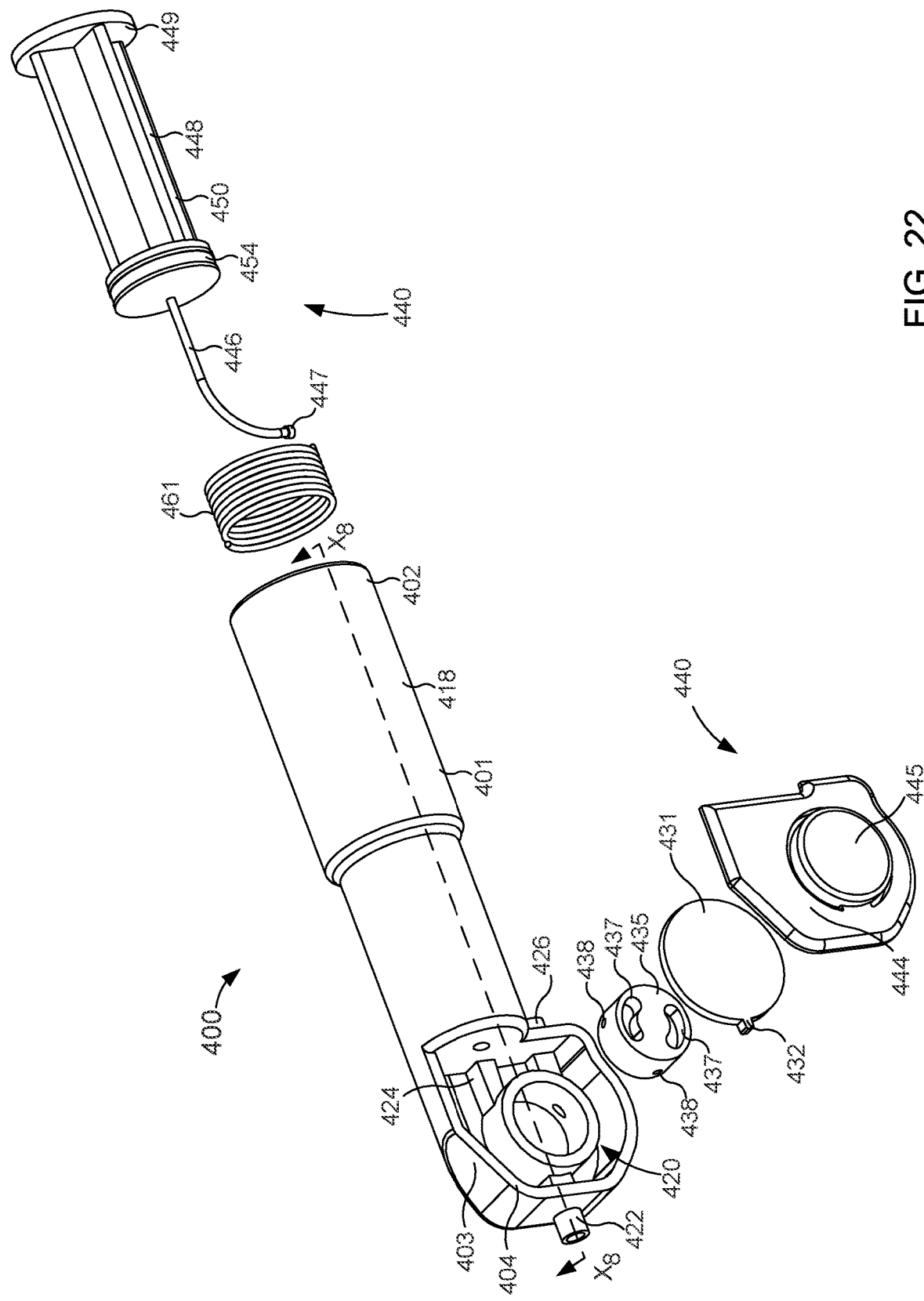
FIG. 22 is an exploded view of the bodily-fluid transfer device of FIG. 20.
Figure 23:
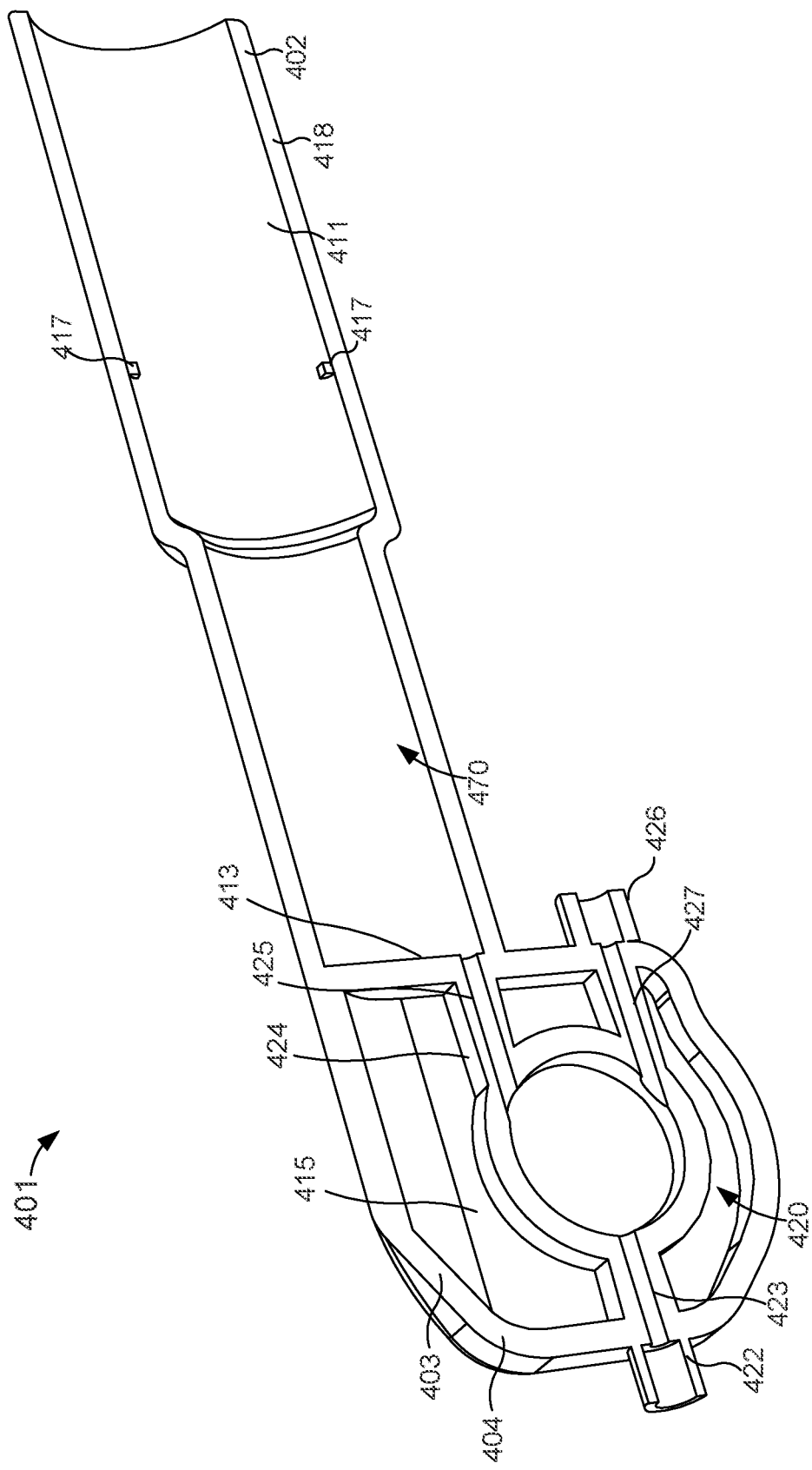
FIG. 23 is a cross-sectional view of a housing included in the bodily-fluid transfer device of FIG. 20 taken along the line $X_8$-$X_8$ in FIG. 21.

The housing 401 includes a proximal end portion 402 and a distal end portion 403. The distal end portion 403 of the housing 401 includes a set of walls 404 having a recessed portion 415 and a stop 413 (FIGS. 22 and 23). The stop 413 defines a distal boundary of the recessed portion 415 and defines a passageway 414. The passageway 414 is configured to receive an activation extension 346 included in the actuator mechanism 440 such that the activation extension 346 extends through the stop 413, as further described herein. The recessed portion 415 includes a substantially flat surface from which the diverter 420 can extend (FIG. 22). Similarly stated, the diverter 420 is a set of walls configured to extend perpendicularly from the surface of the recessed portion 415. In this manner, the diverter 420 receives at least a portion of the flow control mechanism 430, as described in further detail herein. While shown and described as extending perpendicularly from the surface of the recessed portion 415, in other embodiments, the diverter 420 can extend from the surface at any suitable angular orientation.

The proximal end portion 402 of the housing 401 includes a set of walls 418 that extend from the stop 413 in the proximal direction. In this manner, the walls 418 define a tubular shape substantially enclosed at the distal end by the stop 413 and open at the proximal end. The proximal end portion 402 of the housing 401 can be formed from any suitable material. For example, in some embodiments, the proximal end portion 402 can be formed from a relatively flexible material. In such embodiments, the proximal end portion 402 can be configured to deform (e.g., bend, compress, or otherwise reconfigure) under a given force, as described in further detail herein. As shown in FIG. 23, the walls 418 include shoulder 416 and retention tabs 417 and define an inner volume 411 configured to receive a portion of the actuator mechanism 440. As further described herein, the proximal end portion 402 of the housing 401, the stop 413, and a portion of the actuator mechanism 440 define a fluid reservoir 470 configured to receive and/or contain a bodily fluid.

As shown in FIG. 23, the diverter 420 includes an inlet port 422, a first outlet port 424, and a second outlet port 426, and defines an inner volume 421. The inner volume 421 is configured to receive at least a portion of the flow control mechanism 430, as further described herein. The inlet port 422 of the diverter 420 defines an inlet lumen 423. The inlet lumen 423 is configured to be in fluid communication with the inner volume 421. Similarly stated, the inlet lumen 423 of the inlet port 422 extends through a wall defining the inner volume 421 of the diverter 420.

The inlet port 422 is further configured to be fluidically coupled to a medical device (not shown) defining a fluid flow pathway for withdrawing and/or conveying the bodily-fluid from a patient to the transfer device 400. For example, the inlet port 422 can be fluidically coupled to a needle or other lumen-containing device (e.g., flexible sterile tubing). Similarly stated, the inlet lumen 423 defined by the inlet port 422 is placed in fluid communication with a lumen defined by a lumen-containing device, when the lumen-containing device is coupled to the inlet port 422. Expanding further, when the lumen-containing device is disposed within a portion of a body of the patient (e.g., within a vein of the patient), the inner volume 421 of the diverter 420 is placed in fluid communication with the portion of the body of the patient.

The first outlet port 424 of the diverter 420 defines a first outlet lumen 425. The first outlet lumen 425 is configured to be in fluid communication with the inner volume 421 of the diverter 420 and the fluid reservoir 470 (described above). Similarly stated, the first outlet lumen 425 is configured to extend through the wall defining the inner volume 421 and through a portion of the stop 413 defining the fluid reservoir 470, thereby placing the fluid reservoir 470 in fluid communication with the inner volume 421. The second outlet port 426 of the diverter 420 defines a second outlet lumen 427 and is configured to be coupled to an external fluid reservoir. In this manner, the second outlet lumen 427 can extend through the wall defining the inner volume 421 to be in fluid communication with the inner volume 421 and can be fluidically coupled to the external reservoir to place the external fluid reservoir in fluid communication with the inner volume 421.

Figure 24:
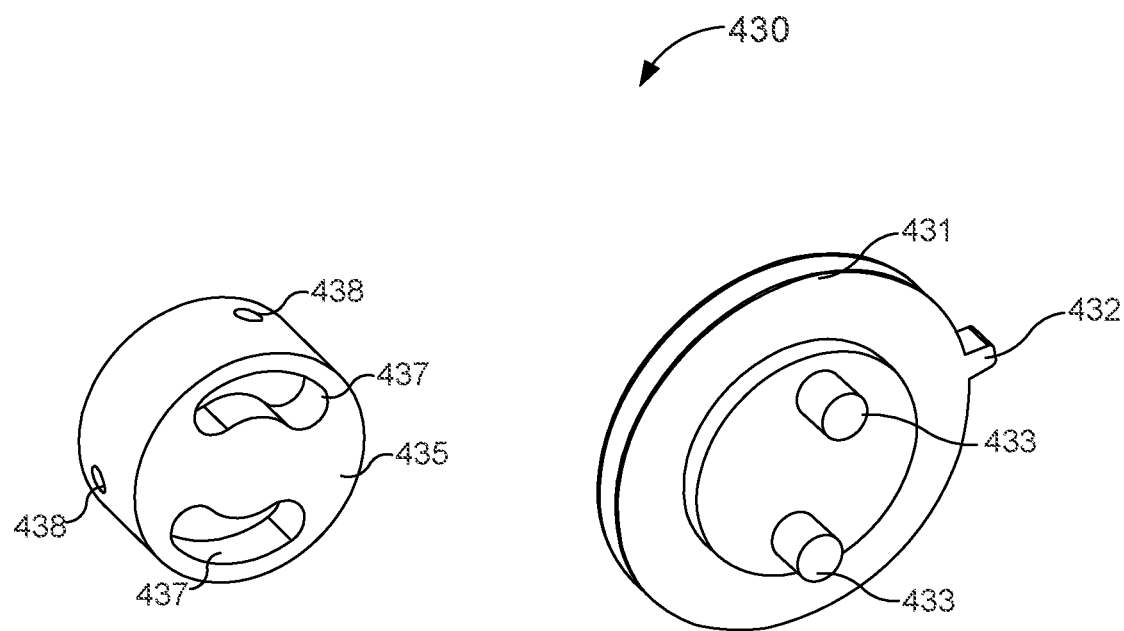
FIG. 24 is a perspective view of a first control member and a second control member included in a flow control mechanism of the bodily-fluid transfer device of FIG. 20.

As shown in FIG. 24, the flow control mechanism 430 includes a first control member 431 and a second control member 435. At least a portion of the flow control mechanism 430 is configured to be disposed within the inner volume 421 defined by the diverter 420. In this manner, the flow control mechanism 430 defines a circular cross-sectional shape such that when the flow control mechanism 430 is disposed within the inner volume 421, a portion of the flow control mechanism 430 forms a friction fit with the walls of the diverter 420 defining the inner volume 421, as described in further detail herein.

The first control member 431 includes an activation protrusion 432 and engagement protrusions 433. The activation protrusion 432 is configured to engage a protrusion 447 included in the activation extension 446 of the actuator mechanism 440. Therefore, in use, the actuator mechanism 440 can engage the activation protrusion 432 to move the flow control mechanism 430 between a first configuration and a second configuration. The second control member 435 defines a first lumen 438, a second lumen 439, and a set of grooves 437. The second control member 435 can be formed from any suitable material such as, for example, silicone. In other embodiments, the second control member 435 can be any suitable elastomer configured to deform when disposed within the inner volume 421 of the diverter. Expanding further, the second control member 435 has a diameter larger than the diameter of the inner volume 421. In the manner, the diameter of the second control member 435 is reduced when the second control member 435 is disposed within the inner volume 421. Thus, the outer surface of the second control member 435 forms a friction fit with the inner surface of the walls defining the inner volume 421.

The grooves 437 defined by the second control member 435 are configured to receive the engagement protrusions 433. In this manner, the first control member 431 can selectively engage the second control member 435 such that the second control member 435 is moved concurrently with the first control member 431 when the activation extension 447 of the actuator mechanism 440 engages the activation protrusion 432 of the first control member 431. Similarly stated, the flow control mechanism 430 is moved between the first configuration and the second configuration when the first control member 431 and the second control member 435 are moved between the first configuration and the second configuration, respectively. Furthermore, when the flow control mechanism 430 is in the first configuration, the first lumen 438 is placed in fluid communication with the inlet lumen 423 defined by the inlet port 422 and the first outlet lumen 425 defined by the first outlet port 424. When the flow control mechanism 430 is in the second configuration, the second lumen 439 is placed in fluid communication with the inlet lumen 423 defined by the inlet port 422 and the second outlet lumen 427 defined by the second outlet port 426, as described in further detail herein.

Figure 25:
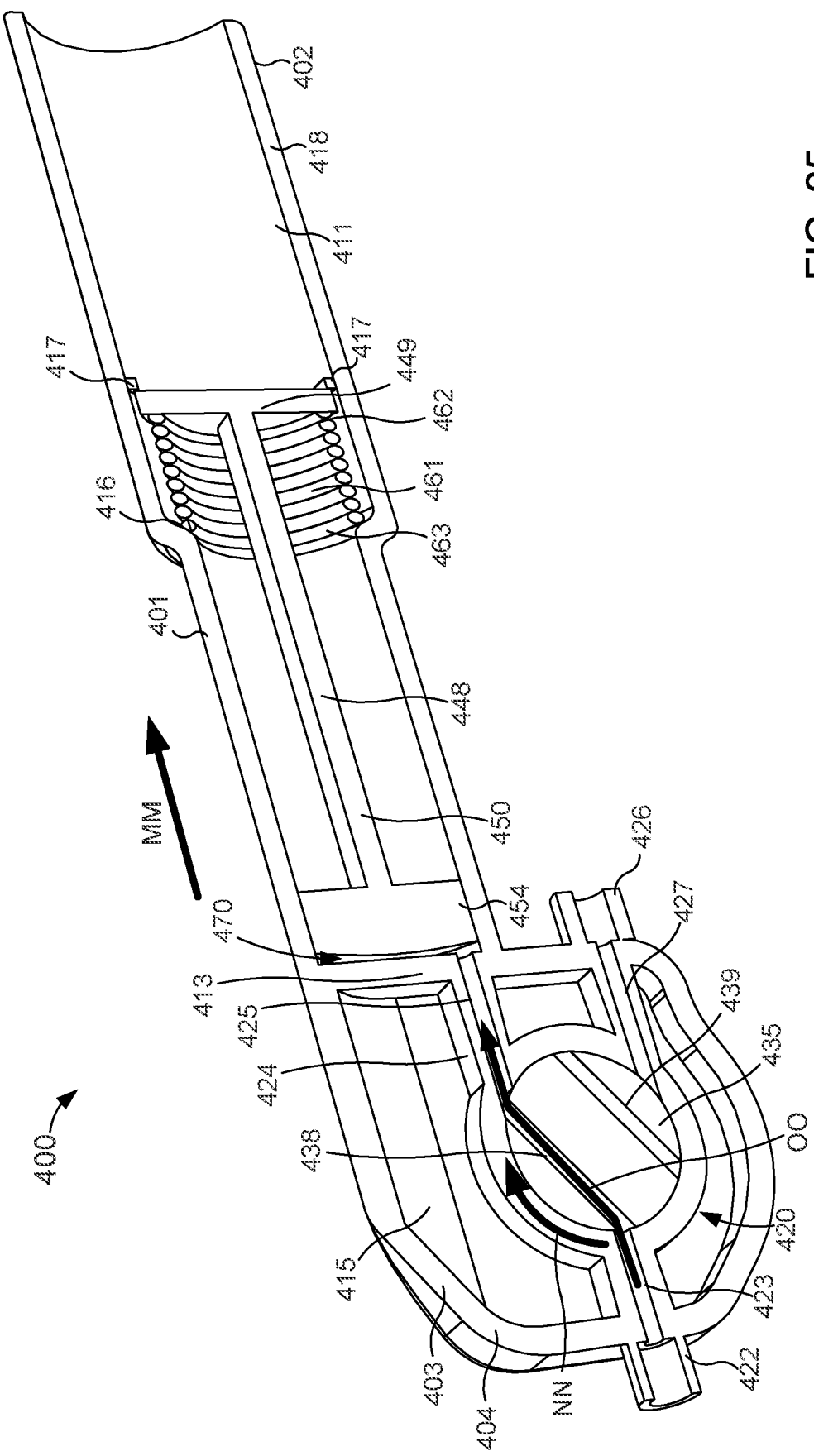
FIG. 25 is a cross-sectional view of the bodily-fluid transfer device of FIG. 20 taken along the line $X_7$-$X_7$ in FIG. 21 in a first configuration.
Figure 26:
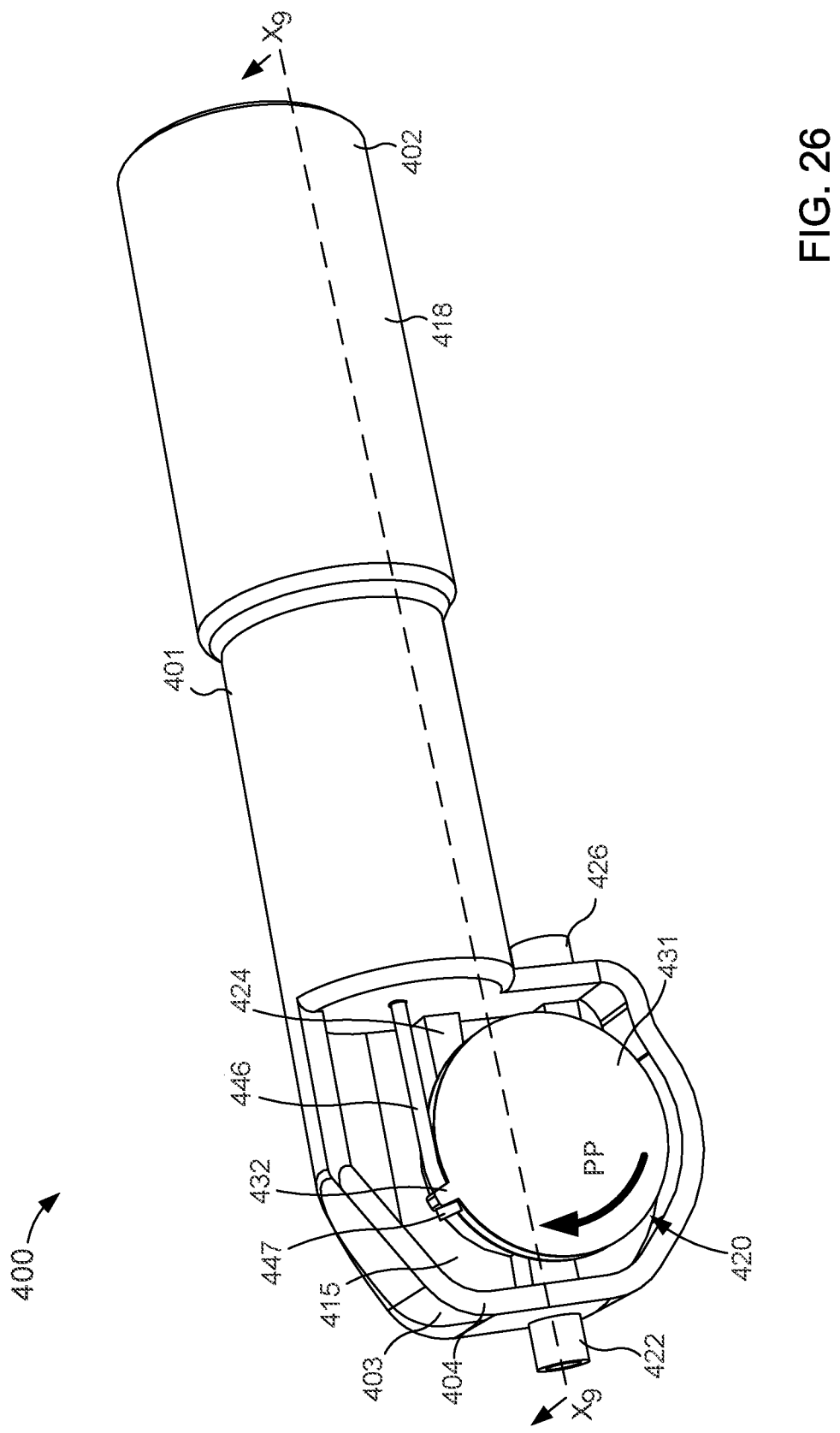
FIG. 26 is a perspective view of the bodily-fluid transfer device of FIG. 20, in a second configuration.

As shown in FIGS. 22 and 25, the actuator mechanism 440 includes an engagement member 444, the activation extension 446, a plunger 448, and a spring 461. The engagement member 444 is configured to be coupled to the distal end portion 403 of the housing 401. In this manner, the housing 401 and the engagement member 444 house the flow control mechanism 430 and at least a portion of the diverter 420. The engagement member 444 includes a throttling button 445. The throttling button 445 is configured such that when engaged by a user, the throttling button 445 interacts with the flow control mechanism 430 to modulate the movement of the flow control mechanism 440, as described in further detail herein.

The plunger 448 includes a proximal end portion 449 and a distal end portion 450 and is configured to be disposed within the inner volume 411 defined by the housing 401. The proximal end portion 449 of the plunger 448 is configured to selectively engage the retention protrusions 417 included in the housing 401. The plunger 448 further includes a sealing member 454 disposed at the distal end portion 450. The seal member 454 is configured to define a friction fit with the inner surface of the walls 418 defining the inner volume 411. Similarly stated, the seal member 454 defines a fluidic seal with the inner surface of the walls 418 defining the inner volume 411 such that a portion of the inner volume 411 proximal of the seal member 454 is fluidically isolated from a portion of the inner volume 411 distal of the seal member 454.

The spring 461 includes a proximal end portion 462 and a distal end portion 463 and is configured to circumscribe the plunger 448. Similarly stated, the plunger 448 is disposed within the spring 461 when the spring 461 and the plunger 448 are disposed within the housing 401. Furthermore, when disposed within the inner volume 411, the distal end portion 463 of the spring 461 is configured to engage the shoulder 416 of the housing 401 and the proximal end portion 462 is configured to engage the proximal end portion 449 of the plunger 448. In this manner, the spring 461, when urged to move from a first (compressed) configuration to a second (expanded) configuration, is configured to move the plunger 448 in the proximal direction, as described in further detail herein.

The activation extension 446 can be any suitable size, shape, or configuration. For example, as shown in FIG. 22, the activation extension 446 can be a flexible tether formed from, for example, nylon. In this manner, the activation extension 446 can be substantially flexible in a lateral direction and substantially rigid in an axial direction. Similarly stated, in some embodiments, the activation extension 446 is configured to bend, twist, conform, and/or otherwise reconfigure without stretching. Said yet another way, the length of the activation extension 446 is configured to remain substantially unchanged as the activation extension 446 is bent or otherwise reconfigured.

The activation extension 446 is configured to be coupled to the distal end portion 450 of the plunger 448. More specifically, a proximal end portion of the activation extension 446 is disposed within the inner volume 411 of the housing 401 and is coupled to the plunger 448 and a distal end portion of the activation extension 446 passes through the stop 413 and is disposed within the recessed portion 415 of the housing 401. In this manner, the activation extension 446 is configured engage the activation protrusion 432 of the first control member 431 to move the flow control mechanism 430 between the first configuration and the second configuration, as described in further detail herein.

In some embodiments, the transfer device 400 can be stored in a storage configuration in which the second control member 435 of the flow control mechanism 430 fluidically isolates the inlet port 422, the first outlet port 424, and the second outlet port 426 from the inner volume 421 defined by the diverter 420. In such embodiments, first lumen 438 and the second lumen 439 are fluidically isolated from the inlet lumen 423, the first outlet lumen 425, and the second outlet lumen 427. Furthermore, the friction fit defined by the second control member 435 and the walls of the diverter 420 defining the inner volume 421 maintain the flow control mechanism 430 in the storage configuration until the flow control mechanism 430 is moved from the storage configuration.

In use, a user can engage the transfer device 400 to couple the inlet port 422 to a proximal end portion of a lumen-defining device (not shown) such as, for example, a butterfly needle. With the inlet port 422 coupled to the lumen-defining device the inlet lumen 423 is placed in fluid communication with the lumen defined by the lumen-defining device. Furthermore, the distal end portion of the lumen-defining device can be disposed within a portion of the body of a patient (e.g., a vein), thus, the inlet lumen 423 is in fluid communication with the portion of the body of the patient. In a similar manner, the second outlet port 426 can be coupled to an external fluid reservoir (not shown). The external fluid reservoir can be any suitable reservoir. For example, in some embodiments, the external fluid reservoir can be a BacT/ALERT® SN or a BacT/ALERT® FA, manufactured by BIOMERIEUX, INC.

With the inlet port 422 coupled to the lumen-defining device and the second outlet port 426 coupled to the external fluid reservoir, a user can begin a transfer of a bodily-fluid by applying an activation force to the transfer device 400. More specifically, the user can introduce an activation force to the proximal end portion 402 of the housing 401 by squeezing, for example, the sides of the proximal end portion 402 such that the proximal end portion 402 deforms in response to the activation force, as described above. Thus, the proximal end portion 402 is urged (in response to the activation force) to reconfigure such that the retention tabs 417 are removed from contact with the proximal end portion 449 of the plunger 448. Expanding further, the retention tabs 417 are configured to apply a reaction force to the proximal end portion 449 of the plunger 448 in response to an expansion force exerted by the spring 461, thereby maintaining the spring 461 in the compressed configuration. With the retention tabs 417 removed from contact with the plunger 448 and with the distal end portion 463 of the spring 461 in contact with the shoulder 416 of the housing 401, the proximal end portion 462 of the spring 462 expands to move the plunger 448 in the direction of the arrow MM in FIG. 25.

As described above, the plunger 448 engages the inner surface of the walls 418 defining the inner volume 411 such that the volume of the fluid reservoir 470 is increased (e.g., as defined by the plunger 448, the walls 418 of the housing 401 and the stop 413). With the fluid reservoir 470 being fluidically isolated (as described above) from a volume on the proximal side of the seal member 454, the increase in the volume of the fluid reservoir 470 produces a negative pressure within the fluid reservoir 470. Moreover, movement of the plunger 448 in the proximal direction is such that the activation extension 446 is moved in the proximal direction. In this manner, the protrusion 447 of the activation extension 446 engages the protrusion 432 of the first control member 431 to move the flow control mechanism 430 from the storage configuration to the first configuration, as indicated by the arrow NN. With the flow control mechanism 430 in the first configuration, the negative pressure of the fluid reservoir 470 introduces a suction force within the first lumen 438, the inlet lumen 423, and the first outlet lumen 425.

As shown by the arrow OO, the inlet lumen 423 of the inlet port 422, the first lumen 438 of the second control member 435, and the first outlet lumen 425 of the first outlet port 424 define a fluid flow path such that the second portion 476 of the inner volume 473 defined by the fluid reservoir 470 is in fluid communication with the inlet port 422. Furthermore, with the inlet port 422 coupled to the lumen-defining device the fluid reservoir 470 is in fluid communication with the portion of the patient (e.g., the vein) and at least a portion of the suction force is introduced to the portion of the patient. In this manner, a bodily-fluid is drawn into the fluid reservoir 470. In some embodiments, the bodily-fluid can contain undesirable microbes such as, for example, dermally-residing microbes dislodged during the insertion of the lumen-defining device.

In some embodiments, the rate of expansion of the spring 461 can be modulated by engaging the throttling button 445 included in the engagement portion 444 of the actuator mechanism 440. For example, in some embodiments, it can be desirable to limit the amount of suction force introduced to a vein. In such embodiments, the user can exert a force on the throttling button 445 such that the throttling button 445 is moved to engage the flow control mechanism 430. In this manner, the throttling button 445 can increase the friction between, for example, the second control member 435 and the walls defining the inner volume 421 of the diverter. Thus, the increase in friction between the second control member 435 and the walls defining the inner volume 411 resist the force exerted by the activation extension 446, thereby slowing the rate of expansion of the spring. In this manner, the reduction of pressure (e.g., the increase in negative pressure) of the fluid reservoir 470 can be controlled to maintain a desired pressure differential between the vein and the fluid reservoir 470 and limit the suction force introduced to the vein.

In some embodiments, the user can depress the throttling button 445 to maintain the transfer device 400 in the first configuration. With the desired amount of bodily-fluid transferred to the fluid reservoir 470, a user can disengage the throttling button 445 to disengage the throttling button 445 from the flow control mechanism 430. In this manner, the friction between the second control member 435 and the walls defining the inner volume 411 is reduced and the force of expansion exerted by the spring is sufficient to again overcome the friction between the second control member 435 and the walls defining the inner volume 411. Therefore, the transfer device 400 is moved 400 from the first configuration to the second configuration, wherein a flow of bodily-fluid is transferred to the external reservoir (e.g., such as those described above).

In some embodiments, the desired amount of bodily-fluid transferred to the fluid reservoir 470 is a predetermined amount of fluid. For example, in some embodiments, the transfer device 400 can be configured to transfer bodily-fluid until the pressure within the fluid reservoir 470 is equilibrium with the pressure of the portion of the body in which the lumen-defining device is disposed (e.g., the vein). In such embodiments, the equalizing of the pressure between the fluid reservoir 470 and the portion of the body stops the flow of the bodily-fluid into the fluid reservoir 470. In some embodiments, the predetermined amount of bodily-fluid (e.g., volume) is at least equal to the combined volume of the inlet lumen 423, the first lumen 438, the first outlet lumen 425, and the lumen-defining device.

As described above, the transfer device 400 is moved from the first configuration to the second configuration by further moving the plunger 448 in the distal direction. As the plunger 448 is moved from the first configuration toward the second configuration, the protrusions 447 of the activation extension 446 further engage the activation protrusions 432 included in the first control member 431 to move the flow control mechanism 430 to the second configuration, as indicated by the arrow PP in FIG. 26. In this manner, the flow control mechanism 430 is moved to the second configuration, and the first lumen 438 is fluidically isolated from the inlet lumen 423 and the first outlet lumen 425. In addition, the second lumen 439 defined by the second control member 435 is placed in fluid communication with the inlet lumen 423 defined by the inlet port 422 and the second outlet lumen 427 defined by the second outlet port 426.

Figure 27:
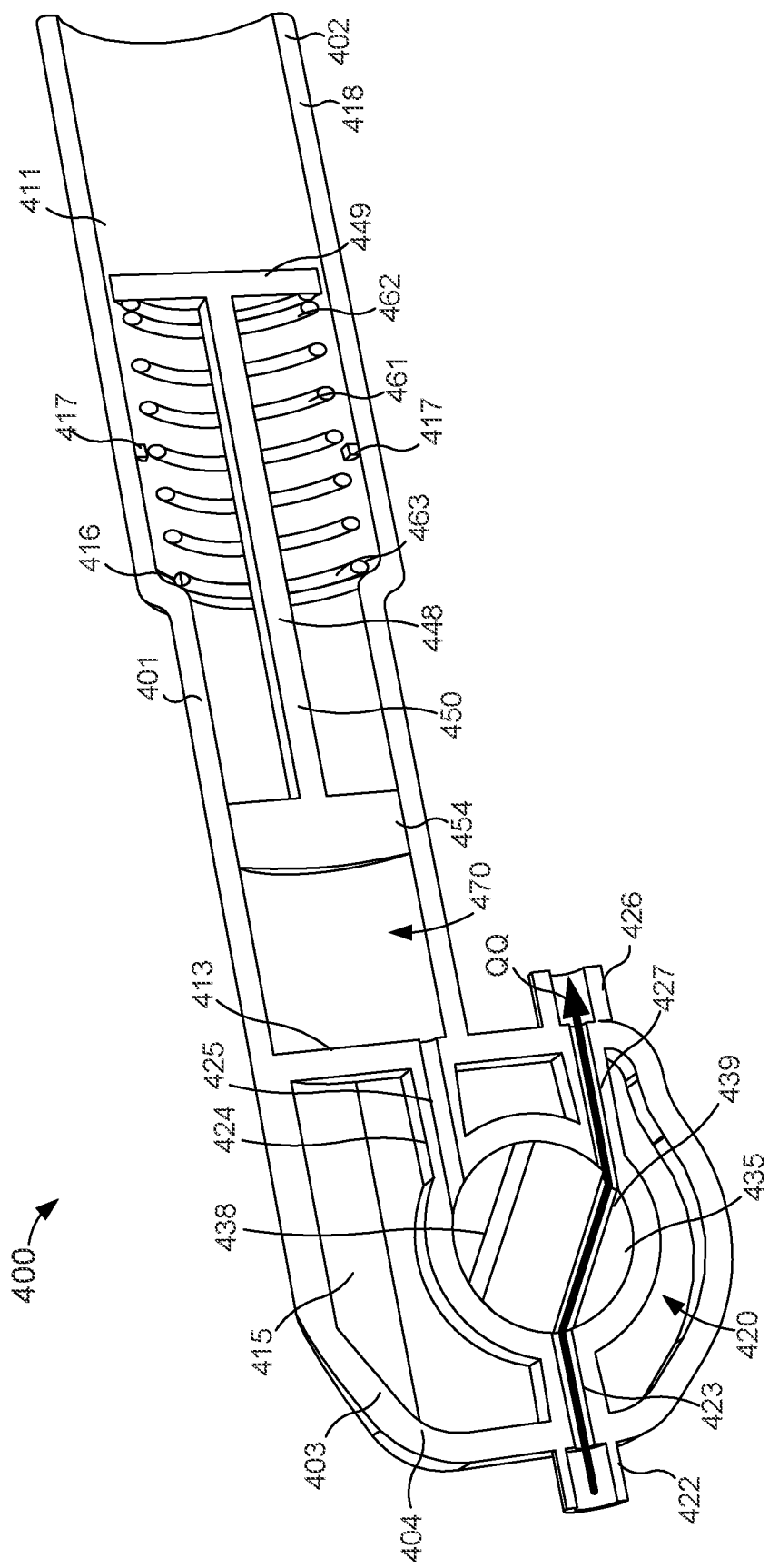
FIG. 27 is a cross-sectional view of the bodily-fluid transfer device of FIG. 25 taken along the line $X_9$-$X_9$.

As shown by the arrow QQ in FIG. 27, the inlet lumen 423 of the inlet port 422, the second lumen 439 of the second control member 435, and the second outlet lumen 427 of the second outlet port 426 define a fluid flow path such that the external reservoir (not shown in FIG. 19) is in fluid communication with the inlet port 422 and, therefore, the portion of the patient (e.g., the vein). Furthermore, the external reservoir is configured to define a negative pressure (e.g., the known external reservoirs referred to herein are vessels defining a negative pressure). The negative pressure within the external reservoir is such that the negative pressure differential between the external reservoir and the portion of the body of the patient introduces a suction force within the portion of the patient. In some embodiments, the user can engage throttling button 445 to again increase the friction between the second control member 435 and the walls defining the inner volume 411. In this manner, further expansion of the spring 461 is limited and a desired amount of bodily-fluid can be drawn into the external reservoir such that the desired amount of bodily fluid is fluidically isolated from the first, predetermined amount of bodily-fluid contained within the fluid reservoir 470.

The bodily-fluid contained in the external reservoir is substantially free from microbes generally found outside of the portion of the patient (e.g., dermally-residing microbes, microbes within a lumen defined by the transfer device 400, microbes within the lumen defined by the lumen defining device, and/or any other undesirable microbe). In some embodiments, with the desired amount of bodily-fluid contained in the external fluid reservoir, the user can disengage the throttling button 445 such that the transfer device returns to the storage configuration. As described above, in this configuration the actuator mechanism 440 can place the flow control mechanism 430 in a third configuration configured to fluidically isolate the first lumen 438 and the second lumen 439 from the inlet lumen 423, the first outlet lumen 425, and the second outlet lumen 427. Thus, the bodily-fluid contained within the fluid reservoir 470 is fluidically isolated from a volume outside the fluid reservoir 470 and the external reservoir can be decoupled from the transfer device 400.

Figure 28:
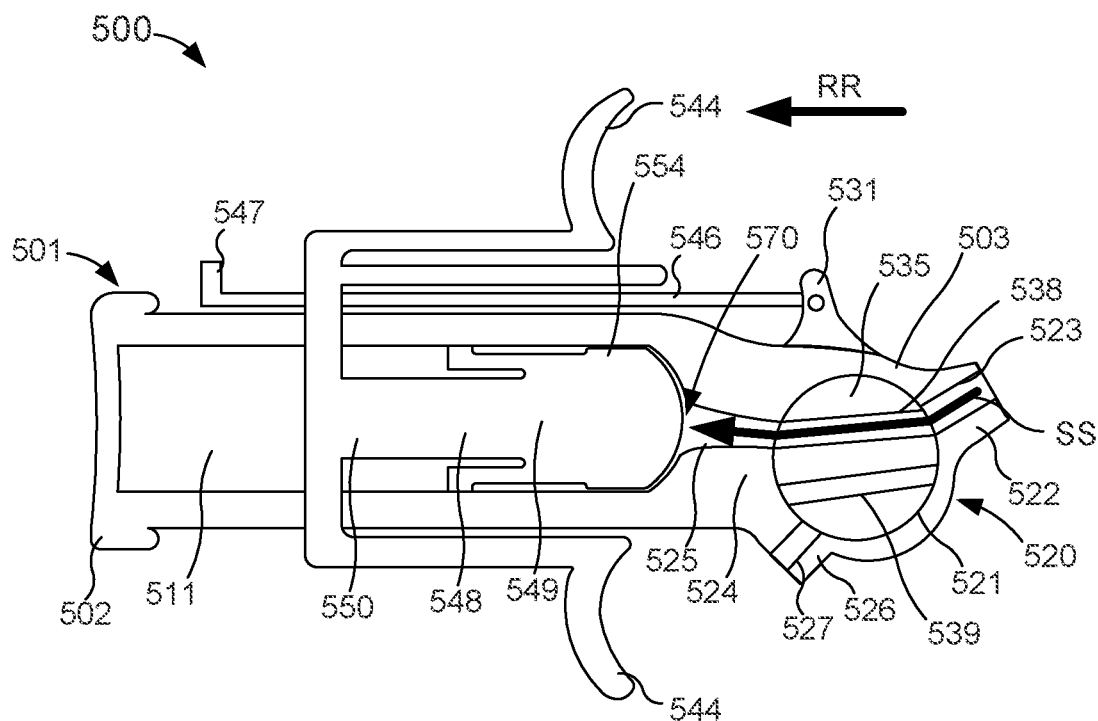
FIGS. 28 and 29 schematic illustrations of a bodily-fluid transfer device according to an embodiment, in a first and second configuration, respectively.
Figure 29:
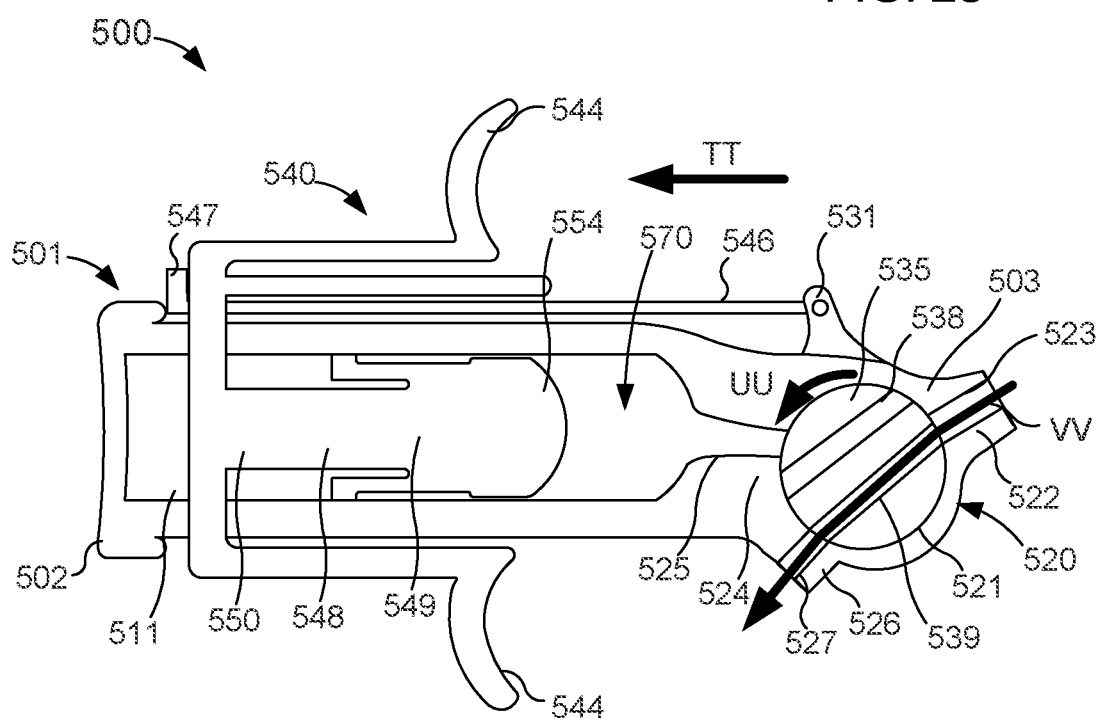

While the transfer device 400 is described above with reference to FIGS. 20-27 as being stored in a storage configuration, in some embodiments, a transfer device can be stored in a first configuration (e.g., defining a flow path between an inlet port and a fluid reservoir). For example, FIGS. 28 and 29 illustrate a transfer device 500 according to an embodiment. In some embodiments, aspects of the transfer device 500 can be substantially similar to corresponding aspects of the transfer device 200. In this manner, details of certain aspects are not described in further detail herein and it should be understood that such aspects are substantially similar in form or function to the corresponding aspects.

The transfer device 500 includes a housing 501, a diverter 520, a flow control mechanism 530, and an actuator 540. The housing 501 includes a proximal end portion 502 and a distal end portion 503. The proximal end portion 502 defines an inner volume configured to receive at least a portion of the actuator mechanism 540, as described in further detail herein. The distal end portion 503 of the housing 501 includes the diverter 520. Similarly stated, the diverter 520 is monolithically formed with the distal end portion 503 of the housing 501. The diverter 520 receives at least a portion of the flow control mechanism 530, as described in further detail herein.

As shown in FIG. 28, the diverter 520 includes an inlet port 522, a first outlet port 524, and a second outlet port 526, and defines an inner volume 521. The inner volume 521 is configured to receive at least a portion of the flow control mechanism 530, as further described herein. The inlet port 522 of the diverter 520 defines an inlet lumen 523. The inlet lumen 523 is configured to be in fluid communication with the inner volume 521. Similarly stated, the inlet lumen 523 of the inlet port 522 extends through a wall defining the inner volume 521 of the diverter 520.

The flow control mechanism 530 includes a first control member 531 and a second control member 535. At least a portion of the flow control mechanism 530 is configured to be disposed within the inner volume 521 defined by the diverter 520. In this manner, the flow control mechanism 530 defines a circular cross-sectional shape such that when the flow control mechanism 530 is disposed within the inner volume 521, a portion of the flow control mechanism 530 forms a friction fit with the walls of the diverter 520 defining the inner volume 521, as described in further detail herein.

The first control member 53 is configured to engage an activation extension 546 of the actuator mechanism 540 and move between a first configuration and a second configuration. The second control member 535 defines a first lumen 538 and a second lumen 539 and is configured to be coupled to the first control member 531. Therefore, the second control member 535 is configured to move concurrently with the first control member 531 when the activation extension 546 engages the first control member 531. Similarly stated, the flow control mechanism 530 is moved between the first configuration and the second configuration when the first control member 531 and the second control member 535 are moved between the first configuration and the second configuration, respectively. Furthermore, when the flow control mechanism 530 is in the first configuration, the first lumen 538 is placed in fluid communication with the inlet lumen 523 defined by the inlet port 522 and the first outlet lumen 525 defined by the first outlet port 524. When the flow control mechanism 530 is in the second configuration, the second lumen 539 is placed in fluid communication with the inlet lumen 523 defined by the inlet port 522 and the second outlet lumen 527 defined by the second outlet port 526, as described in further detail herein.

The actuator mechanism 540 is configured to move between a first configuration and a second configuration, thereby moving the transfer device 500 between a first configuration and a second configuration, as described in further detail herein. The actuator mechanism 540 includes a plunger 548 and the activation extension 546. The plunger 548 includes a proximal end portion 549, a distal end portion 550, and an engagement portion 544 and is configured to be disposed, at least partially within the inner volume 511 of the housing 501. The engagement portion 544 is configured to extend in the distal direction from the proximal end portion 549 of the plunger 548. In this manner, the engagement portion 544 can be engaged by a user to move the actuator mechanism 540 between the first configuration and the second configuration, as described in further detail herein.

The distal end portion 550 of the plunger 548 includes a seal member 554 configured to define a friction fit with the inner surface of the walls defining the inner volume 511. Similarly stated, the seal member 554 defines a fluidic seal with the inner surface of the walls defining the inner volume 511 such that a portion of the inner volume 511 proximal of the seal member 554 is fluidically isolated from a portion of the inner volume 511 distal of the seal member 554. Furthermore, the portion of the inner volume 511 distal of the seal member 554 defines a fluid reservoir 570. Similarly stated, the fluid reservoir 570 defined by the walls defining the inner volume 511 and the seal member 554 of the plunger 548.

The activation extension 546 includes a protrusion 547 configured to selectively engage the proximal end portion 549 of the plunger 548. In this manner, the proximal end portion 549 of the plunger 548 can move the activation extension 546 when the plunger 548 moves from a first configuration to a second configuration, as further described herein.

As described above, the transfer device 500 is stored in the first configuration in which the first lumen 538 of the second control member 535 is in fluid communication with the inlet port 522 and the first outlet port 524. In such embodiments, the friction fit defined by the second control member 535 and the walls of the diverter 520 defining the inner volume 521 maintain the flow control mechanism 530 in the first configuration until the actuator 540 moves the flow control mechanism 530 to the second configuration.

In use, a user can engage the transfer device 500 to couple the inlet port 522 to a proximal end portion of a lumen-defining device (not shown) such as, for example, a butterfly needle. With the inlet port 522 coupled to the lumen-defining device the inlet lumen 523 is placed in fluid communication with the lumen defined by the lumen-defining device. Furthermore, the distal end portion of the lumen-defining device can be disposed within a portion of the body of a patient (e.g., a vein), thus, the inlet lumen 523 is in fluid communication with the portion of the body of the patient. In a similar manner, the second outlet port 526 can be coupled to an external fluid reservoir (not shown).

With the inlet port 522 coupled to the lumen-defining device and the second outlet port 526 coupled to the external fluid reservoir, a user can begin the transfer of a bodily-fluid by applying an activation force to the engagement portion 544 of the actuator 540, thereby moving the plunger 548 in the distal direction, as shown by the arrow RR in FIG. 28. More specifically and as described above, the plunger 548 engages the inner surface of the walls defining the inner volume 511 such that the volume of the fluid reservoir 570 is increased (e.g., as defined by the plunger 548 and the housing 501). With the fluid reservoir 570 being fluidically isolated (as described above) from a volume on the proximal side of the seal member 554, the increase in the volume of the fluid reservoir 570 produces a negative pressure within the fluid reservoir 570. Moreover, with the flow control mechanism 530 in the first configuration, negative pressure differential introduces a suction force within the first lumen 538, the inlet lumen 523, and the first outlet lumen 525.

As shown by the arrow SS, the inlet lumen 523 of the inlet port 522, the first lumen 538 of the second control member 535, and the first outlet lumen 525 of the first outlet port 524 define a fluid flow path such that the second portion 576 of the inner volume 573 defined by the fluid reservoir 570 is in fluid communication with the inlet port 522. Furthermore, with the inlet port 522 coupled to the lumen-defining device the fluid reservoir 570 is in fluid communication with the portion of the patient (e.g., the vein) and at least a portion of the suction force is introduced to the portion of the patient. In this manner, a bodily-fluid is drawn into the fluid reservoir 570. In some embodiments, the bodily-fluid can contain undesirable microbes such as, for example, dermally-residing microbes dislodged during the insertion of the lumen-defining device.

As shown in FIG. 28, the actuator mechanism 540 is configured such that the proximal end portion 549 of the plunger 548 is spaced apart from the protrusion 547 of the activation extension 546. In this manner, the plunger 548 can move in the proximal direction without engaging the protrusion 547 of the activation extension 546. Thus, the plunger 548 can move to introduce the change of the volume in the fluid reservoir 570 without the activation extension 546 moving the first control member 531 from the first configuration toward the second configuration. Therefore, the transfer device 500 can be stored in the first configuration, as described above.

With a desired amount of bodily-fluid transferred to the fluid reservoir 570, a user can move the transfer device 500 from the first configuration to the second configuration, wherein a flow of bodily-fluid is transferred to the external reservoir (e.g., such as those described above). In some embodiments, the desired amount of bodily-fluid transferred to the fluid reservoir 570 is a predetermined amount of fluid. For example, in some embodiments, the transfer device 500 can be configured to transfer bodily-fluid until the pressure within the fluid reservoir 570 is equilibrium with the pressure of the portion of the body in which the lumen-defining device is disposed (e.g., the vein). In such embodiments, the equalizing of the pressure between the fluid reservoir 570 and the portion of the body stops the flow of the bodily-fluid into the fluid reservoir 570. In some embodiments, the predetermined amount of bodily-fluid (e.g., volume) is at least equal to the combined volume of the inlet lumen 523, the first lumen 538, the first outlet lumen 525, and the lumen-defining device.

As shown in FIG. 29, the transfer device 500 can be moved from the first configuration to the second configuration by further moving the actuator mechanism 540 in the distal direction, as indicated by the arrow TT. As the actuator mechanism 540 is moved from the first configuration toward the second configuration, the protrusions 547 of the activation extension 546 is engaged by the proximal end portion 549 of the plunger 548 such that the activation extension 546 is moved in the direction TT. Furthermore, the proximal motion of the activation extension 546 moves the first control member 331 and places the flow control mechanism 530 in the second configuration, as indicated by the arrow UU. In this manner, the first lumen 538 is fluidically isolated from the inlet lumen 523 and the first outlet lumen 525. In addition, the second lumen 539 defined by the second control member 535 is placed in fluid communication with the inlet lumen 523 defined by the inlet port 522 and the second outlet lumen 527 defined by the second outlet port 526.

As shown by the arrow VV, the inlet lumen 523 of the inlet port 522, the second lumen 539 of the second control member 535, and the second outlet lumen 527 of the second outlet port 526 define a fluid flow path such that the external reservoir (not shown in FIGS. 28 and 29) is in fluid communication with the inlet port 522 and, therefore, the portion of the patient (e.g., the vein). Furthermore, the external reservoir is configured to define a negative pressure (e.g., the known external reservoirs referred to herein are vessels defining a negative pressure). The negative pressure within the external reservoir is such that the negative pressure differential between the external reservoir and the portion of the body of the patient introduces a suction force within the portion of the patient. Therefore, a desired amount of bodily-fluid is drawn into the external reservoir and is fluidically isolated from the first, predetermined amount of bodily-fluid contained within the fluid reservoir 570.

The bodily-fluid contained in the external reservoir is substantially free from microbes generally found outside of the portion of the patient (e.g., dermally residing microbes, microbes within a lumen defined by the transfer device 500, microbes within the lumen defined by the lumen defining device, and/or any other undesirable microbe). As described above, the bodily-fluid contained within the fluid reservoir 570 is fluidically isolated from a volume outside the fluid reservoir 570 and the external reservoir can be decoupled from the transfer device 500.

While some embodiments described above include a flow control mechanism that can be rotated to control the flow of a bodily-fluid (e.g., the flow rate) and/or to control the amount of negative pressure within a fluid reservoir, in other embodiments, bodily-fluid transfer device can include any suitable device, mechanism, and/or assembly that can control, at least partially, a flow of bodily-fluid (e.g., the flow rate of the bodily-fluid). For example, FIGS. 30-41 illustrate a transfer device 600 according to an embodiment. The transfer device 600 includes a housing 601, a diverter 620, a flow control mechanism 630, and adjustment mechanism 685, and an actuator 640. The transfer device 600 can be any suitable shape, size, or configuration. For example, the transfer device 600 can have a shape and size that is substantially similar to the transfer device 200 described above with reference to FIGS. 2-12. As such, portions of the transfer device 600 can be substantially similar in form and/or function to corresponding portions of the transfer device 200 of FIGS. 2-12. Thus, aspects of the transfer device 600 are not described in further detail herein.

The housing 601 of the transfer device 600 includes a proximal end portion 602 and a distal end portion 603. The distal end portion 603 includes a base 606 from which a set of walls 604 extend. The walls 604 of the housing 601 define a substantially annular shape and define an inner volume 611 between the proximal end portion 602 and the distal end portion 603. The proximal end portion 602 of the housing 601 is open to receive at least a portion of the diverter 620, a portion of the flow control mechanism 630, and a portion of the actuator 640 within the inner volume 611 (see e.g., FIG. 31). The walls 604 of the housing 601 define a set of status windows 610 and a set of channels 605. The status windows 610 and the channels 605 can be any suitable shape or size. For example, the status windows 610 and the channels 605 can be substantially similar in form and function to the status windows 210 and the channels 205 of the transfer device 200.

Figure 33:
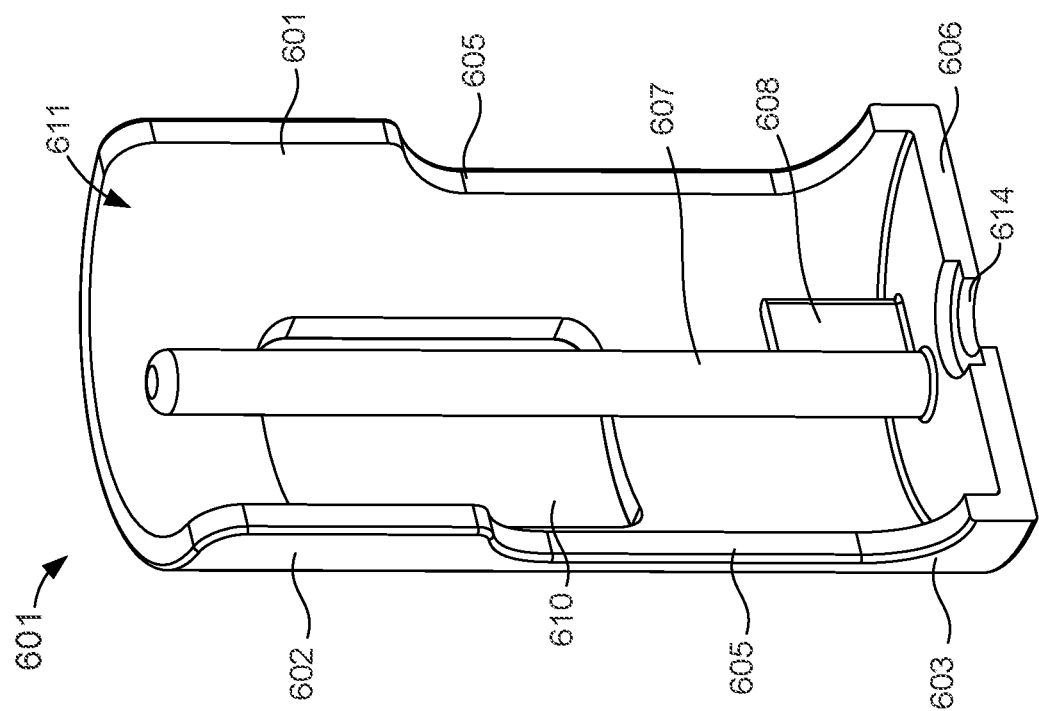
FIG. 33 is a cross-sectional view of the housing illustrated in FIG. 32 taken along the line $X_{11}$-$X_{11}$.
Figure 32:
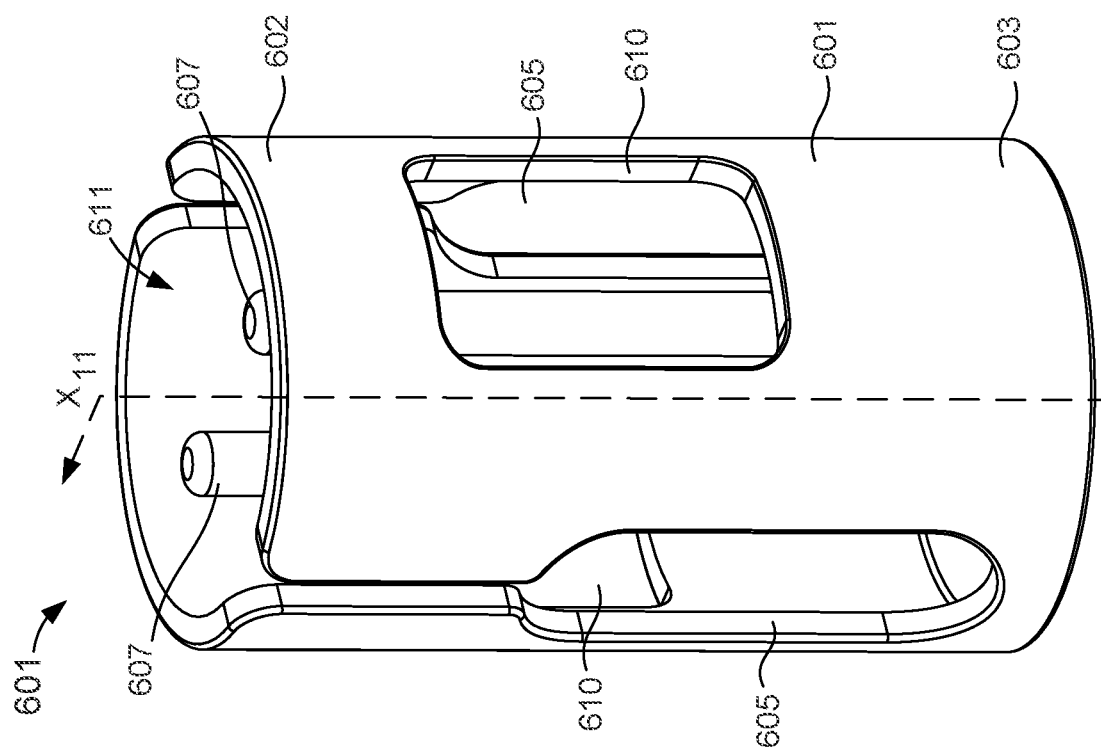
FIG. 32 is a perspective view of a housing included in the bodily-fluid transfer device of FIG. 30.

As shown in FIGS. 32 and 33, the housing 601 includes a set of guide posts 607 and a set of flow control protrusions 608 and defines a passageway 614. The guide posts 607 engage a portion of the diverter 620 and a portion of the actuator 640, as further described herein. The flow control protrusions 608 extend from the base 606 in the proximal direction and can be arranged to selectively engage a portion of the flow control mechanism 630 to move the flow control mechanism 630 between a first configuration and a second configuration, as described in further detail herein. While only one flow control protrusion 608 is shown in FIGS. 32 and 33, the housing 601 can include, for example, two flow control protrusions 608 that are disposed adjacent to a guide post 607. As shown in FIG. 33, the passageway 614 extends through the base 606 and can be arranged to receive a portion of the flow control mechanism 630, as described in further detail herein.

Figure 31:
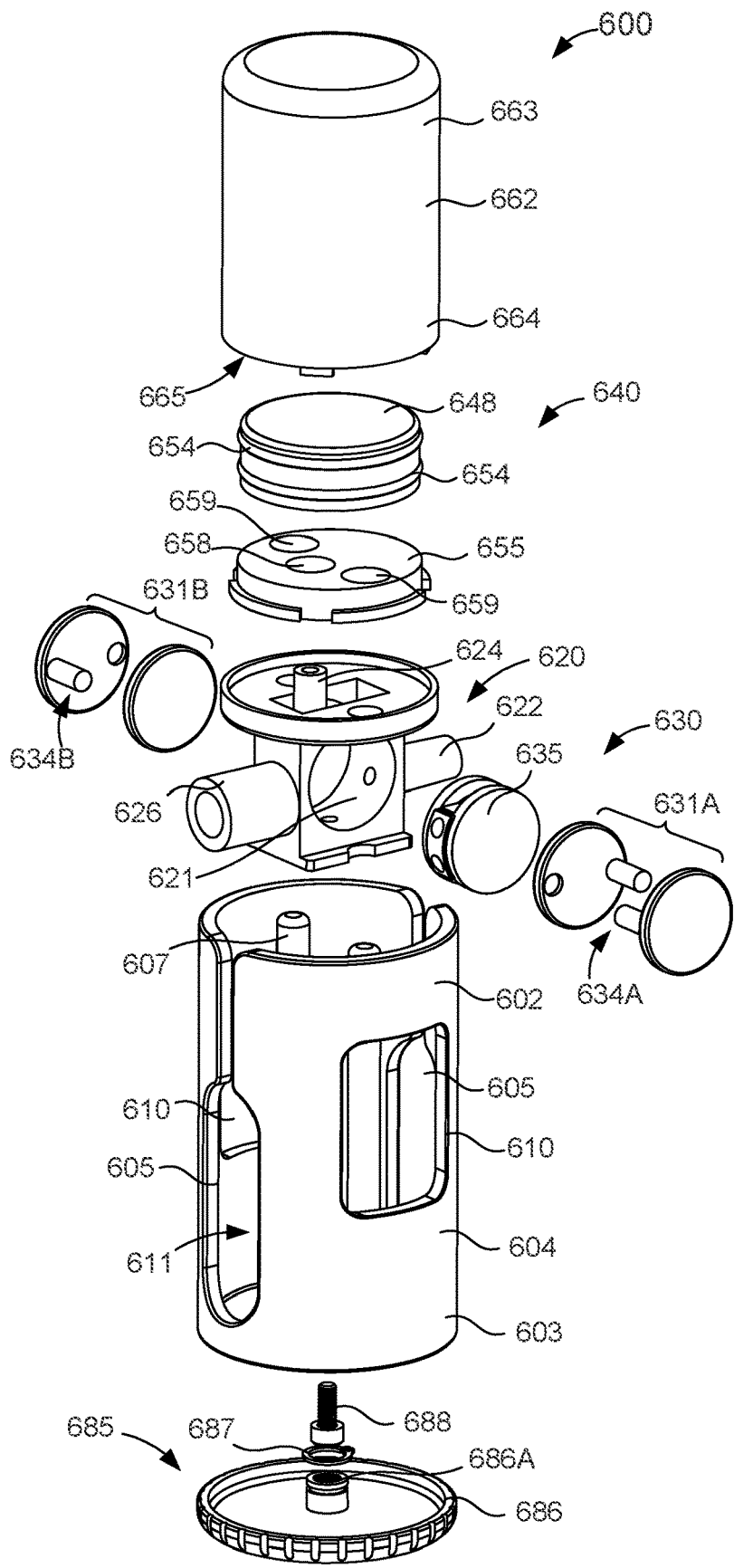
FIG. 31 is an exploded perspective view of the bodily-fluid transfer device of FIG. 30.

As shown in FIG. 31, the actuator mechanism 640 includes the actuator housing 662, a plunger 648, and a cap 655. The actuator mechanism 640 is configured to move between a first configuration and a second configuration, thereby moving the transfer device 600 between a first configuration and a second configuration, as described in further detail herein. The actuator housing 662 includes a proximal end portion 663 and a distal end portion 664 and defines an inner volume 665. The inner volume 665 of the actuator housing 662 receives the plunger 648 and at least a portion of the cap 655. The plunger 648 includes a set of seal member 654 that can form a friction fit with an inner surface (not shown in FIG. 31) of the actuator housing 662 that defines the inner volume 665 of the actuator housing 662. Thus, the plunger 648 can be configured to divide the inner volume 665 into a first portion 667 that is fluidically isolated from a second portion 670 (also referred to herein as "fluid reservoir"). The cap 655 defines an inlet port 658 and a set of guide post ports 659. The inlet port 658 receives a portion of a first outlet port 624 of the diverter 620. The guide post ports 659 movably receive the guide posts 607 of the housing 601 to allow the guide posts 607 to be in contact with the plunger 648. In this manner, the actuator housing 662, the plunger 648, and the cap 655 of the actuator mechanism 640 can be substantially similar to or the same as the actuator housing 262, the plunger 248, and the cap 255, respectively, of the actuator mechanism 640 included in the transfer device 200 described above with reference to FIGS. 2-12. Thus, aspects of the actuator housing 662, the plunger 648, and the cap 655 are not described in further detail herein. As shown in FIG. 31, the actuator mechanism 640 can differ from the actuator mechanism 240 in that the actuator mechanism 640 does not include a spring such as the spring 261 of the actuator mechanism 240. In other embodiments, however, the actuator mechanism 640 can include a spring that is substantially similar to the spring 261.

Figure 34:
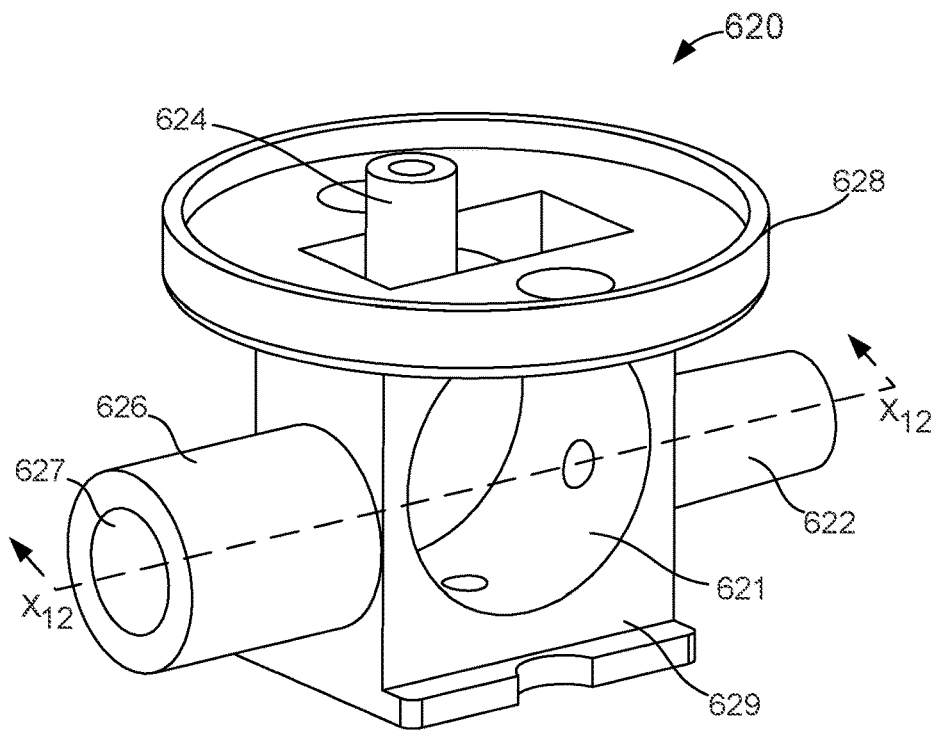
FIG. 34 is a perspective view of a diverter included in the bodily-fluid transfer device of FIG. 30.
Figure 35:
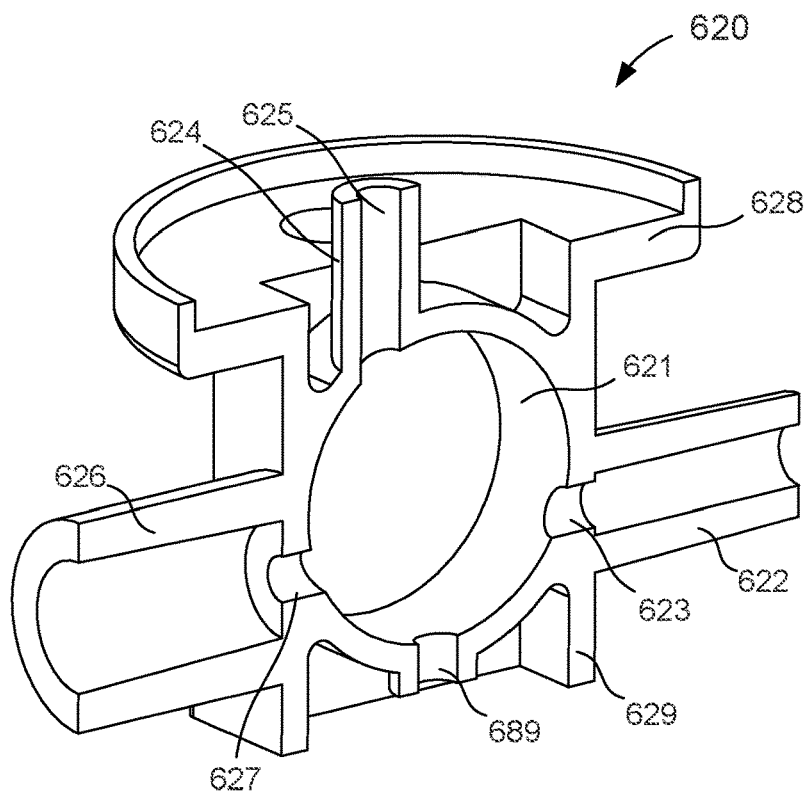
FIG. 35 is a cross-sectional view of the diverter illustrated in FIG. 34 taken along the line $X_{12}$-$X_{12}$.

As shown in FIGS. 34 and 35, the diverter 620 of the transfer device 600 includes a proximal end portion 628 and a distal end portion 629 and defines an inner volume 621. The inner volume 621 can receive at least a portion of the flow control mechanism 630, as described above with reference to the transfer device 200. The proximal end portion 628 of the diverter 620 includes a first outlet port 624. The distal end portion 629 includes an inlet port 622 and a second outlet port 626. The diverter 620 is movably disposed within the inner volume 611 of the housing 601 such that a portion of the inlet port 622 extends through a first channel 605 defined by the walls 604 of the housing 601 and a portion of the second outlet port 626 extends through a second channel 605 opposite the first channel (see e.g., FIG. 30). While not explicitly shown in FIGS. 30-41, the distal end portion 629 of the diverter 620 can engage the guide posts 607 to limit, for example, lateral movement of the diverter 620 as the diverter 620 is moved in the inner volume 611. Similarly stated, the guide posts 607 of the housing 601 can engage the diverter 620 to substantially limit its movement to a proximal direction or distal direction relative to the housing 601, as further described herein.

As shown in FIG. 35, the inlet port 622, the first outlet port 624, and the second outlet port 626 define an inlet lumen 623, a first outlet lumen 625, and a second outlet lumen 627, respectively, that are each in fluid communication with the inner volume 621. The inlet port 622 can be fluidically coupled to a needle or other lumen-containing device (not shown in FIGS. 30-41) that can be disposed within a portion of a body of the patient (e.g., within a vein of the patient), the first outlet port 624 can be fluidically coupled to a portion of the actuator 640, and the second outlet port 626 can be fluidically coupled to an external reservoir (e.g., a sample reservoir not shown in FIGS. 30-41). In this manner, the diverter 620 can be arranged to selectively place the portion of the actuator 640 or the external reservoir in fluid communication with the portion of the body via the inlet port 622 and the first outlet port 624 or via the inlet port 622 and the second outlet port 626, respectively. As shown in FIG. 35, the diverter 620 also defines an opening 689 that can receive a portion of the flow control mechanism 630, as described in further detail herein.

Figure 36:
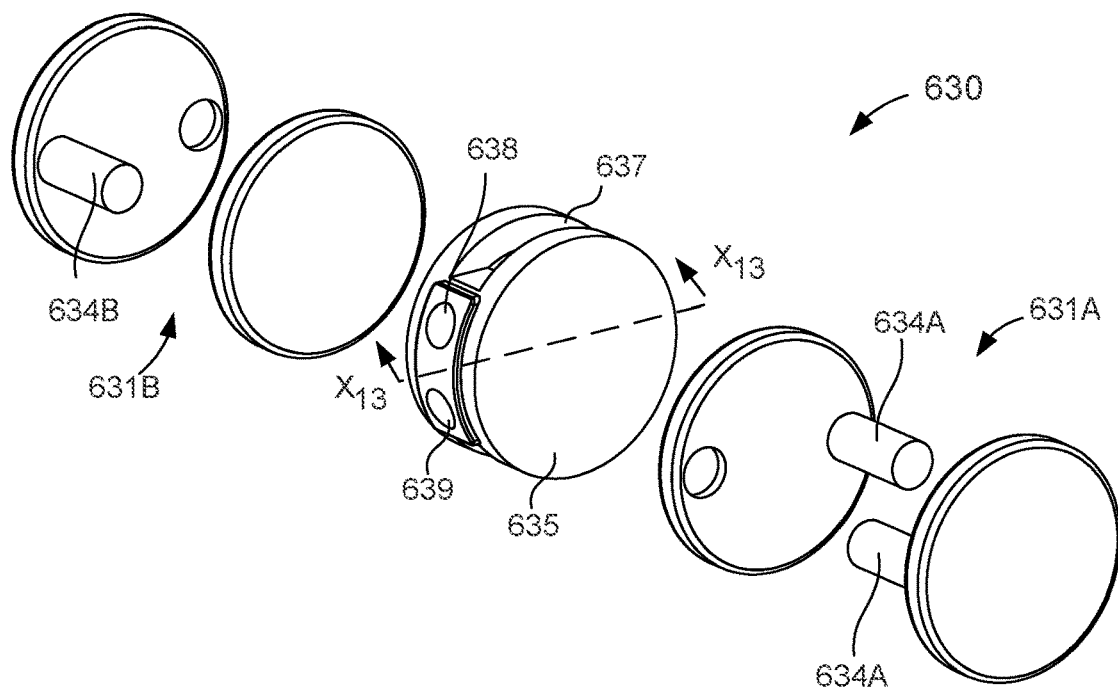
FIG. 36 is a perspective view of a portion of a flow control mechanism included in the bodily-fluid transfer device of FIG. 30.
Figure 37:
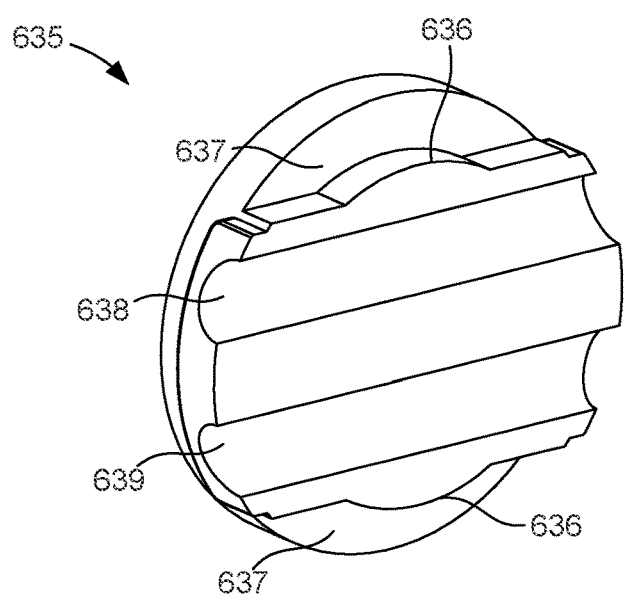
FIG. 37 is a cross-sectional view of the portion of the flow control mechanism illustrated in FIG. 36 taken along the line $X_{13}$-$X_{13}$.

As shown in FIGS. 36 and 37, the flow control mechanism 630 includes a first activation mechanism 631A, a second activation mechanism 631B, a control member 635, and an adjustment mechanism 685. At least a portion of the flow control mechanism 630 is configured to be disposed within the inner volume 621 defined by the diverter 620. More specifically, the flow control mechanism 630 has a circular cross-sectional shape such that when the flow control mechanism 630 is disposed in the inner volume 621, a portion of the control member 635 forms a friction fit with the walls of the diverter 620 defining the inner volume 621, as described in further detail herein. Although not shown in FIGS. 30-41, the flow control mechanism 630 can be arranged within the inner volume 611 of the housing 601 and the inner volume 621 of the diverter 620 such that the first activation mechanism 631A and the second activation mechanism 631B are disposed adjacent to and in contact with the control member 635. More specifically, the first activation mechanism 631A and the second activation mechanism 631B can be in frictional contact with the control member 635. In other embodiments, the first activation mechanism 631A and the second activation mechanism 631B can be coupled to the control member 635 via a mechanical fastener and/or an adhesive. In this manner, the first activation mechanism 631A and the second activation mechanism 631B can be moved concurrently to move the control member 635, as described in further detail herein.

The first activation mechanism 631A and the second activation mechanism 631B include a set of engagement members 634A and 634B, respectively (although only one engagement member 634B is shown in FIG. 36, the second activation mechanism 631B is arranged in similar manner as the first activation mechanism 631A). The engagement members 634A and 634B are configured to engage the flow control protrusion 608 of the housing 601. For example, the diverter 620 and the flow control mechanism 630 can be moved within the inner volume 611 of the housing 601 to place the engagement members 634A and 634B in contact with the flow control protrusions 608. Moreover, once the engagement members 634A and 634B are placed in contact with the flow control protrusions 608, further movement of the diverter 620 and the flow control mechanism 630 can rotate the flow control mechanism 630 relative to the diverter 620 between a first configuration and a second configuration, as described in further detail herein.

As shown in FIG. 37, the control member 635 defines a first lumen 638, a second lumen 639, and a set of channels 637. The channels 637 can be configured to receive a portion of the adjustment mechanism 685, as described in further detail herein. The flow control mechanism 630 can be arranged such that when in its first configuration, the first lumen 638 is placed in fluid communication with the inlet lumen 623 defined by the inlet port 622 and the first outlet lumen 625 defined by the first outlet port 624. Similarly, when the flow control mechanism 630 is in the second configuration, the second lumen 639 is placed in fluid communication with the inlet lumen 623 defined by the inlet port 622 and the second outlet lumen 627 defined by the second outlet port 626. Therefore, the flow control mechanism 630 can be rotated relative to the diverter 620 to selectively place the first outlet port 624 or the second outlet port 626 in fluid communication with the inlet port 622.

Figure 30:
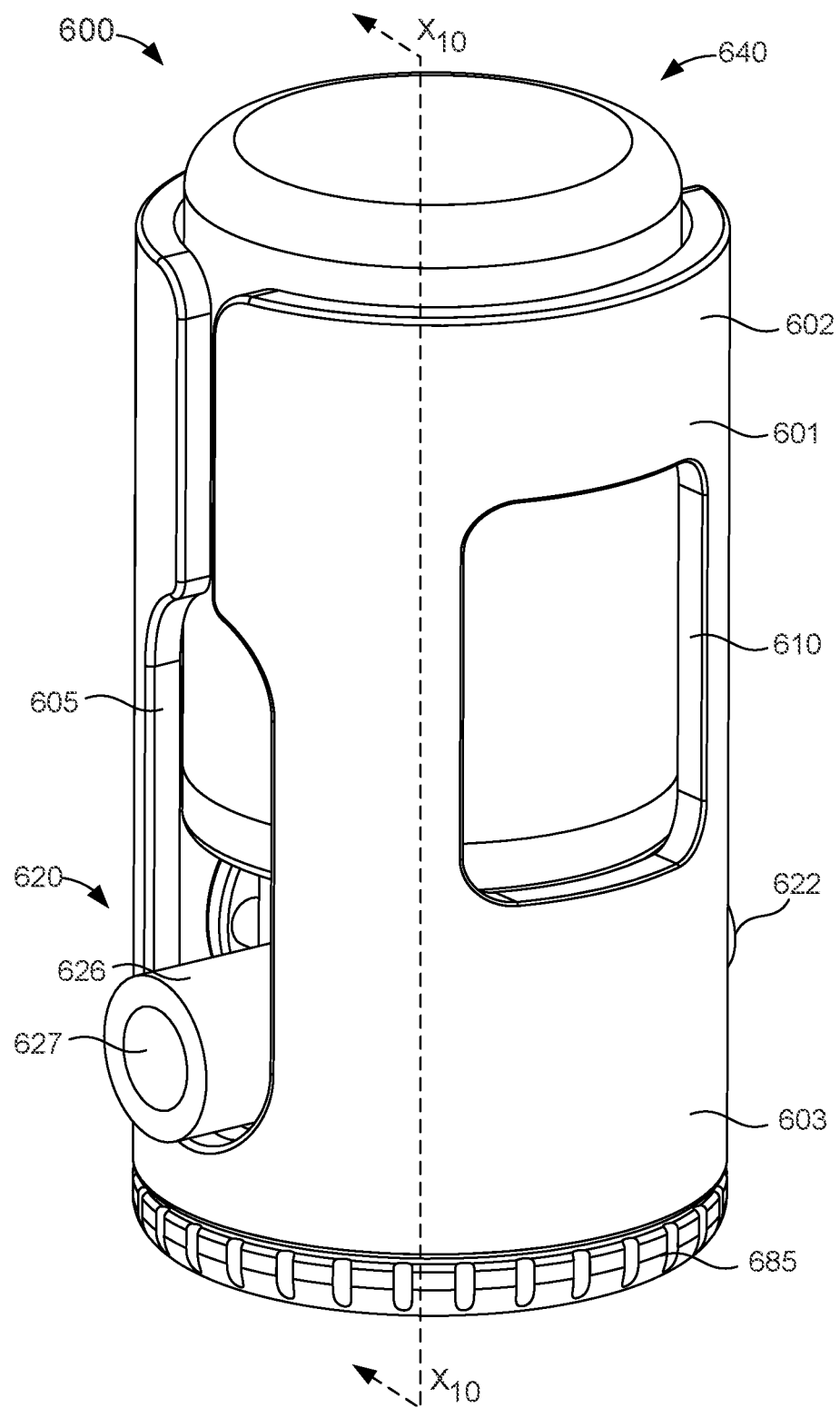
FIG. 30 is a perspective view of a bodily-fluid transfer device according to an embodiment.

The adjustment mechanism 685 includes a dial 686 and an adjustment member 688 (see e.g., FIG. 31). In some embodiments, the adjustment member 688 can be, for example, a screw or the like. As shown in FIG. 30, the adjustment mechanism 685 can be disposed adjacent to the base 606 of the housing 601. More specifically, the dial 686 includes a receiving portion 686A that can be inserted into the passageway 614 defined by the base 606. In this manner, a coupler 687 (e.g., a retaining ring or the like) can be positioned about the receiving portion 686 to limit movement of the dial 686 relative to the base 606. For example, the coupler 687 can be configured to limit translational movement of the dial 686 relative to the base 606 while allowing rotational movement of the dial 686 relative to the base 606. The adjustment mechanism 685 can be arranged such that at least a portion of the adjustment member 688 is movably disposed in the opening 689 defined by the diverter 620. For example, the adjustment member 688 and a set of walls defining the opening 689 of the diverter 620 can define a threaded coupling. Thus, the adjustment member 688 can be rotated relative to the diverter 620 and, as such, the adjustment member 688 can be moved in a translation motion (e.g., proximal or distal direction) relative to the diverter 620. For example, a portion of the adjustment member 688 (e.g., a head of a bolt or screw) can be disposed within the receiving portion 686A of the dial 686 such that as the dial 686 is rotated relative to the housing 601, the adjustment member 688 is rotated relative to the diverter 620. Moreover, a portion of the adjustment member 688 can be disposed within one of the channels 637 of the control member 635. As such, the adjustment mechanism 685 can be manipulated to advance the adjustment member 688 relative to the diverter 620 to place the adjustment member 688 in contact with an engagement surface 636 of the control member 635 (see e.g., FIG. 37). In this manner, the movement of the adjustment member 688 can exert a force on the engagement surface 636 that can be sufficient to deform, bend, or otherwise reconfigure a wall of the control member 635 defining either the first lumen 638 or the second lumen 639, as described in further detail herein.

Figure 38:
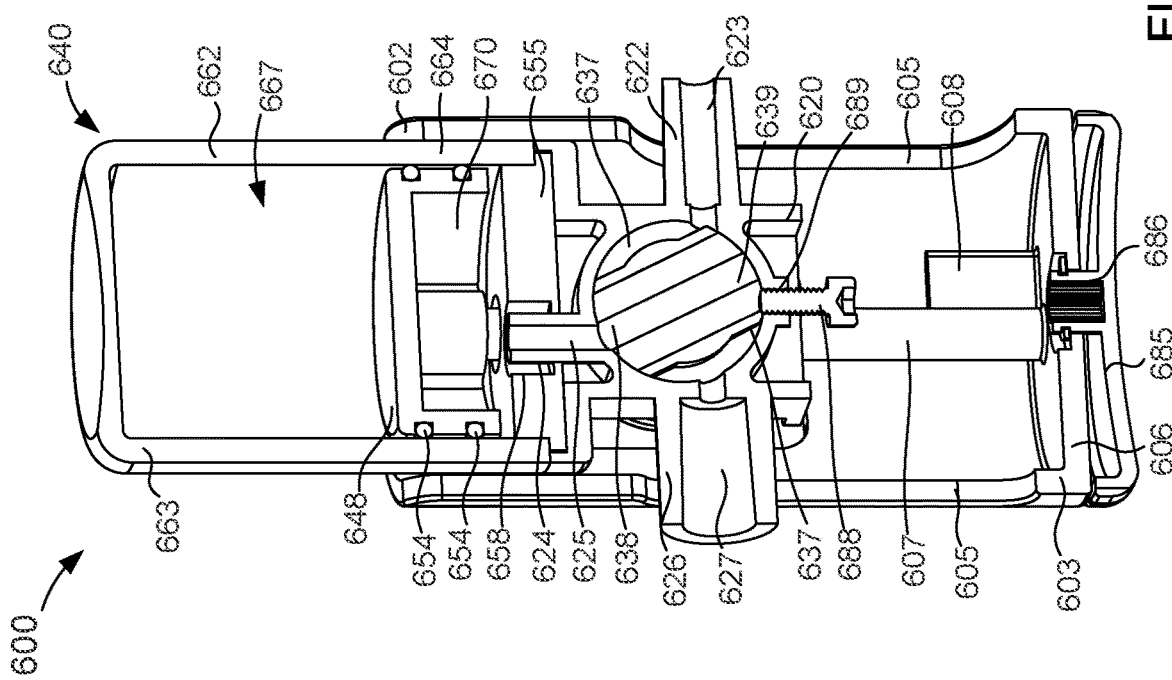
Figure 41:
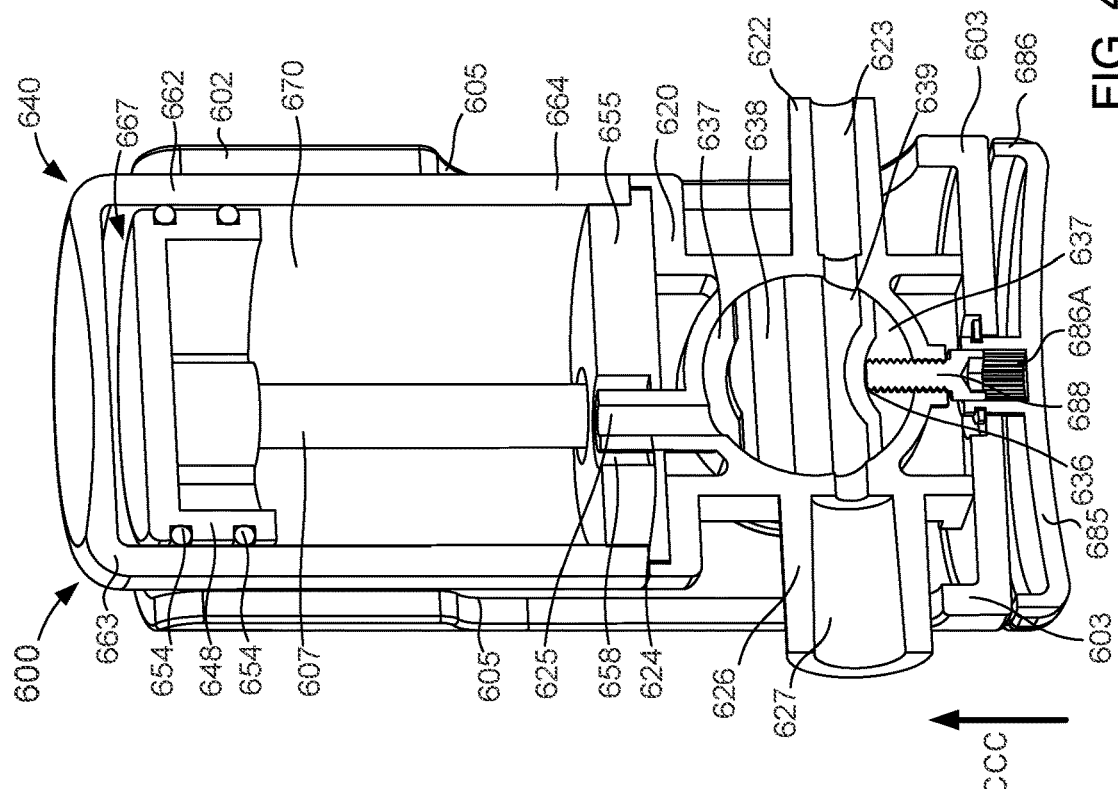

In some embodiments, the transfer device 600 can be stored in a storage configuration (e.g., a first configuration) in which the control member 635 of the flow control mechanism 630 fluidically isolates the inlet port 622, the first outlet port 624, and the second outlet port 626 from the inner volume 621 defined by the diverter 620. In such embodiments, first lumen 638 and the second lumen 639 are fluidically isolated from the inlet lumen 623, the first outlet lumen 625, and the second outlet lumen 627, as shown in FIG. 38. Furthermore, the friction fit defined by the control member 635 and the walls of the diverter 620 defining the inner volume 621 maintain the flow control mechanism 630 in the storage configuration until the flow control mechanism 630 is moved from the storage configuration.

In use, a user can manipulate the transfer device 600 to couple the inlet port 622 to a proximal end portion of a lumen-defining device (not shown) such as, for example, a butterfly needle. The distal end portion of the lumen-defining device can be disposed within a portion of the body of a patient (e.g., a vein), thereby placing the inlet lumen 623 in fluid communication with the portion of the body of the patient. In a similar manner, the second outlet port 626 can be coupled to an external fluid reservoir (not shown). The external fluid reservoir can be any suitable reservoir. For example, in some embodiments, the external fluid reservoir can be a BacT/ALERT® SN or a BacT/ALERT® FA, manufactured by BIOMERIEUX, INC.

With the inlet port 622 coupled to the lumen-defining device and the second outlet port 626 coupled to the external fluid reservoir, a user can move the transfer device 600 from the first configuration to a second configuration by applying an activation force to the actuator mechanism 640. In this manner, at least a portion of the actuator mechanism 640, the diverter 620, and the flow control mechanism 630 are moved in the distal direction toward the second configuration, as indicated by the arrow WW in FIG. 39. More specifically and as described above, the arrangement of the plunger 648 and the guide posts 607 is such that as the user applies the activation force to the actuator mechanism 640, the position of the plunger 648, relative to the housing 601, is maintained. Therefore, the activation force applied by the user moves the actuator housing 662, the cap 655, the diverter 620, and the flow control mechanism 630 in the direction of the arrow WW, but not the plunger 648. The distal movement of the actuator housing 662 is such that the height of the first portion 667 of the inner volume 665 is reduced and the height of the fluid reservoir 670 is increased. With the fluid reservoir 670 being fluidically isolated (as described above) the increase in the height (i.e., the increase in volume) produces a negative pressure within the fluid reservoir 670. Said another way, the movement of the plunger 648 increases the volume of the fluid reservoir 670, which, in turn, produces a negative pressure therein.

Figure 39:
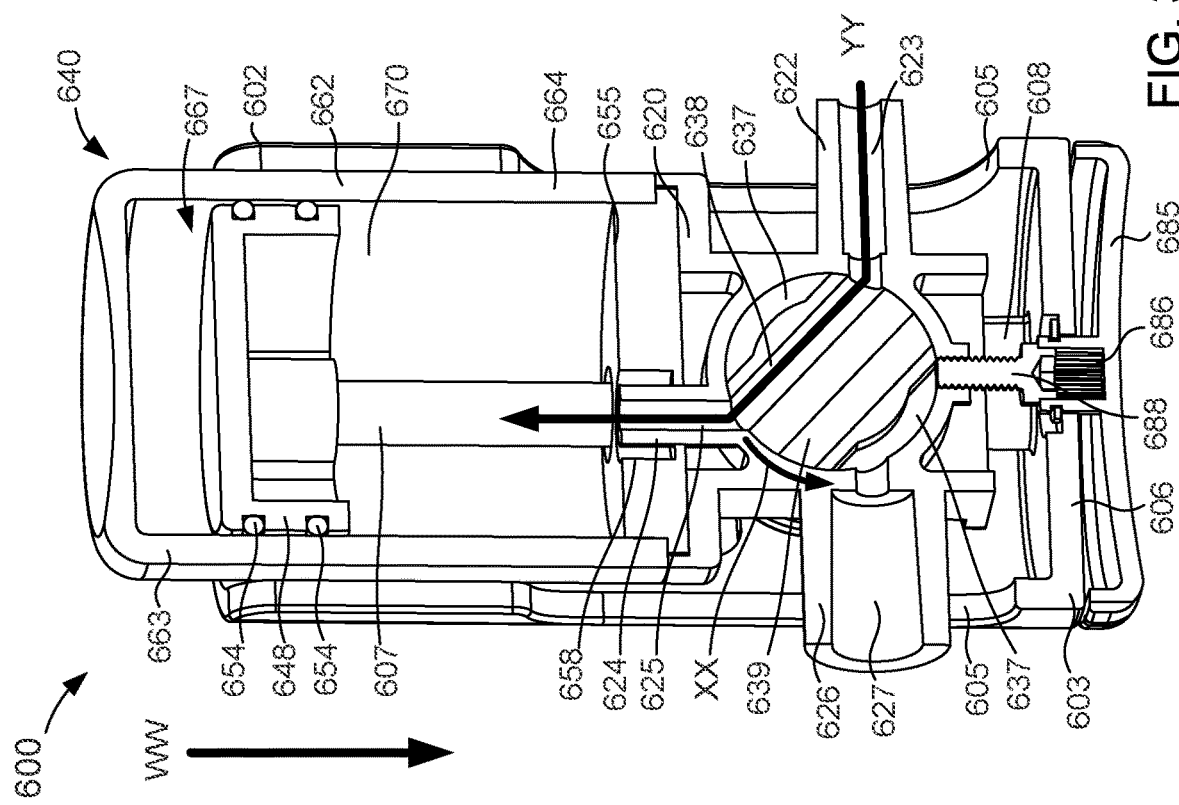
FIGS. 38-41 are cross-sectional views of the bodily-fluid transfer device of FIG. 32 taken along the line $X_{10}$-$X_{10}$, in a first, second, third, and fourth configuration, respectively.

As the actuator mechanism 640 is moved from the storage configuration toward the first configuration, the flow control protrusions 608 engage the engagement members 634A and 634B of the first activation mechanism 631A and the second activation member 631B, respectively, (not shown in FIG. 39) to move the flow control mechanism 630 toward the first configuration, as indicated by the arrow XX in FIG. 39. Thus, when the flow control mechanism 630 is moved to its first configuration, the first lumen 638 defined by the control member 635 is placed in fluid communication with the inlet lumen 623 defined by the inlet port 622 and the first outlet lumen 625 defined by the first outlet port 624. As indicated by the arrow YY in FIG. 39, the inlet lumen 623 of the inlet port 622, the first lumen 638 of the control member 635, and the first outlet lumen 625 of the first outlet port 624 define a fluid flow path such that the fluid reservoir 670 defined by the actuator housing 662 is placed in fluid communication with the inlet port 622. Thus, the negative pressure within the fluid reservoir 670 is such that the negative pressure differential introduces a suction force within the portion of the patient. In this manner, a bodily-fluid is drawn into the fluid reservoir 670 of the actuator housing 662, as indicated by the arrow YY. In some embodiments, the bodily-fluid can contain undesirable microbes such as, for example, dermally-residing microbes. In some instances, the magnitude of the suction force can be modulated by increasing or decreasing the amount of activation force applied to the actuator mechanism 640. In this manner, the change in the volume of the fluid reservoir 670 can be modulated such that a desired amount of a suction force is exerted within the vein of the patient.

With the desired amount of bodily-fluid transferred to the fluid reservoir 670 defined by the actuator housing 662, a user can manipulate the transfer device 600 to move the transfer device 600 from the second configuration to the third configuration, wherein a flow of bodily-fluid is transferred to the external reservoir (e.g., such as those described above). In some embodiments, the desired amount of bodily-fluid transferred to the actuator housing 662 is a predetermined amount of fluid, as described in detail above.

Figure 40:
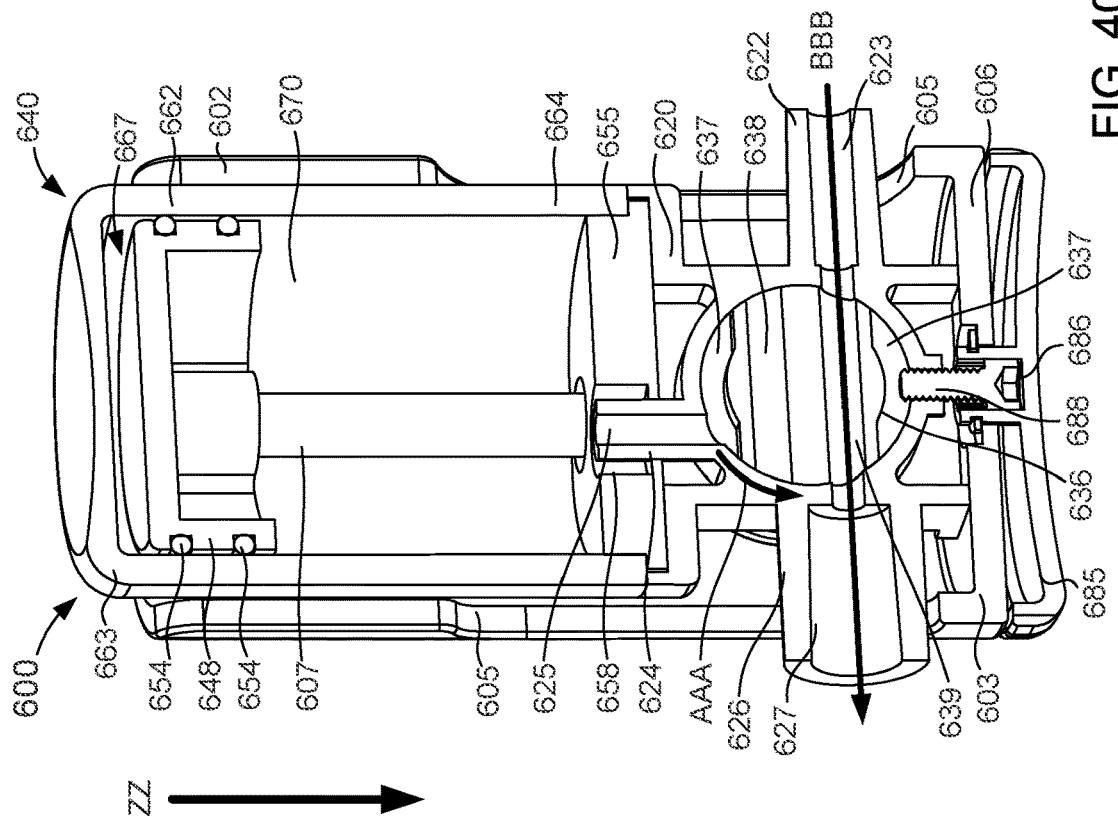
Figure 42:
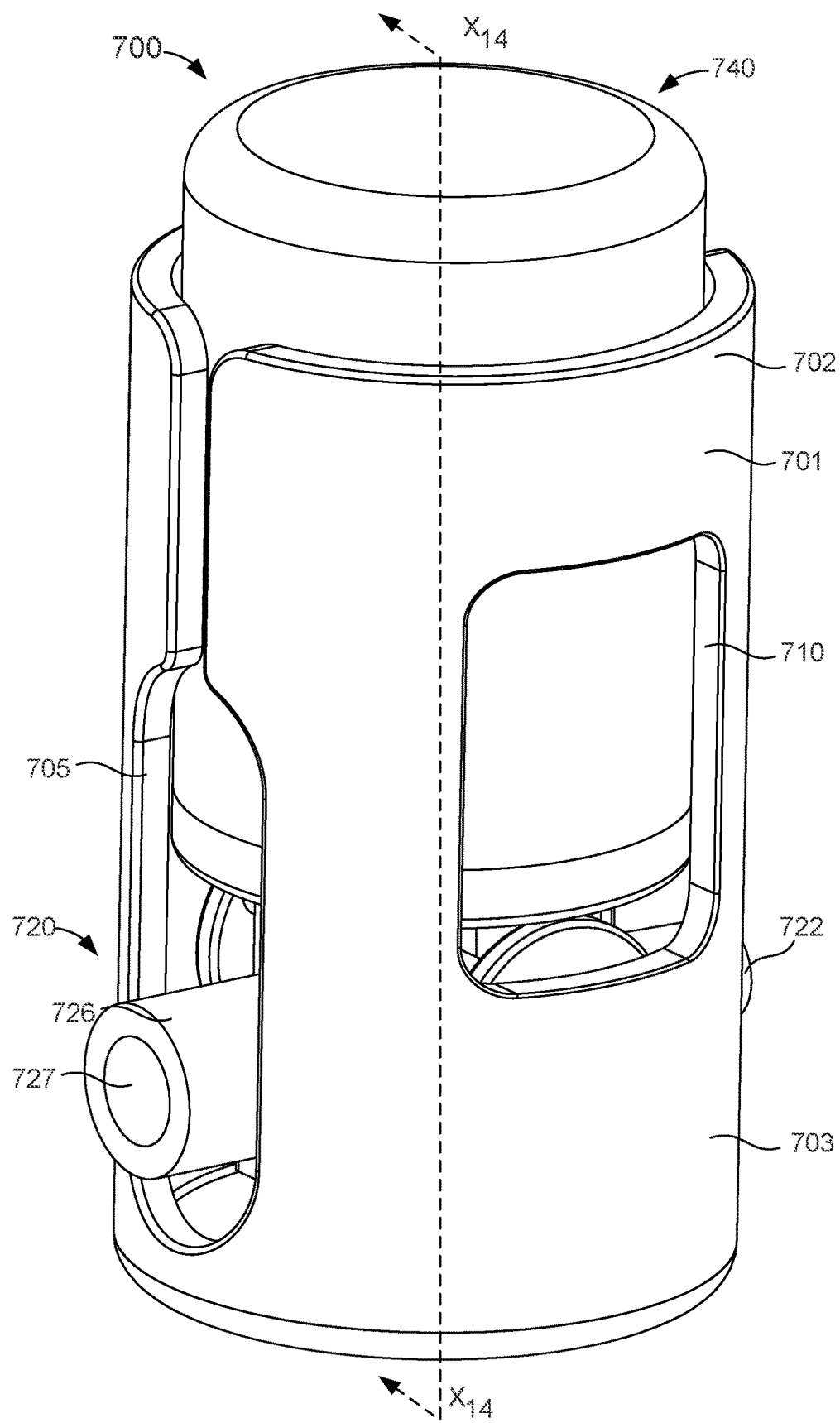
FIG. 42 is a perspective view of a bodily-fluid transfer device according to an embodiment.

The transfer device 600 can be moved from the second configuration to the third configuration by further moving the actuator mechanism 640 in the distal direction, as indicated by the arrow ZZ in FIG. 40. Expanding further, the user can apply an activation force to the actuator mechanism 640 such that the actuator housing 662, the cap 655, the diverter 620, and the flow control mechanism 630 move in the distal direction. With the desired amount of the bodily-fluid disposed within the fluid reservoir 670 the volume of the fluid reservoir 670 is configured to remain constant as the actuator housing 662 and the cap 655 move relative to the plunger 648. Similarly stated, the pressure of the fluid reservoir 670 is configured to remain substantially unchanged as the transfer device 600 is moved from the first configuration to the second configuration. As the actuator mechanism 640 is moved from its first configuration toward its second configuration, the flow control protrusions 608 engage the engagement members 634A and 634B to rotate the flow control mechanism 630 toward the second configuration, as indicated by the arrow AAA. Thus, when the flow control mechanism 630 is moved to its second configuration, the second lumen 639 defined by the control member 635 is placed in fluid communication with the inlet lumen 623 defined by the inlet port 622 and the second outlet lumen 627 defined by the second outlet port 626.

As shown by the arrow BBB, the inlet lumen 623 of the inlet port 622, the second lumen 639 of the control member 635, and the second outlet lumen 627 of the second outlet port 626 define a fluid flow path such that the external reservoir (not shown in FIG. 40) is in fluid communication with the inlet port 622 and, therefore, the portion of the patient (e.g., the vein). Furthermore, the external reservoir is configured to define a negative pressure (e.g., the known external reservoirs referred to herein are vessels defining a negative pressure). The negative pressure within the external reservoir is such that the negative pressure differential between the external reservoir and the portion of the body of the patient introduces a suction force within the portion of the patient. Therefore, a desired amount of bodily-fluid can be drawn into the external reservoir that is fluidically isolated from the first, predetermined amount of bodily-fluid contained within the fluid reservoir 670 defined by the actuator housing 662. In this manner, the bodily-fluid contained in the external reservoir is substantially free from microbes generally found outside of the portion of the patient (e.g., dermally residing microbes, microbes within a lumen defined by the transfer device 600, microbes within the lumen defined by the lumen defining device, and/or any other undesirable microbe).

In some instances, it may be desirable to limit and/or modulate the amount of a suction force exerted on the vein of the patient and/or a flow rate of the bodily-fluid. In such instances, the user can manipulate the adjustment mechanism 685 to move the adjustment member 688 relative to the control member 635. For example, the distal movement of the diverter 620 relative to the housing 601 is such that a portion of the adjustment member 688 is disposed in the receiving portion 686A of the dial 686. In this manner, the dial 686 can be rotated to advance the adjustment member 688 relative to the control member 635, as indicated by the arrow CCC in FIG. 41. Thus, the adjustment member 688 can be moved into contact with the engagement surface 636 to deform a portion of the control member 635 defining the second lumen 639. As such, the wall of the control member 635 constricts the second lumen 639 (e.g., reduces a diameter of at least a portion of the second lumen 639), thereby reducing the suction force exerted within the vein and/or slowing the rate at which the bodily-fluid flows within the second lumen 639. In some embodiments, the dial 686 can be rotated in alternating directions to alternately move the adjustment member 688 in the proximal direction and the distal direction. In this manner, the flow of the bodily-fluid can be, for example, pulsed or the like. In this manner, bodily-fluid that is substantially free from microbes (e.g., dermally residing microbes or the like) can flow with a desired set of characteristics into the external reservoir.

While the transfer device 200 is described above with reference to FIGS. 2-12 as including a linear spring 261 (e.g., a compression spring), in other embodiments, a transfer device can include any suitable spring that can be configured to modulate, change, and/or control a negative pressure within a fluid reservoir and/or a flow rate of a bodily-fluid. For example, FIGS. 42-47 illustrate a transfer device 700 according to another embodiment. The transfer device 700 includes a housing 701, a diverter 720, a flow control mechanism 730, and adjustment mechanism 785, and an actuator 740. The transfer device 70) can be any suitable shape, size, or configuration. For example, portions of the transfer device 700 can be substantially similar to or the same as corresponding portions of the transfer device 200 (described above with reference to FIGS. 2-12) and/or the transfer device 600 (described above with reference to FIGS. 30-41). As such, aspects of the transfer device 700 of the transfer device 700 are not described in further detail herein.

The housing 701 of the transfer device 700 includes a proximal end portion 702 and a distal end portion 703. The distal end portion 703 includes a base 706 from which a set of walls 704 extend. The walls 704 of the housing 701 define a substantially annular shape and define an inner volume 711 between the proximal end portion 702 and the distal end portion 703. The proximal end portion 702 of the housing 701 is open to receive at least a portion of the diverter 720, a portion of the flow control mechanism 730, and a portion of the actuator 740 within the inner volume 711 (see e.g., FIG. 31). The walls 704 of the housing 701 define a set of status windows 710 and a set of channels 705. The status windows 710 and the channels 705 can be any suitable shape or size. For example, the status windows 710 and the channels 705 can be substantially similar in form and function to the status windows 210 and the channels 205 of the transfer device 200. The housing 701 includes a set of guide posts 707 and a set of flow control protrusions (not shown in FIGS. 43-46). In this manner, the housing 701 can function similarly to the housing 601 included in the transfer device 600 described above.

As shown in FIG. 31, the actuator mechanism 740 includes the actuator housing 762, a plunger 748, and a cap 755. The actuator mechanism 740 is configured to move between a first configuration and a second configuration, thereby moving the transfer device 700 between a first configuration and a second configuration, as described in further detail herein. The actuator housing 762 includes a proximal end portion 763 and a distal end portion 764 and defines an inner volume 765. The inner volume 765 of the actuator housing 762 receives the plunger 748 and at least a portion of the cap 755. As such, the actuator mechanism 740 can be substantially similar in form and function as the actuator mechanism 640 included in the transfer device 600 described above with reference to FIGS. 30-41. Thus, the plunger 748 can be disposed in the actuator housing 762 to divide the inner volume 765 into a first portion 767 and a second portion 770 (also referred to herein as "fluid reservoir").

Figure 43:
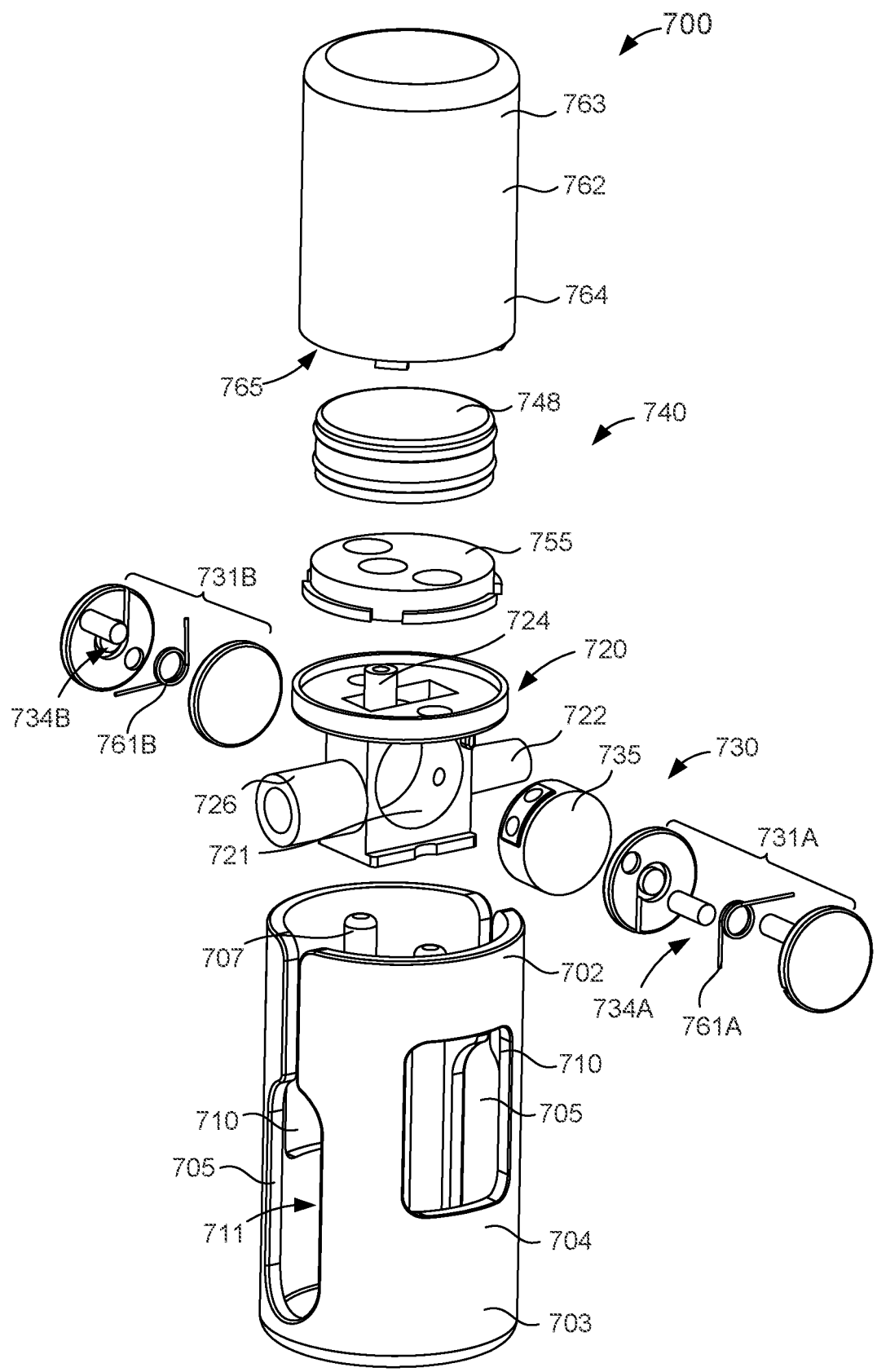
FIG. 43 is an exploded perspective view of the bodily-fluid transfer device of FIG. 42.

As shown in FIG. 43, the diverter 720 of the transfer device 700 includes an inlet port 722, a first outlet port 724, and a second outlet port 726 and defines an inner volume 721. The inner volume 721 can receive at least a portion of the flow control mechanism 730, as described above with reference to the transfer device 200. The diverter 720 is movably disposed within the inner volume 711 of the housing 701 such that a portion of the inlet port 722 extends through a first channel 705 defined by the walls 704 of the housing 701 and a portion of the second outlet port 726 extends through a second channel 705 opposite the first channel (see e.g., FIG. 42). While not explicitly shown in FIGS. 42-46, the distal end portion 729 of the diverter 720 can engage the guide posts 707 to limit, for example, lateral movement of the diverter 720 as the diverter 720 is moved in the inner volume 711. Similarly stated, the guide posts 707 of the housing 701 can engage the diverter 720 to substantially limit its movement to a proximal direction or distal direction relative to the housing 701, as further described herein.

Figure 46:
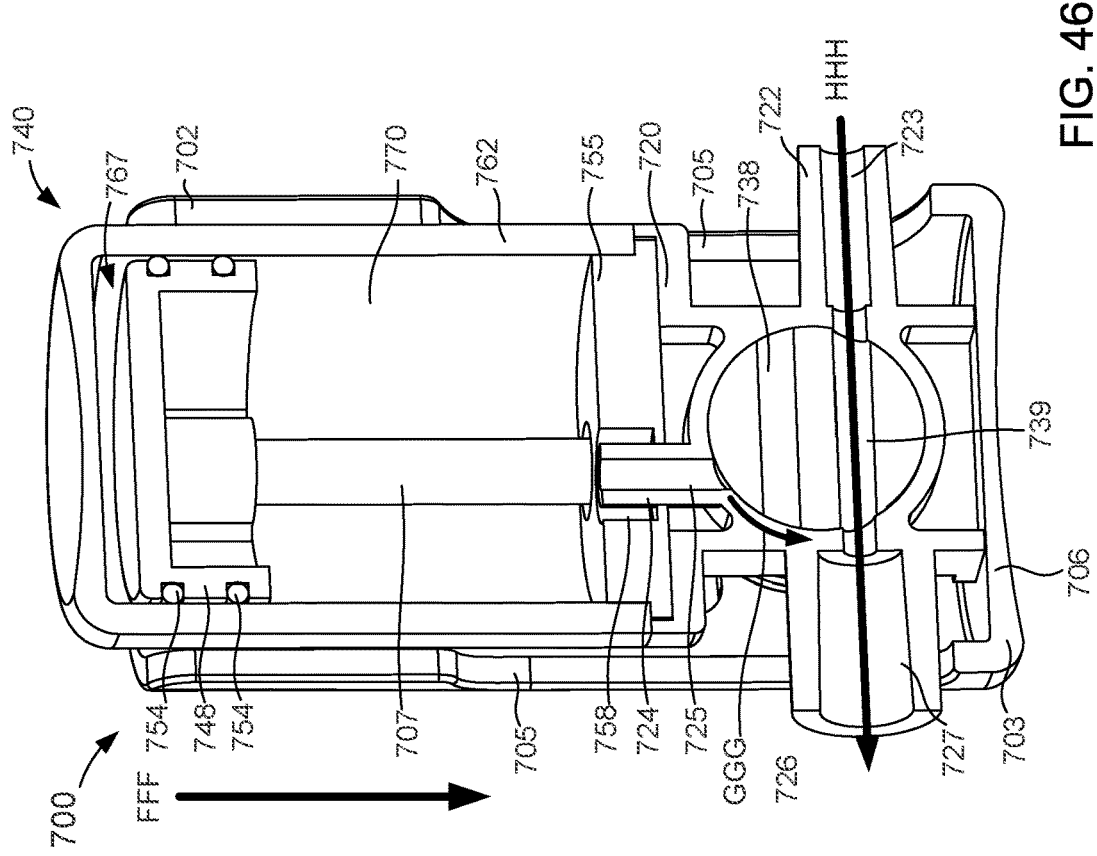
FIGS. 45 and 46 are cross-sectional views of the bodily-fluid transfer device of FIG. 42 taken along the line $X_{14}$-$X_{14}$, in a first configuration and a second configuration, respectively.
Figure 45:
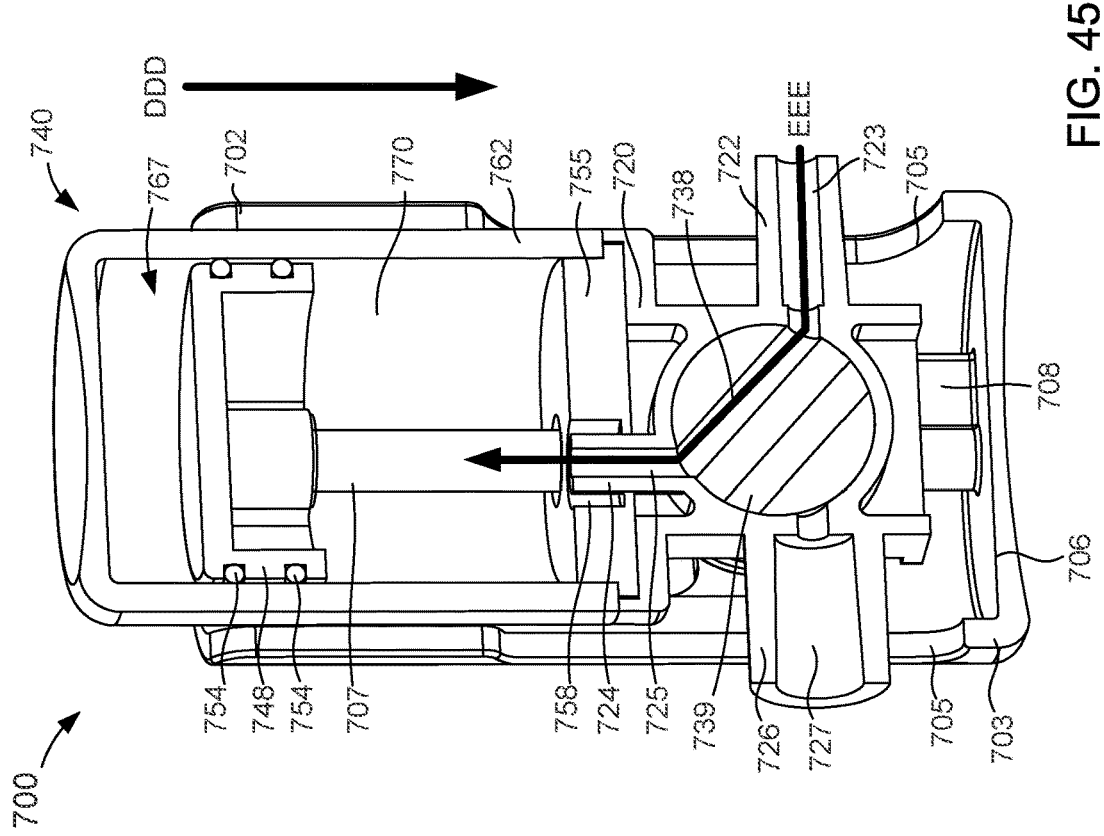

The inlet port 722, the first outlet port 724, and the second outlet port 726 define an inlet lumen 723, a first outlet lumen 725, and a second outlet lumen 727, respectively, that are each in fluid communication with the inner volume 721 (see e.g., FIGS. 45 and 46). The inlet port 722 can be fluidically coupled to a needle or other lumen-containing device (not shown in FIGS. 30-41) that can be disposed within a portion of a body of the patient (e.g., within a vein of the patient), the first outlet port 724 can be fluidically coupled to a portion of the actuator 740, and the second outlet port 726 can be fluidically coupled to an external reservoir (e.g., a sample reservoir not shown in FIGS. 30-41). In this manner, the diverter 720 can be arranged to selectively place the portion of the actuator 740 or the external reservoir in fluid communication with the portion of the body via the inlet port 722 and the first outlet port 724 or via the inlet port 722 and the second outlet port 726, respectively.

Figure 44:
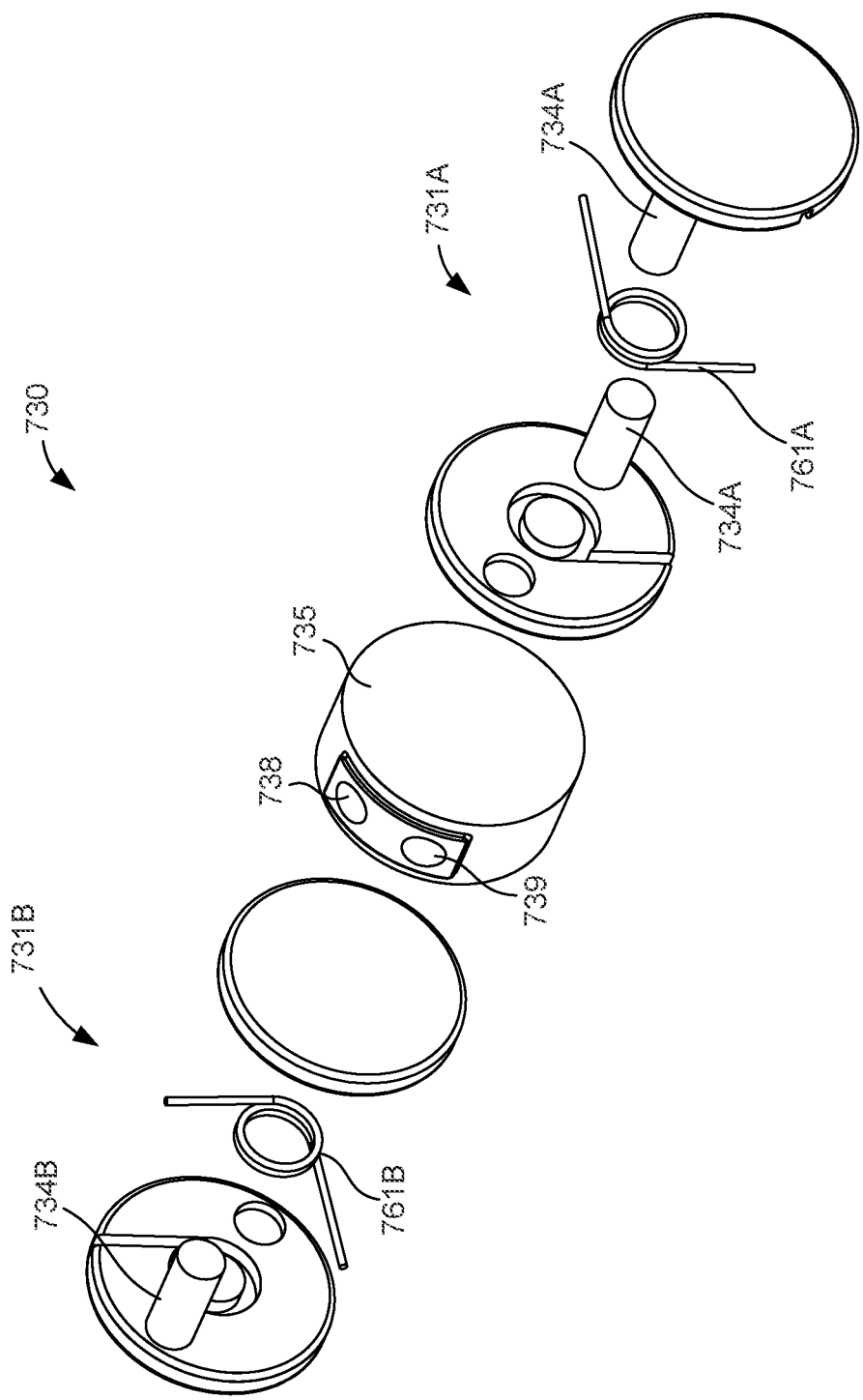
FIG. 44 is a perspective exploded view of a flow control mechanism included in the bodily-fluid transfer device of FIG. 42.

As shown in FIG. 44, the flow control mechanism 730 includes a first activation mechanism 731A, a second activation mechanism 731B, a control member 735, a first torsion spring 761A, and a second torsion spring 761B. At least a portion of the flow control mechanism 730 is configured to be disposed within the inner volume 721 defined by the diverter 720, as described above. Although not shown in FIGS. 42-46, the flow control mechanism 730 can be arranged within the inner volume 711 of the housing 701 and the inner volume 721 of the diverter 720 such that the first activation mechanism 731A and the second activation mechanism 731B are disposed adjacent to and in contact with the control member 735. More specifically, the first activation mechanism 731A and the second activation mechanism 731B can be in frictional contact with the control mechanism 735. In other embodiments, the first activation mechanism 731A and the second activation mechanism 731B can be coupled to the control member 735 via a mechanical fastener and/or an adhesive. In this manner, the first activation mechanism 731A and the second activation mechanism 731B can be moved concurrently to move the control member 735, as described in further detail herein.

The first activation mechanism 731A and the second activation mechanism 731B include a set of engagement members 734A and 734B, respectively (although only one engagement member 734B is shown in FIG. 36, the second activation mechanism 731B is arranged in similar manner as the first activation mechanism 731A). The engagement members 734A and 734B are configured to engage the flow control protrusion 708 of the housing 701, as described with reference to the transfer device 600 of FIGS. 30-41. In use, once the engagement members 734A and 734B are placed in contact with the flow control protrusions 708, further movement of the diverter 720 and the flow control mechanism 730 can rotate the flow control mechanism 730 relative to the diverter 720 between a first configuration and a second configuration. As such, the torsion springs 761A and 761B can be moved from a first configuration having a substantially smaller potential energy to a second configuration having a substantially larger potential energy. In other words, the rotational movement of the flow control mechanism 730 relative to the diverter 720 can transfer the torsion springs 761A and 761B to a configuration having a larger potential energy than the potential energy prior to the rotation of the flow control mechanism 730 relative to the diverter 720, as described in further detail herein.

As shown in FIG. 44, the control member 735 defines a first lumen 738, a second lumen 739. The flow control mechanism 730 can be arranged such that when in its first configuration, the first lumen 738 is placed in fluid communication with the inlet lumen 723 defined by the inlet port 722 and the first outlet lumen 725 defined by the first outlet port 724. Similarly, when the flow control mechanism 730 is in the second configuration, the second lumen 739 is placed in fluid communication with the inlet lumen 723 defined by the inlet port 722 and the second outlet lumen 727 defined by the second outlet port 726. Therefore, the flow control mechanism 730 can be rotated relative to the diverter 720 to selectively place the first outlet port 724 or the second outlet port 726 in fluid communication with the inlet port 722.

In some embodiments, the transfer device 700 can be stored in a storage configuration in which the control member 735 of the flow control mechanism 730 fluidically isolates the inlet port 722, the first outlet port 724, and the second outlet port 726 from the inner volume 721 defined by the diverter 720. In such embodiments, first lumen 738 and the second lumen 739 are fluidically isolated from the inlet lumen 723, the first outlet lumen 725, and the second outlet lumen 727. Furthermore, the friction fit defined by the control member 735 and the walls of the diverter 720 defining the inner volume 721 maintain the flow control mechanism 730 in the storage configuration until the flow control mechanism 730 is moved from the storage configuration.

In use, a user can manipulate the transfer device 700 to couple the inlet port 722 to a proximal end portion of a lumen-defining device (not shown) such as, for example, a butterfly needle. The distal end portion of the lumen-defining device can be disposed within a portion of the body of a patient (e.g., a vein), thereby placing the inlet lumen 723 in fluid communication with the portion of the body of the patient. In a similar manner, the second outlet port 726 can be coupled to an external fluid reservoir (not shown). The external fluid reservoir can be any suitable reservoir. For example, in some embodiments, the external fluid reservoir can be a BacT/ALERT® SN or a BacT/ALERT® FA, manufactured by BIOMERIEUX, INC.

With the inlet port 722 coupled to the lumen-defining device and the second outlet port 726 coupled to the external fluid reservoir, a user can move the transfer device 700 from the first configuration to a second configuration by applying an activation force to the actuator mechanism 740. In this manner, at least a portion of the actuator mechanism 740, the diverter 720, and the flow control mechanism 730 are moved in the distal direction toward the second configuration, as indicated by the arrow DDD in FIG. 45. More specifically and as described above, the distal movement of the actuator housing 762 is such that a height of the first portion 767 of the inner volume 765 is reduced and a height of the fluid reservoir 770 is increased. With the fluid reservoir 770 being fluidically isolated (as described above) the increase in the height (i.e., the increase in volume) produces a negative pressure within the fluid reservoir 770. Said another way, the movement of the plunger 748 increases the volume of the fluid reservoir 770, which, in turn, produces a negative pressure therein.

As shown in FIG. 45, when the flow control mechanism 730 is moved to its first configuration (e.g., from a storage configuration), the first lumen 738 defined by the control member 735 is placed in fluid communication with the inlet lumen 723 defined by the inlet port 722 and the first outlet lumen 725 defined by the first outlet port 724. As indicated by the arrow EEE in FIG. 45, the inlet lumen 723 of the inlet port 722, the first lumen 738 of the control member 735, and the first outlet lumen 725 of the first outlet port 724 define a fluid flow path such that the fluid reservoir 770 defined by the actuator housing 762 is placed in fluid communication with the inlet port 722. Thus, the negative pressure within the fluid reservoir 770 is such that the negative pressure differential introduces a suction force within the portion of the patient. In this manner, a bodily-fluid is drawn into the fluid reservoir 770 of the actuator housing 762, as indicated by the arrow EEE. In some embodiments, the bodily-fluid can contain undesirable microbes such as, for example, dermally-residing microbes.

In some instances, the magnitude of the suction force can be modulated by increasing or decreasing the amount of activation force applied to the actuator mechanism 740. More specifically and as described above, the rotational movement of the flow control mechanism 730 can increase the potential energy of the torsion springs 761A and 761B (not shown in FIG. 45). For example, in some embodiments, an end portion of the torsion springs 761A and 761B can be placed in contact with the flow control protrusions 708 to substantially limit the movement of the end portion of the torsion springs 761A and 761B. Thus, the rotational movement of the first activation mechanism 731A and the second activation mechanism 731B rotates a second end portion of the torsion springs 761A and 761B, respectively, relative to the end portion in contact with the flow control protrusions 708, thereby changing the potential energy of the torsion springs 761A and 761B. In this manner, the torsion springs 761A and 761B can exert a reaction force that can resist the activation force applied to the user on the actuator mechanism 740. Therefore, by reducing the activation force, the flow control mechanism 730 can rotate relative to the diverter 720 to change the alignment of the first lumen 738 of the control member 735 relative to the inlet lumen 723 and the first outlet lumen 725 of the diverter 720. As such, the negative pressure within the fluid reservoir 770 can be reduced and/or otherwise changed.

With the desired amount of bodily-fluid transferred to the fluid reservoir 770 defined by the actuator housing 762, a user can manipulate the transfer device 700 to move the transfer device 700 from the second configuration to the third configuration, wherein a flow of bodily-fluid is transferred to the external reservoir (e.g., such as those described above). In some embodiments, the desired amount of bodily-fluid transferred to the actuator housing 762 is a predetermined amount of fluid, as described in detail above. The transfer device 700 can be moved from the first configuration to the second configuration by further moving the actuator mechanism 740 in the distal direction, as indicated by the arrow FFF in FIG. 46. Expanding further, the user can apply an activation force to the actuator mechanism 740 such that the actuator housing 762, the cap 755, the diverter 720, and the flow control mechanism 730 move in the distal direction. As the actuator mechanism 740 is moved from its first configuration toward its second configuration, the flow control protrusions 708 engage the engagement members 734A and 734B to rotate the flow control mechanism 730 toward the second configuration, as indicated by the arrow GGG. Thus, when the flow control mechanism 730 is moved to its second configuration, the second lumen 739 defined by the control member 735 is placed in fluid communication with the inlet lumen 723 defined by the inlet port 722 and the second outlet lumen 727 defined by the second outlet port 726.

As shown by the arrow HHH in FIG. 46, the inlet lumen 723 of the inlet port 722, the second lumen 739 of the control member 735, and the second outlet lumen 727 of the second outlet port 726 define a fluid flow path such that the external reservoir (not shown in FIG. 46) is in fluid communication with the inlet port 722 and, therefore, the portion of the patient (e.g., the vein). Furthermore, the external reservoir is configured to define a negative pressure (e.g., the known external reservoirs referred to herein are vessels defining a negative pressure). The negative pressure within the external reservoir is such that the negative pressure differential between the external reservoir and the portion of the body of the patient introduces a suction force within the portion of the patient. Therefore, a desired amount of bodily-fluid can be drawn into the external reservoir that is fluidically isolated from the first, predetermined amount of bodily-fluid contained within the fluid reservoir 770 defined by the actuator housing 762. In this manner, the bodily-fluid contained in the external reservoir is substantially free from microbes generally found outside of the portion of the patient (e.g., dermally residing microbes, microbes within a lumen defined by the transfer device 700, microbes within the lumen defined by the lumen defining device, and/or any other undesirable microbe).

In some instances, it may be desirable to limit and/or modulate the amount of a suction force exerted on the vein of the patient and/or a flow rate of the bodily-fluid. In such instances, the user can decrease the activation force applied to the actuator mechanism 740. In this manner, the torsion springs 761A and 761B can exert a force that is operable in rotating the control member 735 relative to the diverter 720. Thus, the flow control mechanism 730 can rotate relative to the diverter 720 to change the alignment of the first lumen 738 of the control member 735 relative to the inlet lumen 723 and the first outlet lumen 725 of the diverter 720. As such, the negative pressure within the fluid reservoir 770 can be reduced, modulated, pulsed and/or otherwise changed.

Figure 47:
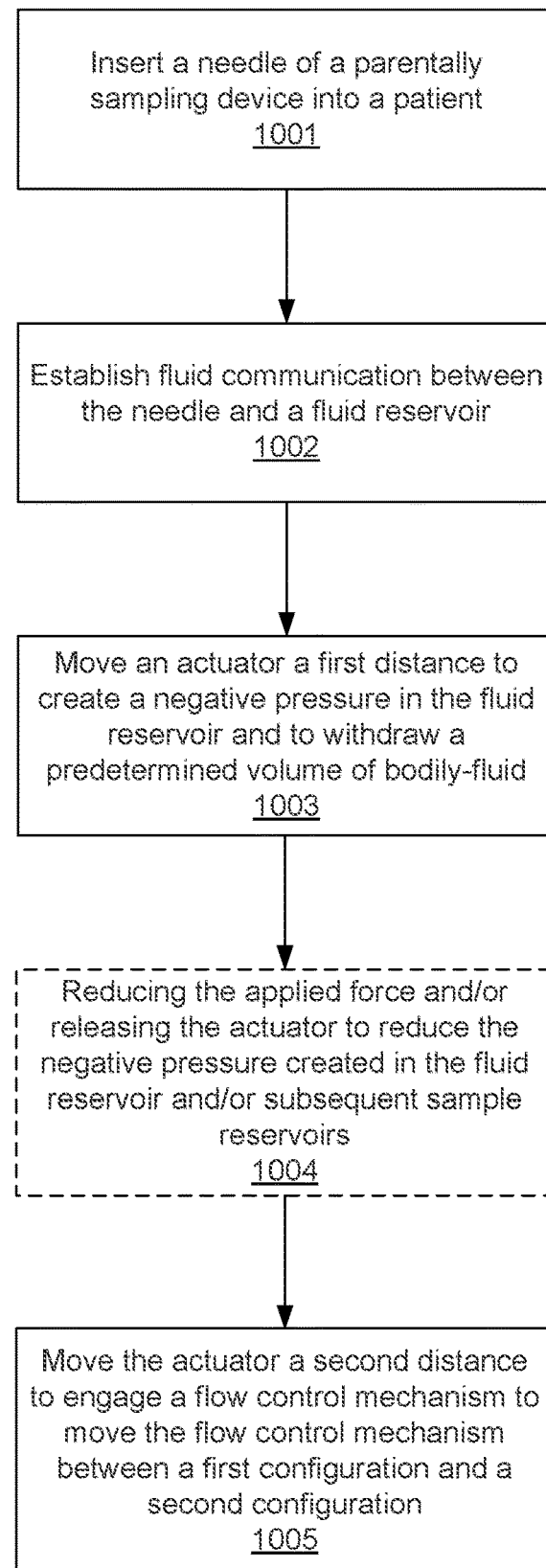
FIG. 47 is a flowchart illustrating a method for parenterally procuring a bodily-fluid sample that is substantially free from microbes.

Referring now to FIG. 47, a flowchart illustrates a method 1000 for parenterally procuring a bodily-fluid sample that is substantially free from microbes. In some embodiments, the method 1000 includes inserting a needle of a parenteral sampling device into a patient, at 1001. In some embodiments, the parenteral sampling device can be, for example, a fluid transfer device such as those described herein. As such, the parenteral sampling device (also referred to herein as "device") can include at least the needle, an actuator, a flow control mechanism, and a fluid reservoir. As described above with reference to the transfer devices 100, 200, 300, 400, 500, 600, and/or 700, the device can be configured to selectively place the needle in fluid communication with the fluid reservoir.

The method 1000 includes establishing fluid communication between the needle and the fluid reservoir, at 1002. For example, in some embodiments, the device can be in a storage configuration prior to use in which the needle is fluidically isolated from the fluid reservoir. Therefore, in use, the device can be manipulated to define a fluid flow path between the needle and the fluid reservoir. In some embodiments, for example, the device can be manipulated to arrange the flow control mechanism included in the device in a first configuration such that the flow control mechanism defines at least a portion of the fluid flow path. For example, the flow control mechanism can be substantially similar to the flow control mechanism 230 included in the transfer device 200 described above with reference to FIGS. 2-12.

With the flow path defined between the needle and the fluid reservoir, an actuator is moved a first distance to create a negative pressure in the fluid reservoir and to withdraw a predetermined volume of bodily-fluid, at 1003. For example, in some embodiments, a user can exert an activation force on the actuator to move the actuator relative to a portion of the device. In such embodiments, the actuator can include a plunger or the like that can be disposed within a portion of the actuator and arranged such that the plunger defines, at least partially, the fluid reservoir. Thus, when the activation force is applied to the actuator, the actuator can move relative to the plunger such that a negative pressure is produced within the fluid reservoir. In this manner, a bodily-fluid can flow through a first flow path from the needle to the fluid reservoir (e.g., via a lumen defined by the flow control mechanism). In some instances, the negative pressure in the fluid reservoir can be reduced, for example, by reducing the activation force applied to the actuator and/or releasing the actuator, at 1004. For example, in some embodiments, the actuator can include a spring and/or any other suitable device, mechanism, or member that can be operable in constricting at least a portion of the fluid flow path. The negative pressure in a subsequent sample reservoir can also be reduced, for example, by apply an activation force to the actuator, at 1004, as described herein.

The method 1000 includes moving the actuator a second distance to engage the flow control mechanism to move the flow control mechanism between the first configuration and a second configuration that is operable in allowing bodily-fluid to flow through a second flow path from the needle to a sample reservoir, at 1005. For example, in some embodiments, by moving the actuator the second distance, the flow control mechanism is rotated such that a lumen defined therein defines at least a portion of the second fluid flow path. In this manner, bodily-fluid can flow through the second flow path to be disposed within the sample reservoir. In some embodiments, the collection and/or the isolation of a first volume of the bodily-fluid can reduce and/or eliminate, for example, an amount of microbes (e.g., dermally-residing microbes, other undesirable external contaminants, or the like) in the sample volume.

While various embodiments have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. Additionally, certain steps may be partially completed and/or omitted before proceeding to subsequent steps.

While various embodiments have been particularly shown and described, various changes in form and details may be made. Although various embodiments have been described as having particular features and/or combinations of components, other embodiments are possible having any combination or sub-combination of any features and/or components from any of the embodiments described herein. For example, while the not shown in FIGS. 28 and 29, in some embodiments, the transfer device 500 can include a throttling button, similar in form and function to the throttling button 445 included in the transfer device 400. By way of another example, although not shown in FIGS. 30-41, in some embodiments, the transfer device 600 can include one or more springs such as, for example, the spring 261 of the transfer device and/or the torsion springs 761A and 761B of the transfer device 700.

The specific configurations of the various components can also be varied. For example, the size and specific shape of the various components can be different than the embodiments shown, while still providing the functions as described herein. More specifically, the size and shape of the various components can be specifically selected for a desired rate of bodily-fluid flow into a fluid reservoir.

The invention claimed is:

1. A blood transfer system, comprising:
a first lumen-containing device configured to be fluidically coupleable to a patient;
a transfer device having an inlet port in fluid communication with the first lumen-containing device, the transfer device defining a first fluid flow path and a second fluid flow path, the transfer device having a seal member disposed at an end portion of the first fluid flow path, a first volume of blood allowed to flow through the first fluid flow path toward the seal member when the transfer device is in a first state, the transfer device retaining the first volume of blood and allowing a second volume of blood to flow through the second fluid flow path while bypassing at least a portion of the first fluid flow path when the transfer device is in a second state; and
a second lumen-containing device fluidically coupleable to a sample reservoir external to the transfer device, the second lumen-containing device configured to allow the second volume of blood to flow from the second fluid flow path into the sample reservoir when the transfer device is in the second state.

2. The blood transfer system of claim 1, wherein the inlet port defines a lumen, the lumen defining a first portion of the first fluid flow path when the transfer device is in the first state and a first portion of the second fluid flow path when the transfer device is in the second state.

3. The blood transfer system of claim 2, wherein the second volume of blood flows past at least a second portion of the first fluid flow path when the transfer device is in the second state.

4. The blood transfer system of claim 1, wherein the first lumen-containing device is a needle configured to be at least partially insertable into the patient, the first volume of blood is at least equal to a volume of a lumen of the needle.

5. The blood transfer system of claim 1, wherein the transfer device transitions from the first state to the second state without manual intervention.

6. The blood transfer system of claim 1, wherein the transfer device automatically transitions from the first state to the second state in response to the first volume of blood substantially filling an inner volume at least partially defined by the seal member.

7. The blood transfer system of claim 6, wherein the transfer device retains the first volume of blood in the inner volume and allows the second volume of blood to flow through the second fluid flow path while bypassing at least a portion of the inner volume when the transfer device is in the second state.

8. The blood transfer system of claim 1, wherein the transfer device automatically changes blood flow from flowing through the first flow path to flowing through the second flow path when the first volume of blood substantially fills an inner volume in fluid communication with the seal member.

9. The blood transfer system of claim 8, wherein the transfer device retains the first volume of blood in the inner volume and allows the second volume of blood to flow through the second fluid flow path while bypassing at least a portion of the inner volume when the transfer device is in the second state.

10. The blood transfer system of claim 1, wherein the seal member forms a fluidic seal with at least one surface of the transfer device to define a portion of an inner volume configured to receive the first volume of blood therein.

11. The blood transfer system of claim 10, wherein the transfer device retains the first volume of blood in the inner volume and allows the second volume of blood to flow through the second fluid flow path while bypassing at least a portion of the inner volume when the transfer device is in the second state.

12. The blood transfer system of claim 1, wherein the seal member transitions the transfer device from the first state to the second state, the transfer device allowing a pressure differential as the seal member transitions the transfer device between the first state and the second state.

13. The blood transfer system of claim 12, wherein the transfer device is in the second state when the pressure differential equalizes.

14. The blood transfer system of claim 1, wherein the transfer device has an outlet port disposed at an end portion of the second fluid flow path, the second volume of blood flows from the second fluid flow path into the second lumen-containing device when the transfer device is in the second state and the second lumen-containing device is fluidically coupled to the outlet port of the transfer device.

15. The blood transfer system of claim 1, wherein the first lumen-containing device is a catheter configured to be at least partially insertable into the patient, the first volume of blood is less than 5 ml.

16. A blood transfer system, comprising:
a first lumen-containing device configured to be fluidically coupleable to a patient;
a transfer device having an inlet port in fluid communication with the first lumen-containing device and an outlet port, the transfer device defining a first fluid flow path, the transfer device having a seal member disposed at an end portion of the first fluid flow path, a first volume of blood allowed to flow through the first fluid flow path toward the seal member when the transfer device is in a first state, the transfer device defining a second fluid flow path configured to receive a second volume of blood such that the second volume of blood flows from the inlet port via the second fluid flow path toward the outlet port while bypassing at least a portion of the first fluid flow path when the transfer device is in a second state; and
a second lumen-containing device fluidically coupleable to a sample reservoir external to the transfer device, the second lumen-containing device configured to allow the second volume of blood to flow from the outlet port to the sample reservoir when the transfer device is in the second state.

17. The blood transfer system of claim 16, wherein the inlet port defines a lumen, the lumen defining a first portion of the first fluid flow path when the transfer device is in the first state and a first portion of the second fluid flow path when the transfer device is in the second state.

18. The blood transfer system of claim 17, wherein the second volume of blood flows past at least a second portion of the first fluid flow path when the transfer device is in the second state.

19. The blood transfer system of claim 16, wherein the first lumen-containing device is a needle configured to be at least partially insertable into the patient, the first volume of blood is at least equal to a volume of a lumen of the needle.

20. The blood transfer system of claim 16, wherein the transfer device transitions from the first state to the second state without manual intervention.

21. The blood transfer device of claim 16, wherein the transfer device automatically transitions from the first state to the second state when the first volume of blood substantially fills an inner volume at least partially defined by the seal member.

22. The blood transfer device of claim 21, wherein the transfer device retains the first volume of blood in the inner volume and allows the second volume of blood to flow through the second fluid flow path while bypassing at least a portion of the inner volume when the transfer device is in the second state.

23. The blood transfer system of claim 16, wherein the transfer device automatically changes blood flow from flowing through the first flow path to flowing through the second flow path when the first volume of blood substantially fills an inner volume at least partially defined by the seal member.

24. The blood transfer device of claim 23, wherein the transfer device retains the first volume of blood in the inner volume and allows the second volume of blood to flow through the second fluid flow path while bypassing at least a portion of the inner volume when the transfer device is in the second state.

25. The blood transfer system of claim 16, wherein the seal member forms a fluidic seal with at least one surface of the transfer device to define a portion of an inner volume such that the first volume of blood is retained therein.

26. The blood transfer device of claim 25, wherein the transfer device retains the first volume of blood in the inner volume and allows the second volume of blood to flow through the second fluid flow path while bypassing at least a portion of the inner volume when the transfer device is in the second state.

27. The blood transfer system of claim 16, wherein the seal member transitions the transfer device from the first state to the second state, the transfer device allowing a pressure differential as the seal member transitions the transfer device between the first state and the second state.

28. The blood transfer system of claim 27, wherein the transfer device is in the second state when the pressure differential equalizes.

29. The blood transfer system of claim 16, wherein the outlet port is disposed at an end portion of the second fluid flow path, the second volume of blood flows from the second fluid flow path into the second lumen-containing device when the transfer device is in the second state and the second lumen-containing device is fluidically coupled to the outlet port of the transfer device.

30. The blood transfer system of claim 16, wherein the first lumen-containing device is a catheter configured to be at least partially insertable into the patient, the first volume of blood is less than 5 ml.

* * * * *